(12) United States Patent
Caers et al.

(10) Patent No.: US 10,869,844 B2
(45) Date of Patent: *Dec. 22, 2020

(54) METHODS FOR THE TREATMENT OF DEPRESSION

(71) Applicant: Janssen Pharmaceutica NV, Beerse (BE)

(72) Inventors: Lodewijk Ivo Caers, Beerse (BE); Jaskaran Singh, San Diego, CA (US); Peter Nicholas Zannikos, Doylestown, PA (US); Wayne C. Drevets, Rancho Santa Fe, CA (US); Ella Daly, Doylestown, PA (US); Carla Marie Canuso, Yardley, PA (US); Margaret Fedgchin, Collegeville, PA (US); Frank Wiegand, Annandale, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/727,594

(22) Filed: Dec. 26, 2019

(65) Prior Publication Data
US 2020/0246279 A1 Aug. 6, 2020

Related U.S. Application Data

(63) Continuation of application No. 14/853,351, filed on Sep. 14, 2015, now abandoned.

(60) Provisional application No. 62/050,439, filed on Sep. 15, 2014.

(51) Int. Cl.
*A61K 31/135* (2006.01)
*A61P 25/24* (2006.01)
*A61K 9/00* (2006.01)
*C12Q 1/6883* (2018.01)

(52) U.S. Cl.
CPC .......... *A61K 31/135* (2013.01); *A61K 9/0043* (2013.01); *C12Q 1/6883* (2013.01); *C12Q 2600/106* (2013.01); *C12Q 2600/156* (2013.01)

(58) Field of Classification Search
CPC .... A61K 31/135; A61K 9/043; C12Q 1/6883; C12Q 2600/156; C12Q 2600/106
See application file for complete search history.

(56) References Cited

U.S. PATENT DOCUMENTS

| 4,994,467 | A | 2/1991 | Zimmerman |
| 5,024,998 | A | 6/1991 | Bodor |
| 5,543,434 | A | 8/1996 | Weg |
| 6,017,961 | A | 1/2000 | Flores et al. |
| 6,040,479 | A | 3/2000 | Steiner et al. |
| 6,176,242 | B1 | 1/2001 | Rise |
| 6,321,942 | B1 | 11/2001 | Krampen et al. |
| 6,572,849 | B2 | 6/2003 | Shahinian, Jr. |
| 7,273,889 | B2 | 9/2007 | Mermelstein et al. |
| 7,687,080 | B2 | 3/2010 | Wolicki |
| 7,896,850 | B2 | 3/2011 | Kronestedt et al. |
| 7,973,043 | B2 | 7/2011 | Migaly |
| 8,785,500 | B2 | 7/2014 | Charney et al. |
| 9,569,220 | B2 | 2/2017 | Jacobs |
| 9,592,207 | B2 | 3/2017 | Charney et al. |
| 10,098,854 | B2 | 10/2018 | Drevets et al. |
| 2004/0138298 | A1 | 7/2004 | Mermelstein et al. |
| 2004/0214215 | A1 | 10/2004 | Yu et al. |
| 2004/0265364 | A1 | 12/2004 | Ozturk et al. |
| 2005/0095277 | A1 | 5/2005 | Ozturk et al. |
| 2006/0223788 | A1 | 10/2006 | Cathcart |
| 2006/0276550 | A1 | 12/2006 | Bhagwat |
| 2007/0256688 | A1 | 11/2007 | Schuster et al. |
| 2007/0287753 | A1 | 12/2007 | Charney et al. |
| 2008/0171075 | A1 | 7/2008 | Ozturk et al. |
| 2009/0306137 | A1 | 12/2009 | Wolfgang et al. |
| 2011/0112131 | A1 | 5/2011 | Holtman et al. |
| 2011/0306674 | A1 | 12/2011 | Schiene et al. |
| 2012/0225949 | A1 | 9/2012 | Papalos |
| 2013/0172361 | A1 | 7/2013 | Fava et al. |
| 2013/0209585 | A1 | 8/2013 | Kim |
| 2013/0236573 | A1 | 9/2013 | Singh et al. |
| 2014/0079740 | A1 | 3/2014 | Salama |
| 2014/0093592 | A1 | 4/2014 | Singh et al. |
| 2014/0256821 | A1 | 9/2014 | Charney et al. |
| 2015/0196501 | A1 | 7/2015 | Erickson et al. |
| 2016/0074340 | A1 | 3/2016 | Caers et al. |
| 2016/0175266 | A1 | 6/2016 | Mermelstein et al. |
| 2016/0332962 | A1 | 11/2016 | Chen et al. |
| 2016/0338977 | A1 | 11/2016 | Singh et al. |
| 2017/0049780 | A1 | 2/2017 | Wainer et al. |
| 2017/0095429 | A1 | 4/2017 | Erickson et al. |

(Continued)

FOREIGN PATENT DOCUMENTS

AU 2016203771 A1 6/2016
CN 103705909 A 4/2014
(Continued)

OTHER PUBLICATIONS

Vann et al. Everyday Health Dec. 2, 2011 (8 pgs).*
(Continued)

*Primary Examiner* — Shirley V Gembeh
(74) *Attorney, Agent, or Firm* — BakerHostetler

(57) ABSTRACT

The present invention is directed to methods and dosing regimens for the treatment of depression (preferably, treatment resistant depression), for the treatment of depression in a suicidal patient, and/or for the treatment and/or prevention of suicidality (e.g. suicidal ideations).

30 Claims, 4 Drawing Sheets

Specification includes a Sequence Listing.

(56) References Cited

U.S. PATENT DOCUMENTS

| | | |
|---|---|---|
| 2018/0042936 A1 | 2/2018 | Lombard |
| 2018/0296478 A1 | 10/2018 | Salce et al. |

FOREIGN PATENT DOCUMENTS

| | | |
|---|---|---|
| CN | 104798728 A | 7/2015 |
| DE | 2062620 | 7/1971 |
| DE | 4312016 A1 | 10/1994 |
| DE | 19619665 A1 | 11/1997 |
| DE | 102007009888 A1 | 9/2008 |
| EP | 1103256 A1 | 5/2001 |
| ES | 2484068 A1 | 8/2014 |
| GB | 1330878 A | 9/1973 |
| JP | 63-002932 A | 1/1988 |
| NZ | 619257 A | 7/2015 |
| WO | 94/23711 A1 | 10/1994 |
| WO | 95/22965 | 8/1995 |
| WO | 96/25925 | 8/1996 |
| WO | 97/07750 | 3/1997 |
| WO | 00/04875 | 2/2000 |
| WO | 02/34293 A2 | 5/2002 |
| WO | 2004/045601 A1 | 6/2004 |
| WO | 2007/111880 A2 | 10/2007 |
| WO | 2009/131794 A1 | 10/2009 |
| WO | 2011/020061 A2 | 2/2011 |
| WO | 2013/003669 A2 | 1/2013 |
| WO | 2013/056229 A1 | 4/2013 |
| WO | 2013/149102 A1 | 10/2013 |
| WO | 2014/020155 A1 | 2/2014 |
| WO | 2014/031975 A1 | 2/2014 |
| WO | 2014/033680 A1 | 3/2014 |
| WO | 2014/169272 A1 | 10/2014 |
| WO | 2015/031410 A1 | 3/2015 |
| WO | 2015/037248 A1 | 3/2015 |
| WO | 2015/101693 A1 | 7/2015 |
| WO | 2015/158854 A1 | 10/2015 |
| WO | 2016/001599 A1 | 1/2016 |
| WO | 2016/044150 A1 | 3/2016 |
| WO | 2016/109427 A1 | 7/2016 |
| WO | 2016/187491 A1 | 11/2016 |
| WO | 2017/003935 A1 | 1/2017 |

OTHER PUBLICATIONS

Bently et al. Med. Clin N Am. 98,981-1005 (2014).*
Zarate, et al., A Randomized Trail of an N-methyl_D-aspartate Antagonist in Treatment-Resistant Major Depression, Arch Gen Psychiatry, 2006, pp. 856-864, vol. 63.
Zarate, et al., An open-Lable Trial of Riluzole in Patients With Treatment-Resistant major Depression, Am J Psychiatry, Jan. 1, 2004, pp. 171-174, vol. 161.
Zarate, et al., Brief Reports an Open-Label Trial of the Glutamate-Modulating Agent Riluzole in Combination with Lithium for the Treatment of Bipolar Depression, Biol Psychiatry, 2005, pp. 430-432, vol. 57.
Zarate, et al., Regulation of Cellular Plasticity Cascades in the Pathophysiology and Treatment of Mood Disorders, AnnalsNew York Academy of Sciences, 2003, pp. 273-291, vol. 1003.
Zarate, et al., Replication of Ketamine's Antidepressant Efficacy in Bipolar Depression: A Randomized Controlled Add-on Trial, Biol Psychiatry, Jun. 1, 2012, pp. 1-18, vol. 71 Issue 11.
Zarate, National Institute of Mental Health, Brain & Behavior Research Foundation Webinar, Ketamine & Next Generation Therapies With Rapid Antidepressant Effects, Aug. 13, 2013, 47 pages.
Zhong, et al., Mood and neuropsychological effects of different doses of ketamine in electroconvulsive therapy for treatment-resistant depression, Journal of Affective Disorders, May 12, 2016, pp. 124-130, vol. 201.
Zou, et al, Potential Neurotoxicity of Ketamine in the Developing Rat Brain, Toxicological Sciences, Dec. 6, 2009, pp. 149-158, vol. 108 Issue 1.
Bartova, et al., Combination of intravenous S-ketamine and oral tranylcypromine in treatment-resistant depression:A report of two cases, European Neuropsychopharmacology, Jul. 28, 2015, pp. 2183-2184, vol. 25.
Bartova, et al., Intravenous Administration of S-ketamine in a Severely Depressed Treatment-resistant Patient Receiving Tranylcypromine: a Case Report, Eur.Psychiat, 2015, pp. 1-1, page number.
Baylor College of Medicine., Optimization of IV Ketamine for Treatment Resistant Depression, ClinicalTrials.gov, Oct. 8, 2008, Ketamine, NCT00768430.
Baylor College of Medicine., Research Study for Major Depressive Disorder: Investigation of Glutamate Medications, ClinicalTrials.gov, Jan. 4, 2007, ketamine, NCT00419003.
Beardslee, et al., A Family-Based Approach to the Prevention of Depressive Symptoms in Children at Risk: Evidence of Parental and Child Change, Pediatrics, 2003, pp. e119-e131, vol. 112 Issue 2.
Beck, et al., Assessment of Depression :The Depression Inventory, Psychological Measurements in Psychopharmacology. Mod. Probl. Pharmacopsychait., 1974, pp. 151-169, vol. 7.
Beck, et al., Assessment of Suicidal Intention: The Scale for Suicide Ideation, Journal of Consulting and Clinical Psychology, 1979, pp. 343-352, vol. 47 Issue 2.
Beck, et al., Scale for Suicide Ideation: Psychometric Properties of a Self-Report Version, Journal of Clinical Psychology, 1988, pp. 499-505, vol. 44 Issue 4.
Beijing Tiantan Hospital, Ketamine and Postoperative Depressive Symptom, ClinicalTrials.gov, Mar. 22, 2017, Ketamine, NCT03086148.
Bender, Neuroscience, 2010a, 169, 720-732.
Berge, "Pharmaceutical Salts", J. Pharm. Sci., 1977, 66, 1-19.
Berman, et al., Antidepressant Effects of Ketamine in Depressed Patients, Biol Psychiatry, Aug. 12, 1999, pp. 351-354, vol. 47.
Berman, et al., The Efficacy and Safety of Aripiprazole as Adjunctive Therapy in Major Depressive Disorder: A Multicenter, Randomized, Double-Blind,Placebo-Controlled Study, J Clin Psychiatry, 2007, pp. 843-853, vol. 68, Issue 6.
Bertolote, et al., Aglobal perspective on the mangnitude of suicide mortality, British Library, 2009, pp. 91-98, Chapter 14.
Bertolote, et al., Suicide attempts, plans, and ideation in culturally diverse sites: the WHO Supre-Miss community survey, Psychological Medicine, 2005, pp. 1457-1465, vol. 35.
Berum, et al., Definition, Assessment, and staging of Traetmenty-Resistant Refractory Major Depression: A Review of Current Concepts and Methods, Can J Psychiatry, 2007, pp. 46-54, vol. 52 Issue 1.
Best, et al., Combined transcranial magnetic stimulation and ketamine for treatment of refractory mood disorder, anxiety, and pain: A case report, Curr Neurobiol, Jan. 25, 2015, pp. 1-4, vol. 8 Issue 1.
Best., Combined ketamine and transcranial magnetic stimulation for treatment resistant depression in the context of chronic OCD: a case report, Devore Best Neuropsychiatric Electrophysiology, 2015, pp. 1-4, vol. 1 Issue 2.
Bickley, et al., Suicide Within Two Weeks of Discharge From Psychiatric Inpatient Care: A Case-Control Study, Psychiatric Services in Advance, Apr. 1, 2013, pp. 1-7.
Birmaher, et al., Childhood and Adolescent Depression: A Review of the Past 10 Years. Part I, J. Am. Acad. Child Adolesc. Psychiatry, Jan. 4, 1996, pp. 1427-1439, vol. 35 Issue 11.
Birmaher, et al., Clinical Presentation and Course of Depression in Youth: Does Onset in Childhood Differ From Onset in Adolescence?,. Am. Acad. Child Adolesc. Psychiatry, Aug. 23, 2003, pp. 63-70, vol. 43 Issue 1.
Birmaher, et al., Course and outcome of child and adolescent major depressive disorder, Child Adolesc Psychiatric Clin N Am, 2002, pp. 619-637, vol. 11.
Birmaher, et al., Practice Parameter for the Assessment and Treatment of Children and Adolescents With Depressive Disorders, J. Am. Acad. Child Adolesc. Psychiatry, 2007, pp. 1503-1526, vol. 46 Issue 11.
Birmaher, et al., Randomized, Controlled Trail of Amitriptyline Versus Placebo for Adolescents With "Treatment-Resistant" Major Depression, J.Am. Acad. Child Adolesc. Psychiatry, Nov. 26, 1998, pp. 527-535, vol. 37 Issue 5.

(56) References Cited

OTHER PUBLICATIONS

Birmaher, et al., Summary of the Practice Parameters for the Assessment and Treatment of Children and Adolescents With Depressive Disorders, J. Am. Acad. Child Adolesc. Psychiatry, 1998, pp. 1234-1238, vol. 37 Issue 11.

Bjorkhem, et al., Clearance of Fentanyl, Alfentanil, Methohexitone, Thiopentone and Ketamine in Relation to Estimated Hepatic Blood Flow in Several Animal Species: Application to Prediction of Clearance in Man, J. Pharm. Pharmacol., Apr. 20, 2000, pp. 1065-1074, vol. 52.

Bjorkhem-Bergman, et al., Comparison of Endogenous 4b-Hydroxycholesterol with Midazolam as Markers for CYP3A4 Induction by Rifampicin, Drug Metabolism and Disposition, May 14, 2013, pp. 1488-1493, vol. 41.

Bjorkman, et al., "Clearance of Fentanyl, Alfentanil, Methohexitone, Thiopentone and Ketamine in Relation to Estimated Hepatic Blood Flow in Several Animal Species: Application to Prediction of Clearance in Man", J. Pharm. Pharmacol., Apr. 20, 2000, pp. 1065-1074, vol. 52.

Blakemore., The social brain in adolescence, Nature Reviews! Neuroscience, 2008, pp. 267-277, vol. 9.

Blier Pierre, Aripiprazole in the Treatment of Delusional Parasitosis With Ocular and Dermatologic Presentations, Journal of Clinical Psychopharmacology, 2013, pp. 271-272, vol. 33 Issue 2.

Blier, et al., On the Safety and Benefits of Repeated Intravenous Injections of Ketamine for Depression, Biol Psychiatry, 2012, pp. e11-e12, vol. 72.

Bodin, et al., Antiepileptic Drugs Increase Plasma Levels of 4-Hydroxycholesterol in Humans, The Journal of Biological Chemistry, Oct. 19, 2001, pp. 38685-38689, vol. 276 Issue 42.

Bolon, Toxicol. Pathol., 2013, 41(7), 1028-1048.

Bolshakov, et al., Determinants of trapp.ing block of N-methyl-D-aspartate receptor channels, Journal of Neurochemistry, Jun. 6, 2003, pp. 56-65, vol. 87.

Bolze, et al., HPLC determination of ketamine, norketamine, and dehydronorketamine in plasma with a high-purity reversed-phase sorbent, Clinical Chemistry, Nov. 13, 19997, pp. 560-564, vol. 44 Issue 3.

Bonanno, et al., Ketamine in war/tropical surgery (a final tribute to the racemic mixture), Injury International Journal of the Care of the Injured, 2002, pp. 323-327, vol. 33.

Bongiovi-Garcia, et al., Comparison of clinical and research assessments of diagnosis.suicide attempt history and suicidal ideation in major depression, Journal of Affective Disorders, Sep. 23, 2008, pp. 183-188, vol. 115.

Bonnet, M.D., Long-Term Ketamine Self-Injections in Major Depressive Disorder: Focus on Tolerance in Ketamine's Antidepressant Response and the Development of Ketamine Addiction, Journal of Psychoactive Drugs, 2015, pp. 276-285, vol. 47 Issue 4.

Borges, et al., Risk factors for twelve-month suicide attempts in the National Comorbidity Survey Replication (NCS-R), Psychol Med, 2006, pp. 1747-1757, vol. 36 Issue 12.

Borges, et al., Twelve-Month Prevalence of and Risk Factors for Suicide Attempts in the World Health Organization World Mental Health Surveys, J Clin Psychiatry, Jul. 10, 2009, pp. 1617-1628, vol. 71 Issue 12.

Botieron, et al, Refractory Depression in Children and Adolescents, Depression and Anxiety, Jul. 28, 1997, pp. 212-223, vol. 5.

Bovill, et al., Alterations in Response to Somatic Pain Associated With Anaesthesia, British Journal of Anaesthesia, 1971, pp. 496-499, vol. 43.

Bowdle, et al., Psychedelic Effects of Ketamine in Healthy Volunteers Relationship to Steady-State Plasma Concentrations, Anesthesiology, 1998, pp. 82-88, vol. 88 Issue 1.

Boyer, et al., Chronic Administration of Imipramine and citalopram Alters the Expression of NMDA Receptor Subunit mRNAs in Mouse Brain, Journal of Molecular Neuroscience, Apr. 9, 1988, pp. 219-233, vol. 10.

Braincells Inc., A Multiple Ascending Dose Study of BCI-838 in Healthy Volunteers, ClinicalTrials.gov, Mar. 2, 2012, BCI-838, NCT01548703.

Braincells Inc.., A Study of BCI-838 and Several Bci-632 Prodrugs in Healthy Volunteers, ClinicalTrials.gov, Mar. 7, 2012, BCI-838, NCT01546051.

Braun, et al, Ketamine induces apoptosis via the mitochondrial pathway in human lymphocytes and neuronal cells, British Journal of Anaesthesia, Apr. 26, 2010, pp. 347-354, vol. 3.

Breakthrough Therapy Design, One Hundred Twelfth Congress of the United States of America at the second session, Breakthrough Therapy Design, 2012, pp. S.3187-2-S.3187-140.

Breakthrough Therapy Design, One Hundred Twelfth Congress of the United States of America at the Second Session, Breakthrough Therapy Design, 2012, pp. S.3187-2-S.3187-140, page number.

Bremner, et al., Measurement of Dissociative Staeswith the Clinician-Administered Dissociative states scale (CADSS), Journal of Traumatic Stress, 1998, pp. 125-136, vol. 11 Issue 1.

Soni,et al., Safety assessment of propyl paraben: a review of the published literature, Food and Chemical Toxicology, Sep. 25, 2000, pp. 513-532, vol. 39, Elsevier Science LTD.

Sos, et al., Relationship of ketamine's antidepressant and psychotomimetic effects in unipolar depression, Activitas Nervosa Superior Rediviva, Aug. 30, 2013, pp. 57-63, vol. 55 Issue 1-2.

Spitzer, "A brief measure for assessing generalized anxiety disorder—the GAD-7". Arch. Intern. Med., 2006, 166(10), 1092-1097.

Spitzer, JAMA, 1999, 282(18), 1737-1744.

Srivastava, et al., Safety and efficacy of ketamine infusion in late onset depression, and conversion to treatment response, Indian J Psychiatry, 2015, pp. 328-329, vol. 57 Issue 3.

St Patrick's Hospital, Ireland., Ketamine as an Adjunctive Therapy for Major Depression (KARMA-dep), ClinicalTrials.gov, Aug. 21, 2017, Ketamine, NCT03256162.

St Patrick's Hospital, Ireland., Ketamine for Depression Relapse Prevention Following ECT (KEEP-WELL), ClinicalTrials.gov, Apr. 13, 2015, Ketamine, NCT02414932.

St Patrick's Hospital, Ireland., Ketamine for Relapse Prevention in Recurrent Depressive Disorder (KINDRED), ClinicalTrials.gov, Jan. 22, 2016, Ketamine, NCT02661061.

Stanford University, Double-Blind Trial of Ketamine Therapy Plus or Minus Naltrexone in Treatment Resistant Depression (TRD) (Ket_Nal), ClinicalTrials.gov, Sep. 22, 2016, Naltrexone, NCT02911597.

Stanford University., Assessing the Effectiveness of Psychiatric Interventions on the Inpatient Unit, ClinicalTrials.gov, Aug. 10, 2018, Ketamine, NCT03626142.

Stannard, et al., Ketamine hydrochloride in the treatment of phantom limb pain, Pain, Apr. 12, 1993, pp. 227-230, vol. 54.

Steven R. Devore Best., Rapid Relief of Treatment Resistant Depression by Facilitated Ketamine Infusion: A Preliminary Report, Activitas Nervosa Superior, Jun. 28, 2014, pp. 28-36, vol. 56 Issue 1-2.

Steven Richard Devore Best., Combined ketamine and transcranial magnetic stimulation for treatment resistant depression in the context of chronic OCD: a case report, Devore Best Neuropsychiatric Electrophysiology, 2015, pp. 1-4, vol. 1 Issue 2.

Stevenson, Ketamine: A Review, Update in Anaesthesia, 20:25-29, 2005.

Straiko, et al., Lithium Protects Against Anesthesia-Induced Developmental Neuroapoptosis, Anesthesiology, 2009, pp. 862-868, vol. 110 Issue 4.

Stucki et al, "Development of ready-to-use ketamine hydrochloride syringes for safe use in post-operative pain", European Journal of Hospital Pharmacy, 2008, vol. 14, Issue 1, pp. 14-18.

Su, et al., Dose-Related Effects of Adjunctive Ketamine in Taiwanese Patients with Treatment-Resistant Depression, Neuropsychopharmacology, May 11, 2017, pp. 2482-2492, vol. 42.

Sunnybrook Health Sciences Centre, Effect of Ketamine vs. Active Placebo on Suicidal Ideation in Depressed Inpatients With Major Depressive Disorder or Bipolar Depression., ClinicalTrials.gov, Nov. 2, 2015, Ketamine, NCT02593643.

(56) References Cited

OTHER PUBLICATIONS

Szymkowicza, et al., A 12-month naturalistic observation of three patients receiving repeat intravenous ketamine infusions for their treatment resistant depression, J Affect Disord, 2013, pp. 1-11, vol. 147.
Tagum, "Redefining affective disorders: relevance for drug Development", CNS Neurosci. ther., 2008, 14(1), 2-9.
Tampere University Hospital, Inhaled Nebulised S(+)-Ketamine for Postoperative Analgesia, ClinicalTrials.gov, Mar. 24, 2015, Ketamine, NCT02397356.
Tamura et al., "An examination of the efficiency of the sequential parallel design in psychiatric clinical trials", Clinical Trails, 2007, 4, 309-317.
Tamura, "Estimation of treatment effect for the sequential parallel design", Stat. Med., 2011, 30(30), 3496-3506.
Tansey et al., Contribution of Common Genetic Variants to Antidepressant Response, Biol Psychiatry, 2013, pp. 679-682, 73.
TC Erciyes University, Intranasal Dexmedetomidine vs Midazolam-ketamine Combination for Premedication of Pediatric Patients, ClinicalTrials.gov, Feb. 26, 2014, ketamine, NCT02072083.
Technische Universitat Monchen, Anesthetics and Auditory, Visceral, and Heat Evoked Potentials, ClinicalTrials.gov, Sep. 26, 2007, S-Ketamine, NCT00534586.
Tel Aviv Medical Center., Intranasal Ketamine for Acute Traumatic Pain, ClinicalTrials.gov, Jun. 29, 2016, Ketamine, NCT02817477.
Tel-Aviv Sourasky Medical Center., Oral Ketamine for Suicidal Ideation, ClinicalTrials.gov, Jan. 16, 2014, Ketamine, NCT02037503.
Thase, et al., Remission Rates Following Antidepressant Therapy With Bupropion or Selective Serotonin Reuptake Inhibitors: A Meta-Analysis of Original Data From 7 Randomized Controlled Trials, J Clin Psychiatry, 2005, pp. 974-981, vol. 66 Issue 8.
Thase, et al., When at First You Dont Succeed: Sequential Strategies for Antidepressant Nonresponders, J Clin Psychiatry, 1997, pp. 23-29, vol. 58 Supplementary 13.
The Cleveland Clinic, ELEKT-D: Electroconvulsive Therapy (ECT) vs. Ketamine in Patients With Treatment Resistant Depression (TRD) (ELEKT-D), ClinicalTrials.gov, Ap. 14, 2017, Ketamine, NCT03113968.
The Cleveland Clinic., Administration of Subanesthetic Dose of Ketamine and Electroconvulsive Treatment for Treatment Resistant Depression, ClinicalTrials.gov, Aug. 13, 2015, Ketamine, NCT02522377.
The Neuroscience Center, LLC., Neuromodulation to Facilitate the Effect of Ketamine (TMS/ketamine), ClinicalTrials.gov, Mar. 22, 2013, Ketamine, NCT01816958.
The University of New South Wales, A Study of Ketamine as an Antidepressant, ClinicalTrials.gov, Sep. 27, 2011, Ketamine, NCT01441505.
The University of New South Wales., Ketamine Trial for the Treatment of Depression, ClinicalTrials.gov, Mar. 27, 2015, Ketamine, NCT02401139.
The University of Texas Health Science Center at San Antonio., Effects of Low Dose Ketamine Given at Induction of Anesthesia on Postoperative Mood in Patients With Depressive Symptoms, ClinicalTrials.gov, Apr. 21, 2015, Ketamine, NCT02422303.
The University of Texas Health Science Center, Houston, Trial of the Rapid Antisuicidal Effects of Intranasal Ketamine in Comorbid Depression and Alcohol Abuse, ClinicalTrials.gov, May 28, 2018, Ketamine, NCT03539887.
The University of Texas Health Science Center, Houston., Low Dose Intravenous Ketamine in Treatment Resistant Depression Patients (ketamine), ClinicalTrials.gov, Oct. 17, 2016, Ketamine, NCT02935595.
The University of Texas Health Science Center, Houston., The UTHealth Ketamine Project, ClinicalTrials.gov, Aug. 30, 2016, Ketamine, NCT02882711.
Thomas P. Laughren, Comorbid Mood Disorders and Medical Illness: A Food and Drug Administration Perspective, Biol Psychiatry, 2003, pp. 195-199, vol. 53.
Torjesen, "Ketamine helps a third of patients with treatment resistant depression, finds small UK study", BMJ, Apr. 3, 2014, pp. 92576-92576, vol. 348.
Trevithick, et al., Study protocol for the randomised controlled trial: Ketamine augmentation of ECT to improve outcomes in depression (Ketamine-ECT study), Trevithick et al. BMC Psychiatry, 2015, pp. 1-11, vol. 15 Issue 257.
Trivedi et al., "The Inventory of Depressive Symptomatology, Clinical Rating (IDS-C) and Self-Report (IDS-SR) in public sector patients with mood disorders: a psychometric evaluation", Psychol. Med., 2004, 34(1), 73-82.
Trivedi, et al., Evaluation of Outcomes With Citalopram for Depression Using Measurement-Based Care in STAR*D: Implications for Clinical Practice, Am J Psychiatry, 2006, pp. 28-40, vol. 163 Issue 1.
Trottier., Pain Free Laceration Repairs Using Intra-nasal Ketamine, ClinicalTrials.gov, Feb. 15, 2017, Ketamine, NCT03053947.
Trullas, et al., Functional antagonists at the NMDA receptor complex exhibit antidepressant actions, European Journal of Pharmacology, May 29, 1990, pp. 1-10, vol. 185, Elsevier Science Publishers B.V.
Turku University Hospital, Dose-response of Ketamine in Patient Controlled Analgesia in Orthopaedic Surgery Patients (DoseRespKeta). ClinicalTrials.gov, Dec. 15, 2016, S-Ketamine, NCT02994173.
Udo Bonnet, M.D., Long-Term Ketamine Self-Injections in Major Depressive Disorder: Focus on Tolerance in Ketamine's Antidepressant Response and the Development of Ketamine Addiction, Journal of Psychoactive Drugs, 2015, pp. 276-285, vol. 47 Issue 4.
UN Convention_Psychotropic Substances, Convention on Psychotropic Substance, UN Convention_Psychotropic Substances, 1971, pp. 1-28, page number.
UN Economic Social Council., Changes in the scope of control of substances Note by the Secretariat, UN Economic Social Council, Dec. 16, 2014, pp. 1-15, page number.
Niciua, et al., Subanesthetic Dose Ketamine Does Not Induce an Affective Switch in Three Independent Samples of Treatment-Resistant Major Depression, Biol Psychiatry, Nov. 15, 2013, pp. 1-3, vol. 74 Issue 10.
Nierenberg, et al., A Comparison of Lithium and T3 Augmentation Following Two Failed Medication Treatments for Depression: A STAR*D Report, Am J Psychiatry, Jun. 26, 2006, pp. 1519-1530, vol. 163 Issue 9.
Nierenberg, et al., Suicide risk management for the sequenced treatment alternatives to relieve depression study: applied NIMH guidelines, Journal of Psychiatric Research, Mar. 12, 2004, pp. 583-589, vol. 38.
Nock, et al., Cross-National Analysis of the Associations among Mental Disorders and Suicidal Behavior: Findings from the WHO World Mental Health Surveys, PLoS Medicine, 2009, pp. 1-17, vol. 6 Issue 8.
Nock, et al., Cross-national prevalence and risk factors for suicidal ideation, plans and attempts, The British Journal of Psychiatry, 2008, pp. 98-105, vol. 192.
Nock, et al., Prevalence, Correlates, and Treatment of Lifetime Suicidal Behavior Among Adolescents, JAMA Psychiatry, Nov. 7, 2013, pp. 300-310, vol. 70 Issue 3.
Noppers, I. et al., "Absence of long-term analgesic effect from a short-term S-ketamine infusion on fibromyalgia pain: A randomized, prospective, double blind, active placebo-controlled trial". European J. of Pain. 2011, 942-49, 15.
Northside Clinic, AUSTRALIA., Ketamine as an Anaesthetic Agent in Electroconvulsive Therapy (ECT), ClinicalTrials.gov, May 20, 2008, Ketamine, NCT00680433.
Northwell Health., Ketamine as an Augmentation Strategy for Electroconvulsive Therapy (ECT) in Depression, ClinicalTrials. gov, Jun. 20, 2013, Ketamine, NCT01881763.
Northwestern University., Postpartum Perineal Pain After Obstetric Anal Sphincter Injuries, ClinicalTrials.gov, Mar. 20, 2018, ketamine, NCT03470675.
O'Connor, et al., Screening for Suicide Risk in Primary Care: A Systematic Evidence Review for the U.S. Preventive Services Task Force, Evidence Synthesis, 2013, pp. 1-126, AHRQ Publication No. 13-05188-EF-1.

(56) References Cited

OTHER PUBLICATIONS

Oishi, S., Food Chem Toxicol., 2002, pp. 1807-1813, 40(12).
Okamoto et al, Rapid Antidepressant Effect of Ketamine Anesthesia During Electroconvulsive Therapy of Treatment-Resistant Depression, Journal of ECT, 2010, pp. 223-227, vol. 26 Issue 3.
Onescu, et al., Rapid and Sustained Reductions in Current Suicidal Ideation Following Repeated Doces of Intravenous Ketamine:, J Clin Psychiatry, 2016, pp. e1-e7.
Opler, et al., Ameliorating treatment-refractory depression with intranasal ketamine: potential NMDA receptoractions in the pain circuitry representing mental anguish, CNS Spectrums, Jan. 26, 2016, pp. 1-12.
Opposition filed during prosecution of corresponding CL Appl No. 2014-2406.
Oshima, et al., Continuous subcutaneous injection of ketamine for cancer pain, Canadian Journal of Anaesthesia, 1990, pp. 385-392, vol. 37 Issue 3.
Ostroff, et al., Antidepressant Effect of Ketamine During ECT, American Journal of Psychiatry, 2005, pp. 1385-1386, vol. 162 Issue 7.
Overall, et al., Overall et al brief psychiatric rating scale, overall et al brief psychiatric rating scale, 2018, pp. 1-6, page number.
Overall, et al., The Brief Psychiatric Rating Scale1, Psychological Reports, Apr. 17, 1962, pp. 799-812, vol. 10.
Pacella, Single-dose Ketamine for the Reduction of Pain and Depression in the Emergency Department, ClinicalTrials.gov, Feb. 16, 2018, Ketamine, NCT03436121.
Papakostas, "L-methylfolate as adjunctive therapy for SSRI-resistant major depression: results of two randomized, double-blind, parallel-sequential trials", Am. J. Psychiatry, 2012, 169(12), 1267-1274.
Papp, et al., Antidepressant activity of non-competitive and competitive NMDA receptor antagonists in a chronic mild stress model of depression, European Journal of Pharmacology, Jun. 21, 1994, pp. 1-7, vol. 263.
Paslakis G et al: "Oral administration of the NMDA receptor antagonist S-ketamine as add-on therapy of depression: a case series.", Pharmacopsychiatry Jan 2010, vol. 43, No. 1, Jan. 2010 (Jan. 2010), pp. 33-35.
Paul et al., Comparison of racemic ketamine and S-ketamine in treatment-resistant major depression: Report of two cases, The World Journal of Biological Psychiatry, 2009, pp. 241-44, vol. 10 Issue 3.
Paule, et al., Behavioral Effects in Primates Ketamine Anesthesia during the first week of life can cause long-lasting cognitive deficits in rhesus monkey, Neurotoxicology and Teratology, 2011, pp. 1-33.
Paulekuhn, "Trends in Active Pharmaceutical Ingredient Salt Selection based on Analysis of the Orange Book Database", J. Med. Chem., 2007, 50, 6665-6672.
Pearson, et al., Intervention Research With Persons at high Risk for Suicidality: Safety and Ethical Considerations, J Clin Psychiatry, 2001, pp. 17-26, vol. 62 Supplementary 25.
Pecina M. et al., "Valence-specific effects of BDNF Val66Met polymorphism on dopaminergic stress and reward processing in humans", J. Neurosci., Apr. 23, 2014, vol. 34(17), pp. 5874-5881.
Peking University First Hospital, Low-dose Ketamine and Postpartum Depression in Patients With Prenatal Depression, ClinicalTrials.gov, Nov. 8, 2017, Ketamine, NCT03336541.
Pennybaker, et al., Symptomatology and Predictors of Antidepressant Efficacy in Extended Responders to a Single Ketamine Infusion, J Affect Disord., Jan. 15, 2015, pp. 1-20, vol. 208.
Per Gisle Djupesland., Nasal drug delivery devices: characteristics and performance in a clinical perspective—a review, Drug Deliv. and Transl. Res, Oct. 18, 2012, pp. 1-21, Page Number.
Pfeiffer, et al., Treatment-Resistant Depression and Risk of Suicide, Suicide and Life-Threatening Behavior, Dec. 26, 2012, pp. 1-10.
Pfenninger, et al., Cognitive Impairment after Small-dose Ketamine Isomers in Comparison to Equianalgesic Racemic Ketamine in Human Volunteers, Anesthesiology, 2002, pp. 357-366, vol. 96 Issue 2.
Pfizer, (S)-(+)-Ketamine Hydrochloride Solution, Material Safety Data Sheet, Nov. 5, 2008, pp. 1-8, Version 1.0.
Phelps et al., Family history of alcohol dependence and initial antidepressant response to an N-methyl-D-aspartate antagonist. Biological psychiatry 65, 2009, pp. 181-184.
Pi_Mylan_Ketamine_HC_Injection, Ketamine Hydrochloride—ketamine hydrochloride injection, solution Mylan Institutional LLC, Pi_Mylan_Ketamine_HClInjection, 2012, 1-16, page number.
Pierre Blier., Exploiting N-Methyl-D-Aspartate Channel Blockade for a Rapid Antidepressant Response in Major Depressive Disorder, Biol Psychiatry, May 30, 2013, pp. 238-239, vol. 74.
Poreh, et al., The BPQ: A Scale for the Assessment of Borderline Personality Based on DSM-IV Criteria, Journal of Personality Disorders, 2006, pp. 247-260, vol. 20 Issue 3.
Posner, et al., Columbia Classification Algorithm of Suicide Assessment (C-CASA): Classification of Suicidal Events in the FDA's Pediatric Suicidal Risk Analysis of Antidepressants, Am J Psychiatry, 2007, pp. 1035-1043, vol. 164.
Posner, et al., The Columbia-Suicide Severity Rating Sclae: Initial Validity and internal Consistency Findings From Three Multisite studies with adolescents and Adults, Am JP sychiatry, 2011, pp. 1266-1277, vol. 168 Issue 12.
Pouya Movahed Rad., Ketamine as an Alternative Treatment to Ect in Major Depressive Disorder, ClinicalTrials.gov, Jan. 20, 2016, Ketamine, NCT02659085.
PRD3253CLPCT_Opposition BriefTranslation, 2014.
Price et al, Effects of Intravenous Ketamine on Explicit and Implicit Measures of Suicidality in Treatment-Resistant Depression, Biol. Psychiatry, 2009, pp. 522-526, vol. 66, Society of Biological Psychiatry.
Price, et al, Effects of Ketamine on Explicit and Implicit Suicidal Cognition: A Randomized Controlled Trial in Treatment-Resistant Depression, Depress Anxiety., 2014, pp. 1-18, vol. 31 Issue 4.
Price, Intravenous Ketamine Plus Neurocognitive Training for Depression, ClinicalTrials.gov, Aug. 2, 2017, Intravenous ketamine, NCT03237286.
Pringle, et al., A Strategic App.roach for Prioritizing Research and Action to Prevent Suicide, Psychiatric Services, 2013, pp. 71-75, vol. 64 Issue 1.
Proescholdt, Brain Res., 2001, 904, 245-251.
Przegalinski, et al., Antidepressant-like Effects of a Partial Agonist at Strychnine-insensitive Glycine Receptors and a competitive NMDA Receptor Antagonist, Neuropharmacology, 1997, pp. 31-37, vol. 36 Issue 1.
Psychiatric University Hospital, Zurich., A Multimodal Neuroimaging Study of Brain Activation Patterns Under Ketamine, ClinicalTrials.gov, Aug. 1, 2018, Ketamine, NCT03609190.
Janicak, et al., Ketamine Treatment for Major Depression, Psychopharm Review, 2011, pp. 89-96, vol. 46 Issue 12.
Janssen Pharmaceutical K.K., A Study to Evaluate the Efficacy, Safety and Tolerability of Fixed Doses of Intranasal Esketamine in Japanese Participants With Treatment Resistant Depression, ClinicalTrials.gov, Sep. 28, 2016, Esketamine, NCT02918318.
Janssen Research & Development, LLC, A Double-blind Study to Assess the Efficacy and Safety of Intranasal Esketamine for the Rapid Reduction of the Symptoms of Major Depressive Disorder, Including Suicidal Ideation, in Participants Who Are Assessed to be at Imminent Risk for Suicide, ClinicalTrials.gov, May 7, 2014, Esketamine, NCT02133001.
Janssen Research & Development, LLC, A double-blind study to assess the efficacy and safety of intranasal esketamine for the rapid reduction of the symptoms of major for the rapid reduction of the symptoms, ClinicalTrials.gov, Jun. 23, 2014, ?, NCT02133001.
Janssen Research & Development, LLC, A Long-term, Safety and Efficacy Study of Intranasal Esketamine in Treatment-resistant Depression (SUSTAIN-2), ClinicalTrials.gov, Jul. 14, 2015, Esketamine, NCT02497287.
Janssen Research & Development, LLC, A Mass Balance Study With a Microtracer Dose of 14C-esketamine in Healthy Male Participants, ClinicalTrials.gov, Feb. 4, 2016, Esketamine, NCT02674295.
Janssen Research & Development, LLC, A Study of Intranasal Esketamine Plus an Oral Antidepressant for Relapse Prevention in

(56) References Cited

OTHER PUBLICATIONS

Adult Participants With Treatment-resistant Depression (SUSTAIN-1), ClinicalTrials.gov, Jul. 10, 2015, Esketamine, NCT02493868.

Janssen Research & Development, LLC, A Study of the Efficacy and Safety of Intranasal Esketamine in the Rapid Reduction of Symptoms of Major Depressive Disorder, in Adult at Imminent Risk for Suicide (Aspire I), ClinicalTrials.gov, Feb. 1, 2017, Esketamine, NCT03039192.

Janssen Research & Development, LLC, A Study of the Efficacy of Intravenous Esketamine in Adult Patients With Treatment-Resistant Depression, ClinicalTrials.gov, Jul. 13, 2012, Esketamine, NCT01640080.

Janssen Research & Development, LLC, A Study to Assess the Effects of Hepatic Impairment on the Pharmacokinetics, Safety, and Tolerability of Intranasally Administered Esketamine, ClinicalTrials.gov, Nov. 20, 2015, Esketamine, NCT02611505.

Janssen Research & Development, LLC, A Study to Evaluate the Absolute Bioavailability of Intranasal and Oral Esketamine and the Effects of Clarithromycin on the Pharmacokinetics of Intranasal Esketamine in Healthy Participants, ClinicalTrials.gov, Jan. 21, 2015, Esketamine, NCT02343289.

Janssen Research & Development, LLC, A Study to Evaluate the Effects of a Single-Dose and Repeat-Administration of Intranasal Esketamine on On-Road Driving in Participants With Major Depressive Disorder (DriveSaFe2), ClinicalTrials.gov, Sep. 29, 2016, Esketamine, NCT02919579.

Janssen Research & Development, LLC, A Study to Evaluate the Efficacy, Safety, and Tolerability of Flexible Doses of Intranasal Esketamine Plus an Oral Antidepressant in Adult Participants With Treatment-resistant Depression (TRANSFORM-2), ClinicalTrials.gov, Apr. 16, 2015, Esketamine, NCT02418585.

Janssen Research & Development, LLC, Pharmacokinetic, Safety, and Tolerability Study of Intranasally Administered Esketamine in Elderly and and Healthy Younger Adult Participants, ClinicalTrials.gov, Jan. 26, 2015, Esketamine, NCT02345148.

Janssen Research & Development, LLC, Study to Evaluate the Efficacy and Safety of 3 Fixed Doses of Intranasal Esketamine in Addition to Comprehensive Standard of Care for the Rapid Reduction of the Symptoms of Major Depressive Disorder, Including Suicidal Ideation . . . , ClinicalTrials.gov, Jun. 14, 2017, Esketamine, NCT03185819.

Janssen Research & Development, LLC., A Long-term Safety Study of Intranasal Esketamine in Treatment-resistant Depression (SUSTAIN-3), ClinicalTrials.gov, May 25, 2016, Esketamine, NCT02782104.

Janssen Research & Development, LLC., A Pharmacokinetic, Safety and Tolerability Study of Esketamine in Healthy Elderly and Adult Participants, ClinicalTrials.gov, May 2, 2014, Esketamine, NCT02129088.

Janssen Research & Development, LLC., A Study of Ketamine in Patients With Treatment-resistant Depression, ClinicalTrials.gov, Jun. 26, 2012, ketamine, NCT01627782.

Janssen Research & Development, LLC., A Study to Assess the Effect of Ticlopidine on the Pharmacokinetics, Safety, and Tolerability of Intranasally Administered Esketamine in Healthy Participants, ClinicalTrials.gov, Oct. 2, 2017, Esketamine, NCT03298906.

Janssen Research & Development, LLC., A Study to Assess the Effects of Renal Impairment on the Pharmacokinetics, Safety, and Tolerability of Intranasally Administered Esketamine, ClinicalTrials.gov, Nov. 17, 2015, Esketamine, NCT02606084.

Janssen Research & Development, LLC., A Study to Assess the Pharmacokinetics of Intranasally Administered Esketamine in Healthy Japanese and Caucasian Volunteers, ClinicalTrials.gov, Nov. 8, 2013, Esketamine, NCT01980303.

Janssen Research & Development, LLC., A Study to Assess the Pharmacokinetics, Safety, and Tolerability of Intranasally Administered Esketamine in Healthy Participants, ClinicalTrials.gov, Jan. 31, 2013, Esketamine, NCT01780259.

Janssen Research & Development, LLC., A Study to Evaluate the Effect of Intranasal Esketamine on Cognitive Functioning in Healthy Subjects, ClinicalTrials.gov, Mar. 21, 2014, Esketamine, NCT02094378.

Janssen Research & Development, LLC., A Study to Evaluate the Effects of Esketamine on Cardiac Repolarization in Healthy Participants, ClinicalTrials.gov, Apr. 14, 2016, Esketamine, NCT02737605.

Janssen Research & Development, LLC., A Study to Evaluate the Efficacy and Safety of Intranasal Esketamine in Addition to Comprehensive Standard of Care for the Rapid . . . , ClinicalTrials.gov, Mar. 31, 2017, Esketamine, NCT03097133.

Janssen Research & Development, LLC., A Study to Evaluate the Efficacy, Pharmacokinetics, Safety and Tolerability of Flexible Doses of Intranasal Esketamine Plus an Oral Antidepressant in Adult Participants With Treatment-resistant Depression, ClinicalTrials.gov, Feb. 15, 2018, Esketamine, NCT03434041.

Janssen Research & Development, LLC., A Study to Evaluate the Efficacy, Safety, and Tolerability of Fixed Doses of Intranasal Esketamine Plus an Oral Antidepressant in Adult Participants With Treatment-resistant Depression (TRANSFORM-1), ClinicalTrials.gov, Apr. 15, 2015, Esketamine, NCT02417064.

Janssen Research & Development, LLC., A Study to Evaluate the Efficacy, Safety, and Tolerability of Intranasal Esketamine Plus an Oral Antidepressant in Elderly Participants With Treatment-resistant Depression (TRANSFORM-3), ClinicalTrials.gov, Apr. 21, 2015, Esketamine, NCT02422186.

Janssen Research & Development, LLC., A Study to Evaluate the Pharmacokinetics of Intranasal Esketamine Administered With and Without a Nasal Guide on the Intranasal Device, ClinicalTrials.gov, Feb. 12, 2014, Esketamine, NCT02060929.

Janssen Research & Development, LLC., A Study to Evaluate the Safety and Efficacy of Intranasal Esketamine in Treatmentresistant Depression (SYNAPSE), ClinicalTrials.gov, Dec. 3, 2013, Esketamine, NCT01998958.

Janssen Research & Development, LLC., A Study to Investigate Evoked Potentials as Markers of Ketamine-induced Cortical Plasticity in Patients With Major Depressive Disorder, ClinicalTrials.gov, Oct. 8, 2013, Ketamine, NCT01957410.

Janssen Research & Development, LLC., Crossover Study to Evaluate the Abuse Potential of Intranasal Esketamine Compared to Racemic Intravenous Ketamine in Nondependent, Recreational Drug Users, ClinicalTrials.gov, Feb. 15, 2016, Esketamine, NCT02682225.

Janssen Research & Development, LLC., Pharmacokinetic Study of Intranasal Esketamine and Its Effects on the Pharmacokinetics of Orally-Administered Midazolam and Bupropion in Healthy Participants, ClinicalTrials.gov, Oct. 5, 2015, Esketamine, NCT02568176.

Janssen Research & Development, LLC., Study to Assess the Effects of Allergic Rhinitis and Co-administration of Mometasone or Oxymetazoline on the Pharmacokinetics, Safety, and Tolerability of Intranasal Esketamine, ClinicalTrials.gov, Jun. 3, 2014, Esketamine, NCT02154334.

Janssen Research & Development, LLC., Study to Assess the Effects of Esketamine on Safety of On-road Driving in Healthy Participants (DRiVESaFe), ClinicalTrials.gov, Aug. 28, 2014, Esketamine, NCT02228239.

Janssen Research & Development, LLC., The Effect of Minocycline on Relapse After Successful Intravenous Ketamine/Minocyclineinduced Symptoms Response in Subjects With Depression, ClinicalTrials.gov, Mar. 12, 2013, Ketamine, NCT01809340.

Jason Mcmullan., Intranasal Ketamine as an Adjunct to Fentanyl for the Prehospital Treatment of Acute Traumatic Pain, ClinicalTrials.gov, Aug. 15, 2016, Ketamine, NCT02866071.

Javelin Pharmaceuticals, Safety and Efficacy of Intranasal Ketamine for the Treatment of Postoperative Dental Pain, ClinicalTrials.gov, Jun. 20, 2007, Ketamine, NCT00488787.

Javelin Pharmaceuticals., Absolute Bioavailability and Nasopharyngeal Absorption of Intranasal Ketamine, ClinicalTrials.gov, Aug. 23, 2007, ketamine, NCT00520169.

Javelin Pharmaceuticals., Assessing the Effects of a Nasal Corticosteroid on PMI-150 (Intranasal Ketamine), ClinicalTrials.gov, Apr. 21, 2008, Ketamine, NCT00662883.

Javelin Pharmaceuticals., Determination of Drug Interactions of Certain Nasal Medications With Intranasal Ketamine, ClinicalTrials.gov, Aug. 23, 2007, Ketamine, NCT00520104.

Javelin Pharmaceuticals., Multiple Dose Pharmacokinetics of Intranasal Ketamine, ClinicalTrials.gov, Aug. 23, 2007, Ketamine, NCT00519987.

(56) References Cited

OTHER PUBLICATIONS

Jevtovic-Todorovic, Journal of Cerebral Blood Flow and Metabolism, 1997, 17, 168-174.
Jick, et al., Antidepressants and the Risk of Suicidal Behaviors, JAMA, Jul. 21, 2004, pp. 338-343, vol. 292 Issue 3.
Joakim Johansson et al: "Prehospital analgesia using nasal administration of S-ketamine—a case se", Scandinavian Journal of Trauma, Resuscitation and Emergency Medicine, Biomed Central Ltd, London UK, vol. 21, No. 1, May 14, 2013 (May 14, 2013), p. 38, XP021151671, ISSN: 1757-7241, DOI: 10.1186/1757-7241-21-38 see materials.
Johansson J. et al., "Prehospital analgesia using nasal administration of S-ketamine—a case series", Scandinavian Journal of Trauma, Resuscitation and Emergency Medicine, Biomed Central Ltd, London UK, vol. 21, No. 38, May 14, 2013 (May 14, 2013), pp. 1-4.
Johnson & Johnson Pharmaceutical Research & Development, Ll.C.., The Effect of Ketamine on Attentiveness, ClinicalTrials.gov, Jul. 19, 2010, Ketamine, NCT01165294.
Jokinen, et al., Karolinska Interpersonal Violence Scale Predicts Suicide in Siicide Attemptsers, J Clin Psychiatry, Mar. 16, 2010, pp. 1025-1032, vol. 71 Issue 8.
Jonkman, et al., Pharmacokinetics and Bioavailability of Inhaled Esketamine in Healthy Volunteers., Anesthesiology, 2017, pp. 675-683, vol. 127 Issue 4.
JP63002932 A English Translation, Jan. 1988, Translated Jan. 30, 2015.
Duman, et al., Synaptic plasticity and mood disorders, Molecular Psychiatry, 2002, pp. 1-11, vol. 7 Issue 1.
Duncan, et al., Baseline delta sleep ratio predicts acute ketamine mood response in major depressive disorder, Journal of Affective Disorders, Aug. 5, 2012, pp. 115-119, vol. 145.
Elie Dolgin., The Ultimate Endpoint, Nature Medicine, 2012, pp. 190-194, vol. 18 Issue 2.
Ellioti, et al., N-Methyl-D-Aspartate (NMDA) Receptors, Mu and Kapp.a Opioid Tolerance, and Perspectives on New Analgesic Drug Development, Neuropsychopharmacology., May 3, 1995, pp. 347-356, vol. 13 Issue 4.
Emory University., Heart Rate Variability in Depression, ClinicalTrials.gov, Aug. 18, 2015, Depressive Disorder, NCT02525978.
Emory University., Intranasal (NAS) Ketamine for Cancer Pain, ClinicalTrials.gov, May 10, 2017, Ketamine, NCT03146806.
Entsuah, et al., Response and Remission Rates in Different Subpopulations With Major Depressive Disorder Administered Venlafaxine, Selective Serotonin Reuptake Inhibitors, or Placebo, J Clin Psychiatry, 2001, pp. 869-877, vol. 62 Issue 11.
Erasme University Hospital, Respiratory Depression During an Analgosedation Combining Remifentanil and Ketamine in TCI for Oocyte Retrieval, ClinicalTrials.gov, Mar. 8, 2018, ketamine, NCT03458143.
Essentia Health., Ketamine Frequency Treatment for Major Depressive Disorder, ClinicalTrials.gov, Mar. 28, 2008, Ketamine, NCT00646087.
Fan, et al., Ketamine rapidly relieves acute suicidal ideation in cancer patients: a randomized controlled clinical trial, Oncotarget, Dec. 1, 2016, pp. 2356-2360, vol. 8 Issue 2.
Fan, et al., Profiling the psychotic, depressive and anxiety symptoms in chronic ketamine users, Psychiatry Research, Jan. 14, 2016, pp. 311-315, vol. 237.
Fastner, et al., Intravenous S-Ketamine Does Not Inhibit Alveolar Fluid Clearance in a Septic Rat Model, PLOS ONE, Nov. 11, 2014, pp. 1-9, vol. 9 Issue 11.
Fava, "A double-blind, placebo-controlled study of aripiprazole adjunctive to antidepressant therapy among depressed outpatients with inadequate response to prior antidepressant therapy (Adapt-A-Study", Psychother. Psychosom, 2012, 81(2), 87-97.
Fava, "The problem of the placebo response in clinical trials for psychiatric disorders: culprits, possible remedies, and a novel study design approach", Psychother. Psychosom, 2003, 72(3), 115-127.
Fava., Diagnosis and Definition of Treatment-Resistant Depression, Biol Psychiatry, Feb. 21, 2003, pp. 649-659, vol. 53.

Feifel, et al., Low-dose ketamine for treatment resistant depression in an academic clinical practice setting, Journal of Affective Disorders, Jun. 20, 2017, pp. 283-288, vol. 221.
First Affiliated Hospital of Chongqing Medical University., Effect of Subanesthetic Dose of Ketamine Combined With Propofol on Cognitive Function in Depressive Patients Undergoing Electroconvulsive Therapy, ClinicalTrials.gov, Dec. 2, 2014, ketamine, NCT02305394.
Fondation Lenval., Intranasal Ketamine and Fracture Reduction in Pediatric Emergencies (KETAPED) (Ketaped), ClinicalTrials.gov, May 16, 2018, Ketamine, NCT03525821.
Ford, et al., Benzodiazepines may reduce the effectiveness of ketamine in the treatment of depression, Australian & New Zealand Journal of Psychiatry, 2015, pp. 1-1, page number.
Frank, et al., Conceptualization and Rationale for Consensus Definitions of Terms in Major Depressive Disorder, Arch Gen Psychiatry, 1991, pp. 851-855, vol. 48.
Friedberg, et al., Hypnosis First, Then Dissociation, Anesth Analg, 2003, pp. 913-914, vol. 96.
Galvez, et al., "Long-Lasting Effects of a Single Subcutaneous Dose of Ketamine for Treating Melancholic Depression: A Case Report", Biol Psychiatry, 2014, pp. e1-e2, vol. 76.
Galvez, et al., Repeated intranasal Ketamine for treatment-resistant depression-the way to go? Results from a pilot randomised controlled trail, Journal of Psychopharmacology, 2018, pp. 1-11, Page Number.
Garcia, et al., Olfactory deposition of inhaled nanoparticles in humans, Inhalation Toxicology, Jul. 21, 2015, pp. 394-403, vol. 27 Issue 8.
GenBank_AC099753, *Homo sapiens* chromosome 3 clone RP11-466A13, complete sequence. Mar. 20, 2002, [online]. [Retrieved on Oct. 1, 2015]. Retrieved from the Internet: <URL: http://www.ncbi.nlm.nih.gov/nuccore/19551144/> PDF file: p. 1-40. p. 1, Definition; p. 3, Origin, p. 27, the nucleotide sequence between 113924-112924, especially the nucleotides between 113444-113405; and the nucleotide at the position of 113424.
George, et al., Pilot Randomized Controlled Trial of Titrated Subcutaneous Ketamine in Older Patients with Treatment-Resistant Depression, Am J Geriatr Psychiatry, 2017, pp. 1-11.
George, Is There Really Nothing New Under the Sun? Is Low-Dose Ketamine a Fast-Acting Antidepressant Simply Because It Is an Opioid?, ajp.psychiatryonline.org, Jul. 10, 2018, pp. 1-2.
George., Is There Really Nothing New Under the Sun? Is Low-Dose Ketamine a Fast-Acting Antidepressant Simply Because It Is an Opioid?, ajp.psychiatryonline.org, Jul. 10, 2018, pp. 1-2, page Number.
Ghasemi, et al., "Rapid antidepressant effects of repeated doses of ketamine compared with electroconvulsive therapy in hospitalized patients with major depressive disorder", Psychiatry Research, Dec. 13, 2014, vol. 215, 355-361.
Gizurarson, Acta Pharm. Nord., 1990, 2(2), 105-122.
Gliatio, et al., Evaluation and Treatment of Patients with Suicidal Ideation, American Family Physician,Mar. 15, 1999, pp. 1500-1506, vol. 59 Issue 6.
Glue, et al: Dose- and Exposure-Response to Ketamine in Depression, Biol Psychiatry 2011; 70: e9-e10.
Gocmen et al., In Vitro Investigation of the Antibacterial Effect of Ketamine; Upsala J Med Sci 113 (1) 2008: pp. 39-46.
Gomes,et al., Neurotoxicity of Subarachnoid Preservative—Frees(+)-Ketamine in Dogs, Pain Physician, 2011, pp. 83-90, vol. 14.
Gosek, et al., Effectiveness of ketamine in depressed patients resistant to ECT or rTMS therapy, Psychiatr. Pol, 2014, pp. 49-58, vol. 48 Issue 1.
Green, Lab. Anim, 1981, 15, 163-170.
Guangzhou Women and Children's Medical Center,"Intranasal Ketamine with Dexmedetomidine for the Treatment of Children with Autism Spectrum Disorder" ClinicalTrials.gov., Feb. 15, 2018, Ketamine, NCT03434366, 7 pgs.
Gurnani, et al., "Role of Ketamine in Severe Depression with suicidal ideation—Insights from a Case Study", Asian Journal of Psychiatry, Apr. 12, 2017, vol. 29, 112-113.
Gutzke, et al., Cardiac Transplantation: A Prospective Comparsion of Ketamine and sufentanil for Anesthetic Induction, Journal of Cardiothoracic Anesthesia, 1989, pp. 389-395, vol. 3 Issue 4.

(56) References Cited

OTHER PUBLICATIONS

Hamilton, Hamilton Depression Rating Scale (HAM-D), M. Journal of Neurology, Neurosurgery, and Psychiatry, 1960, pp. 56-62, vol. 23.
Hamilton, Ketamine, A Promising Depression Treatment, Seems to Act Like an Opioid,, www.npr.org, Aug. 29, 2018, pp. 1-8, NA.
Harihar, et al., Intramuscular ketamine in acute depression: a report on two cases, Indian Journal of Psychiatry, 2013, pp. 186-188, vol. 55 Issue 2.
Hassamal, et al., Augmentation Therapy With Serial Intravenous Ketamine Over 18 Months in a Patient With Treatment Resistant Depression, Clin Neuropharm, 2015, pp. 212-216, vol. 38 Issue 5.
Healthcare Quality Report., Highlights From the 2012 National Healthcare Quality and Disparities Reports, Healthcare Quality Report, 2013, pp. 1-212, AHRQ Publication No. 13-0002.
Hedlund, et al., The Hamilton Rating Scale for Depression A Comprehensive Review, Journal of Operational Psychiatry, 1979, pp. 150-165, vol. 10 Issue 2.
Helsinki University., Psilocybin and Depression (Psilo101), ClinicalTrials.gov, Dec. 21, 2017, ketamine, NCT03380442.
Hijazi et al., Stability of Ketamine and Its Metabolites Norketamine and Dehydronorketamine in Human Biological Samples, Clinical Chemistry 47(9):1713-1715, 2001.
Ho, C.Y. et al., Am J Rhinol., 2008, pp. 125-129, 22(2).
Hoffman, J. Anesthesiology, 1992, 76(5), 755-762.
Medical University of Vienna., Positron Emission Tomography Assessment of Ketamine Binding of the Serotonin Transporter, ClinicalTrials.gov, Mar. 23, 2016, Ketamine, NCT02717052.
Mellon, et al., Blockade of NMDA Receptors and Apoptotic Neurodegeneratin in the Developing Brain, Science, Mar. 10, 2011, pp. 70-74, vol. 283.
Mellon, et al., Use of Anesthetic Agents in Neonates and Young Children, Anesth Analg, 2007, pp. 509-520, vol. 104.
Mental Health Serv Admin., Results From the 2013 National Survey on Drug Use and Health: Mental Health Detailed Tables, Mental Health Serv Admin, Nov. 14, 2014, pp. 1-577, page number.
Messer, et al., The Use of a Series of Ketamine Infusions in Two Patients With Treatment-Resistant Depression, J Neuropsychiatry Clin Neurosci, 2010, pp. 442-444, vol. 22 Issue 4.
Meuronen, MD., "Intranasal Esketamine and Fentanyl for Pain in Minor Trauma", ClinicalTrials.gov, Feb. 5, 2018, Esketamine, NCT03421275.
Meyer, et al., Suicidality and Risk of Suicide-Definition, Drug Safety Concerns, and a Necessary Target for Drug Development: A brief Report, J Clin Psychiatry, Jul. 13, 2010, pp. e1-e7.
Millennium Pharmaceuticals, Inc.., Efficacy and Safety of TAK-653 in Treatment-Resistant Depression, ClinicalTrials.gov, Oct. 18, 2017, TAK-653, NCT03312894.
Minneapolis Veterans Affairs Medical Center., Ketamine Infusions for PTSD and Treatment-Resistant Depression, ClinicalTrials.gov, Oct. 16, 2015, Ketamine, NCT02577250.
Moaddel, et al., D-serine plasma concentration is a potential biomarker of (R,S)-ketamine antidepressant response in subjects with treatment-resistant depression, Psychopharmacology, Jul. 24, 2014, pp. 399-409, vol. 232.
Moharil, et al., Nasal Dosage Forms and Devices for Intranasal Drug Delivery, World Journal of Pharmacy and Pharmaceutical Sciences, Apr. 5, 2014, pp. 554-571, vol. 3 Issue 4.
Molero, et al., Antidepressant Efficacy and Tolerability of Ketamine and Esketamine: A Critical Review, CNS Drugs, May 7, 2018, pp. 411-420, vol. 32.
Montgomery, "A new depression scale designed to be sensitive to change", Br. J. Psychiatry, 1979, 134, 382-389.
Moore, et al., A comparsion between propofol and thiopentone as induction agents in obstetric anaesthesia, Anaesthesia, Feb. 27, 1989, pp. 753-757, vol. 44.
Moran, et al., The natural history of self-harm from adolescence to young adulthood: a population-based cohort study, Lancet, Nov. 17, 2011, pp. 236-243, vol. 379.
Morrison, Effect of intranasal esketamine on cognitive functioning in healthy participants: a randomized, double-blind, placebo-controlled study, Psychopharmacology, Feb. 1, 2018, pp. 1107-1119, vol. 235.
Moryl, et al., Potential Antidepressive Properties of Amantadine, Memantine and Bifemelane, Pharmacology & Toxicology, Feb. 3, 1993, pp. 394-397, vol. 72.
Mundt, et al., Risk of Prospective Suicidal Behavior Reports among Psychiatric and non-Psychiatric Patients using Lifetime Reports at Baseline, Healthcare Technology Systems, Feb. 19, 2013, pp. 1-1, Poster.
Murray, et al., Global mortality, disability, and the contribution of risk factors:Global Burden of Disease Study, The Lancet, May 17, 1997, pp. 1436-1442, vol. 349.
Murrough et al.; "Dose- and Exposure-Response to Ketamine in Depression", Biological Psychiatry, vol. 70, No. 4, Aug. 1, 2011, pp. e11-e12, XP055610008, NY, NY; US.
Murrough, et al., Antidepressant Efficacy of Ketamine in Treatment-Resistant Major Depression: A Two-Site Randomized Controlled Trial, Am J Psychiatry, Oct. 1, 2013, pp. 1134-1142, vol. 170 Issue 10.
Murrough, et al., Ketamine for rapid reduction of suicidal ideation: a randomized controlled trial, Psychological Medicine, Jul. 14, 2015, pp. 1-10.
Murrough, et al., Neurocognitive Effects of Ketamine and Association with Antidepressant Response in Individuals with Treatment-Resistant Depression: A Randomized Controlled Trial, Neuropsychopharmacology, Oct. 18, 2014, pp. 1084-1090, vol. 40.
Murrough, et al., Rapid and Longer-Term Antidepressant Effects of Repeated. Ketamine Infusions in Treatment-Resistant Major Depression, Biol Psychiatry, Aug. 15, 2015, pp. 250-256, vol. 74 Issue 4.
Murrough, Ketamine for Suicidal Ideation, ClinicalTrials.gov, Jan. 10, 2012, Ketamine, NCT01507181.
Murrough., Continuation Ketamine in Major Depression, ClinicalTrials.gov, Oct. 25, 2007, Ketamine, NCT00548964.
Murrough., Intranasal Ketamine in Treatment-Resistant Depression, ClinicalTrials.gov, Feb. 25, 2011, Ketamine, NCT01304147.
Murrough., Use of Ketamine to Enhance Electroconvulsive Therapy (ECT) in Depression, ClinicalTrials. gov, Mar. 7, 2011, Ketamine, NCT01309581.
Narita, et al., Role of the NMDA receptor subunit in the expression of the discriminative stimulus effect induced by ketamine, European Journal of Pharmacology, May 29, 2001, pp. 41-46, vol. 423.
Nasal Powder, Package leaflet: Information for the User, Nasal Powder, 2017, pp. 1-6.
National Institute of Mental Health (NIMH), Antidepressant Effects of the Glycine Receptor Antagonist AV-101 (4-chlorokynurenine) in Major Depressive Disorder, ClinicalTrials.gov, Jun. 29, 2015, AV 101 (4-Chlorokynurenine), NCT02484456.
National Institute of Mental Health (NIMH), Neurobiology of Suicide, ClinicalTrials.gov, Sep. 9, 2015, ketamine, NCT02543983.
National Institute of Mental Health (NIMH), The Neurophysiological Effects of Intravenous Alcohol as Potential Biomarkers of Ketamine's Rapid Antidepressant Effects in Major Depressive Disorder, ClinicalTrials.gov, Apr. 24, 2014, Ketamine, NCT02122562.
National Institute of Mental Health (NIMH)., Neuropharmacologic Imaging and Biomarker Assessments of Response to Acute and Repeated-Dosed Ketamine Infusions in Major Depressive Disorder, ClinicalTrials.gov, Feb. 27, 2017, Ketamine, NCT03065335.
National Institute of Mental Health (NIMH)., Rapid Antidepressant Effects of Ketamine in Major Depression, ClinicalTrials.gov, Aug. 2, 2004, Ketamine, NCT00088699.
National Institute of Neurology and Neurosurgery, Mexico., Clinical Trial of the Use of Ketamine in Treatment Resistant Depression, ClinicalTrials.gov, Nov. 20, 2015, Ketamine, NCT02610712.
National Strategy for Suicide Prevention, Goals and Objectives for Action, National Strategy for Suicide Prevention, 2012, pp. 1-184, page number.
Nationwide Children's Hospital., An Open Prospective Trial of IV Ketamine in Suicidal Adolescents, ClinicalTrials.gov, Jan. 29, 2014, Ketamine, NCT02048423.

(56) References Cited

OTHER PUBLICATIONS

Neurorx, Inc., NRX-101 for Maintenance of Remission From Severe Bipolar Depression in Patients With Suicidal Ideation (SBD-ASIB), ClinicalTrials.gov, Jan. 10, 2018, NRX-101, NCT03396068.
Neurorx, Inc., NRX100 vs. Placebo for Rapid Stabilization of Acute Suicidal Ideation and Behavior in Bipolar Depression (SevereBD), ClinicalTrials.gov, Jan. 11, 2018, ketamine, NCT03396601.
Neurorx, Inc., NRX101 Glx Biomarker Validation Study (NRX-GLX), ClinicalTrials.gov, Jan. 18, 2018, NRX-101, NCT03402152.
Neurorx, Inc., Sequential Therapy for the Treatment of Severe Bipolar Depression. (STABIL-B), ClinicalTrials.gov, Nov. 28, 2016, Ketamine, NCT02974010.
New York State Psychiatric Institute, NMDA Antagonists in Bipolar Depression, ClinicalTrials.gov, Apr. 17, 2013, ketamine, NCT01833897.
New York State Psychiatric Institute., Investigation of the NMDA Antagonist Ketamine as a Treatment for Tinnitus, ClinicalTrials.gov, Nov. 8, 2017, Ketamine Hydrochloride in saline, NCT03336398.
New York State Psychiatric Institute., Ketamine for Suicidality in Bipolar Depression, ClinicalTrials.gov, Sep. 17, 2013, Ketamine, NCT01944293.
New York State Psychiatric Institute., Ketamine in the Treatment of Suicidal Depression, ClinicalTrials.gov, Oct. 4, 2012, Ketamine, NCT01700829.
New York University School of Medicine, Ketamine as a Rapidly-Acting Antidepressant in Depressed Emergency Department Patients, ClinicalTrials.gov, Apr. 8, 2014, Ketamine, NCT02106325.
New York University School of Medicine, Study on the Use of Low Dose Ketamine After Gastric Bypass and Gastrectomy, ClinicalTrials.gov, May 22, 2015, Ketamine, NCT02452060.
Newcomer, et al., Ketamine-Induced NMDA Receptor Hypofunction as a Model of Memory Impairment and Psychosis, Neuropsychopharmacology, 1999, pp. 106-118, vol. 20 Issue 2.
Niciu, et al., Ketamine's Antidepressant Efficacy is Extended for at Least Four Weeks in Subjects with a Family History of an Alcohol Use Disorder, International Journal of Neuropsychopharmacology, Jul. 2, 2014, pp. 1-7, Page Number.
Brent, et al., Association of FKBP5 Polymorphisms With Suicidal Events in the Treatment of Resistant Depression in Adolescents (TORDIA) Study, Am J Psychiatry, 2010, pp. 190-197, vol. 167 Issue 2.
Brent, et al., Switching to Another SSRI or to Venlafaxine With or Without Cognitive Behavioral Therapy for Adolescents With SSRI-Resistant Depression the Tordia Randomized Controlled Trial, (Reprinted) JAMA, Feb. 27, 2008, pp. 901-913, vol. 299 Issue 8.
Brent, et al., The Treatment of Adolescent Suicide Attempters Study (TASA): Predictors of Suicidal Events in an Open Treatment Trial, J. Am. Acad. Child Adolesc. Psychiatry, 2009, pp. 987-996, vol. 48 Issue 10.
Brent, et al., Treatment-Resistant Depression in Adolescents: Recognition and Management, Child Adolesc Psychiatric Clin N Am, 2006, pp. 1015-1034, vol. 15.
Bretz, "Combining multiple comparisons and modeling techniques in dose-response studies", Biometrics, 2005, 61, 738-748.
Bridge, et al., Clinical Response and Risk for Reported Suicidal Ideation and Suicide Attempts in Pediatric Antidepressant Treatment A Meta-analysis of Randomized Controlled Trials, (Reprinted) JAMA, Apr. 18, 2007, pp. 1683-1696, vol. 297 Issue 15.
Bridge, et al., Placebo Response in Randomized Controlled Trials of Antidepressants for Pediatric Major Depressive Disorder, Am J Psychiatry, 2009, pp. 42-49, vol. 166.
Bromet, et al., Cross-national epidemiology of DSM-IV major depressive episode, BMC Medicine, 2011, pp. 1-16, vol. 9 Issue 90.
Brooke Army Medical Center, "THINK Trial: Treatment of Headache With IntraNasal Ketamine: A Randomized Controlled Trial Evaluating the Efficacy of Intranasal Ketamine Versus Standard Therapy in the Management of Primary Headache Syndromes in the Emergency Department" (Think), ClinicalTrials.gov, Mar. 16, 2017, Ketamine, NCT03081416.
Brooke Army Medical Center, Intranasal Ketamine for Anxiolysis in Pediatric Emergency Department Patients, ClinicalTrials.gov, Feb. 6, 2017, Ketamine, NCT03043430.
Brooke Army Medical Center., Ketamine for Acute Suicidal Ideation in the Emergency Department: Randomized Controlled Trial (LOK-Si), ClinicalTrials.gov, Jul. 8, 2013, Ketamine, NCT01892995.
Brown, et al., Cognitive Therapy for the Prevention of Suicide Attempts, JAMA, Aug. 3, 2005, pp. 563-570, vol. 294 Issue 5.
Brown, et al., The role of randomized trials in testing interventions for the prevention of youth suicide, International Review of Psychiatry, 2007, pp. 1-15, vol. 19 Issue 6.
Brown, Ph.D., "A Review of Suicide Assessment Measures for Intervention Research with Adults and Older Adults, Suicide Assessment", NA, 57 pgs.
Brown, Ph.D., A Review of Suicide Assessment Measures for Intervention Research with Adults and Older Adults, Suicide Assessment, NA, pp. 1-57, page number.
Busch, et al., Clinical Correlates of Inpatient Sucide, J Clin Psychiatry, 2003, pp. 14-19, vol. 64.
Byrd, et al., Behavioral effects of phencyclidine and ketamine alone and in combination with other drugs, European Journal of Pharamacology, Sep. 29, 1987, pp. 331-341, vol. 144.
Calabrese, et al., A Double-Blind Placebo-Controlled Study of Lamotrigine Monotherapy in Outpatients With Bipolar I Depression, J Clin Psychiatry, 1999, pp. 79-88, vol. 60 Issue 2.
Callahan, et al., EvidenceMap of Prevention and Treatment Interventions for Depression in Young People, Hindawi Publishing Corporation Depression Research and Treatment Volume, Dec. 30. 2011, pp. 1-12, Article ID 820735.
Cameroon Baptist Convention Health., Sub-dissociative Intranasal Ketamine for Pediatric Sickle Cell Pain Crises, ClinicalTrials.gov, Oct. 12, 2015, Ketamine, NCT02573714.
Canuso, "Efficacy and Safety of intranasal Esketamine for the Rapid Reduction of Symptoms of Depression and Suicidality in Patients at Imminent Risk for Suicide: Results of a Double-Blind, Randomized Placebo-Controlled Study", Am. J. Psych., 2018, 1-11.
Canuso, et al., Design of Phase 3 Randomized Studies of Intranasal Esketamine to Treat Major Depressive Disorder Symptoms.., European Symposium on Suicide & Suicidal Behavior (ESSSB), 2018, pp. 1-1.
Carlson, et al., Neural Correlates of Rapid Antidepressant Response to Ketamine in Treatment-Resistant Unipolar Depression: A Preliminary Positron Emission Tomography Study, Biol Psychiatry, Feb. 1, 2013, pp. 1213-1221, vol. 73.
Carolinas Healthcare System, IN Sub-Dissociative Ketamine vs IN Fentanyl, ClinicalTrials.gov, Aug. 13, 2015, Ketamine. NCT02521415.
Carr, et al., Safety and efficacy of intranasal ketamine for the treatment of breakthrough pain in patients with chronic pain: a randomized, double-blind, placebo-controlled, crossover study, Pain, 2004, pp. 17-27, vol. 108.
Caspi, et al., "Influence of Life Stress on Depression: Moderation by a Polymorphism in the 5-HTT Gene", Science, Jul. 18, 2003, vol. 301, 986-689.
Cavanagh, et al., Psychological autopsy studies of suicide: a systematic review, Psychological Medicine, 2003, pp. 395-405, vol. 33.
Cedars-Sinai Medical Center., Ketamine for Preventing Depression in Patients Undergoing Treatment for Pancreatic or Head and Neck Cancers, ClinicalTrials.gov, May 13, 2015, Ketamine, NCT02442739.
Celon Pharma SA., Safety and Pharmacokinetic Study of Inhaled Esketamine in Healthy Volunteers, Clinical Trials. gov, Jan. 23, 2018, Esketamine, NCT03407872.
Centre Hospitalier Universitaire De Ntmes., Effects of Ketamine in the Acute Phase of Suicidal Ideation (KETIS), ClinicalTrials.gov, Nov. 24, 2014, Ketamine, NCT02299440.
Chambers, et al., Developmental Neurocircuitry of Motivation in Adolescence: A Critical Period of Addiction Vulnerability, Am J Psychiatry, 2003, pp. 1041-1052, vol. 160 Issue 6.
Chang, et al, Metabolic Disposition on Tritium-Labeled Ketamine (KETALAR); c1-581 in Normal Human Subjects, Clinical Pharmacology, 1970, pp. 597-597.
Chang, et al., Major Depressive Disorder Induced by Chronic Ketamine Abuse: A Case Report, Primary Care Companion CNS Disorders, Jun. 23, 2016, pp. 1-3, vol. 18 Issue 3.

(56) References Cited

OTHER PUBLICATIONS

Chang, et al., Metabolic Disposition on Tritium-Labelled Ketamine (KETALAR); c1-581 in Normal Human Subjects, Clinical Pharmacology, 1970, pp. 597-597, page number.
Chang, et al., The Depressed Patient and Suicidal Patient in the Emergency Department: Evidence-Based Management and Treatment Strategies, EB Medicine, Sep. 1, 2011, pp. 1-24, vol. 13 Issue 9.
Chen, "A sequential enriched design for target patient population in psychiatric clinical trails", Stat. Med., 2014, 33(17) 2953-2967.
Chen, "Evaluation of performance of some enrichment designs dealing with high placebo response in psychiatric clinical trials", Contemp, Clin. Trials, 2011, 32(4), 592-604.
Chen, et al., Determination of ketamine and metabolites in urine by liquid chromatography-mass spectrometry, Talanta, Jan. 16, 2007, pp. 1217-1222, vol. 72.
Chen, et al., Effect of Low Dose of Ketamine on LearningMemory Function in Patients Undergoing Electroconvulsive Therapy—A Randomized, Double-Blind, Controlled Clinical Study, Journal of ECT •, 2016, pp. 1-7, Page Number.
Chen, et al., High prevalence of major depression among treatment-seeking ketamine-dependent patients, Abstracts/ Drug and Alcohol Dependence, 2017, pp. e39-e40, vol. 171.
Cheung, et al., Review of the efficacy and safety of antidepressants in youth depression, Journal of Child Psychology and Psychiatry, 2005, pp. 735-754, vol. 46 Issue 7.
Cheung, et al., The use of antidepressants to treat depression in children and adolescents, Jan. 17, 2006, pp. 193-200, vol. 174 Issue 2.
Chi, "On clinical trials with a high placebo rate. Contemporary Clinical Trials Communications", 2016, 2, 34-53.
Children's Hospital Medical Center, Cincinnati., Pain Reduction With Intranasal Medications for Extremity Injuries (PRIME), ClinicalTrials.gov, May 20, 2016, ketamine, NCT02778880.
Chong, et al., Development of a Sublingual/Oral Formulation of Ketamine for Use in Neuropathic Pain Preliminary Findings from a Three-Way Randomized, Crossover Study, Clin Drug Invest, 2009, pp. 317-324, vol. 5.
Chu, et al., A Tool for the Culturally Competent Assessment of Suicide: The Cultural Assessment of Risk for Suicide (CARS) Measure, Psychological Assessment, Jan. 28, 2013, pp. 1-12.
Cipriani, et al., Lithium in the Prevention of Suicidal Behavior and All-Cause Mortality in Patients With Mood Disorders: A Systematic Review of Randomized Trials, Am J Psychiatry, 2005, pp. 1805-1819, vol. 162 Issue 10.
Cipriani, et al., Lithium in the prevention of suicide in mood disorders: updated systematic review and meta-analysis, BMJ, Jun. 27, 2013, pp. 1-13, vol. 346.
Clancy, et al., Translating Developmental Time Across Mammalian Species, Neuroscience, Apr. 11, 2011, pp. 7-17, vol. 105 Issue 1. Loss, Brain Research, 2012, 1474, 110-117.
Louon, et al., Sedation with nasal Ketamine and midazolam for cryotherapy in retinopathy of prematurity, British Journal of Ophthalmology, Mar. 17, 1993, pp. 529-530, vol. 77.
Lu, et al., Intravenous ketamine for treatment-refractory depression in medically complex geriatric patients, Am J Geriatr Psychiatry, 2013, pp. S130-S130, Poster No. NR 06.
Luckenbaugh, et al., Do the dissociative side effects of ketamine mediate its antidepressant effects?, Journal of Affective Disorders, Feb. 18, 2014, pp. 56-61, vol. 159.
Lund University., Racemic Ketamine Versus S-ketamine With Arterial Spin Labeling (ASL)-MRI in Healthy Volunteers, ClinicalTrials.gov, Jan. 10, 2012, S-ketamine, NCT01506921.
Malcolm, et al., Efficacy and Safety of Intravenous Low-Dose Ketamine for Treatment of Refractory Depression in a Naturalistic Cohort, Abstract of Malcolm., 2016, pp. 1-2, Poster.
Maler, et al., Memantine inhibits ethanol-induced NMDA receptor up-regulation in rat hippocampal neurons, Brain Research, Jul. 11, 2005, pp. 156-162, vol. 1052.
Manji, et al., Enhancing Neuronal Plasticity and Cellular Resilience to Develop Novel, Improved Therapeutics for Difficult-to-Treat Depression, Biol. Psychiatry, Jan. 23, 2003, pp. 707-742, vol. 53.
Marangell, et al., Effects of Intrathecal Thyrotropin-Releasing Hormone (protirelin) in Refractory Depreesed Patients, Arch Gen Psychiatry, 1997, pp. 214-222, vol. 54.
Marhofer, P., et al, "S(+)-ketamine for caudal block in paediatric anaesthesia". British Journal of Anaesthesia, 2000, vol. 84, No. 3, pp. 341-345.
Markus Kosel, Study of Depression-Ketamine-Brain Function, ClinicalTrials.gov, Jun. 3, 2010, Ketamine, NCT01135758.
Marlow, et al, Haemodynamic response to induction of anaesthesia with Ketamine/midazolam, Canadian Journal of Anaesthesia, May 28, 1991, pp. 844-848, vol. 38 Issue 7.
Massachusetis General Hospital, A Study of Brexpiprazole Plus Ketamine in Treatment-Resistant Depression (TRD), ClinicalTrials.gov, May 11, 2017, Ketamine, NCT03149991.
Massachusetis General Hospital, Double-Blind, Placebo-Controlled Trial of Ketamine Therapy in Treatment-Resistant Depression (TRD), ClinicalTrials.gov, Aug. 12, 2013, Ketamine, NCT01920555.
Massachusetis General Hospital, Intranasal Ketamine for Late-Life Depression and Suicidal Ideation, ClinicalTrials.gov, Nov. 20, 2014, Ketamine, NCT02295787.
Massachusetis General Hospital, Ketamine and Scopolamine Infusions for Treatment-resistant Major Depressive Disorder, ClinicalTrials.gov, Jun. 7, 2012, Ketamine, NCT01613820.
Massachusetis General Hospital, Ketamine Infusion for Treatment-resistant Major Depressive Disorder, Clinic.alTrials.gov, Apr. 23, 2012, Ketamine, NCT01582945.
Massachusetis General Hospital, N-methyl-D-aspartate Antagonist (Ketamine) Augmentation of Electroconvulsive Treatment for Severe Major Depression, ClinicalTrials.gov, Dec. 15, 2010, Ketamine, NCT01260649.
Massachusetis General Hospital, The Impact of Ketamine on the Reward Circuitry of Suicidal Patients, ClinicalTrials.gov, Aug. 25, 2015, Ketamine, NCT02532153.
Massachusetis General Hospital., Ketamine for Depression: An MRI Study, ClinicalTrials.gov, Sep. 9, 2015, Ketamine, NCT02544607.
Massachusetis General Hospital., Ketamine Versus Placebo for Treatment Resistant Major Depressive Disorder, ClinicalTrials.gov, Aug. 17, 2012, Ketamine, NCT01667926.
Massachusetis General Hospital., Neurocognitive Features of Patients With Treatment-Resistant Depression, ClinicalTrials.gov, Apr. 28, 2017, Depression, NCT03134066.
Massachusetis General Hospital., Physiological and Cognitive Biomarkers for Ketamine's Antidepressant Effects, ClinicalTrials.gov, Jan. 29, 2016, Ketamine's, NCT02669043.
Massachusetts General Hospital, A Study of Brexpiprazole Plus Ketamine in Treatment-Resistant Depression (TRD), ClinicalTrials.gov, May 11, 2017, Ketamine, NCT03149991.
Massachusetts General Hospital, Double-Blind, Placebo-Controlled Trial of Ketamine Therapy in Treatment-Resistant Depression (TRD), ClinicalTrials.gov, Aug. 12, 2013, Ketamine, NCT01920555.
Massachusetts General Hospital, Intranasal Ketamine for Late-Life Depression and Suicidal Ideation, ClinicalTrials.gov, Nov. 20, 2014, Ketamine, NCT02295787.
Massachusetts General Hospital, Ketamine and Scopolamine Infusions for Treatment-resistant Major Depressive Disorder, ClinicalTrials.gov, Jun. 7, 2012, Ketamine, NCT01613820.
Massachusetts General Hospital, Ketamine Infusion for Treatment-resistant Major Depressive Disorder, ClinicalTrials.gov, Apr. 23, 2012, Ketamine, NCT01582945.
Massachusetts General Hospital, N-methyl-D-aspartate Antagonist (Ketamine) Augmentation of Electroconvulsive Treatment for Severe Major Depression, ClinicalTrials.gov, Dec. 15, 2010, Ketamine, NCT01260649.
Massachusetts General Hospital, The Impact of Ketamine on the Reward Circuitry of Suicidal Patients, ClinicalTrials.gov, Aug. 25, 2015, Ketamine, NCT02532153.
Massachusetts General Hospital., Ketamine for Depression: An Mri Study, ClinicalTrials.gov, Sep. 9, 2015, Ketamine, NCT02544607.

(56) References Cited

OTHER PUBLICATIONS

Massachusetts General Hospital., Ketamine Versus Placebo for Treatment Resistant Major Depressive Disorder, ClinicalTrials.gov, Aug. 17, 2012, Ketamine, NCT01667926.
Massachusetts General Hospital., Neurocognitive Features of Patients With Treatment-Resistant Depression, ClinicalTrials.gov, Apr. 28, 2017, Depression, NCT03134066.
Massachusetts General Hospital., Physiological and Cognitive Biomarkers for Ketamine's Antidepressant Effects, ClinicalTrials.gov, Jan. 29, 2016, Ketamine's, NCT02669043.
Mathew Sanjay J et al: "Ketamine for treatment-resistant unipolar depression: current evidence.", CNS Drugs Mar. 1, 2012, vol. 26, No. 3, Mar. 1, 2012 (Mar. 1, 2012), pp. 189-204.
Mathew, et al., Glutamate modulators as novel interventions for mood disorders Moduladores de glutamato coma novas interven9oes em transtomos do humor, Rev Bras Psiquiatr, Jul. 15, 2005, pp. 243-248, vol. 27 Issue 3.
Mathew, et al., Riluzole for relapse prevention following intravenous ketamine in treatment-resistant depression: a pilot randomized, placebocontrolled continuation trial, Int J Neuropsychopharmacol, 2010, pp. 1-19, vol. 13 Issue 1.
May, et al., Predicting future suicide attempts among depressed suicide ideators: A 10-year longitudinal study, Journal of Psychiatric Research, Apr. 5, 2012, pp. 1-7, Page number.
Mayo Clinic, The BIO-K Study: A Single-Arm, Open-Label, Biomarker Development Clinical Trial of Ketamine for Non-Psychotic Unipolar Major Depression and Bipolar I or II Depression. (Bio-K), ClinicalTrials.gov, May 17, 2017, Ketamine, NCT03156504.
Mayo Clinic., Glutamate MRS During Ketamine Infusion, ClinicalTrials.gov, Jun. 29, 2018, Ketamine, NCT03573349.
Mayo Clinic., Ketamine Anesthesia in Electroconvulsive Therapy, ClinicalTrials.gov, Jun. 6, 2011, Ketamine, NCT01367119.
Mayo Clinic., Ketamine for Depression and Suicide Risk (Ketamine), ClinicalTrials.gov, Mar. 24, 2014, Ketamine, NCT02094898.
Mayo Clinic., Oral Ketamine in the Treatment of Depression and Anxiety in Patients With Cancer, Clinic.alTrials.gov, Sep. 7, 2012, Ketamine, NCT01680172.
Mcclean, et al., Ketamine concentrations during cardio-pulmonary bypass, Canadian Journal of Anaesthesia, Jan. 31, 1996, pp. 580-584, vol. 43 Issue 6.
Mcghee, et al, the Correlation Between Ketamine and Posttraumatic Stress Disorder in Burned Service Members, The Journal of TRAUMA, Oct. 31, 2007, pp. S195-S199, vol. 64 Issue 2.
Mcgirr, et al., A systematic review and meta-analysis of randomized, double-blind, placebo-controlled trails of ketamine in the rapid tratmet of major depressive episodes, Psychological Medicine, 2015, pp. 693-704, vol. 42.
Mclean Hospital., A Trial of Intranasal Ketamine for the Treatment of Obsessive-Compulsive Disorder, ClinicalTrials.gov, Sep. 9, 2014, Ketamine, NCT02234011.
Medical University of Graz., The Preemptive Analgetic Potency of Low Dose S-Ketamine (Miniket), ClinicalTrials.gov, Dec. 1, 2009, S-Ketamine, NCT01022840.
Medical University of Vienna., Investigation of Antidepressant Efficacy of Oral Ketamine Treatment, ClinicalTrials.gov, Dec. 14, 2016, Ketamine, NCT02992496.
Medical University of Vienna., Network Dysfunction, Schizophrenia and Pharmacological Magnetic Resonance Imaging (phMRI), ClinicalTrials.gov, Jul. 14, 2011, Esketamine, NCT01394757.
Vitiello, et al., Depressive Symptoms and Clinical Status during the Treatment of Adolescent Suicide Attempters Study (TASA), Am Acad Child Adolesc Psychiatry, 2009, pp. 997-1004, vol. 48 Issue 10.
Vollenweider et al., Differential psychopathology and patterns of cerebral glucose utilisation produced by (S)- and (R)-ketamine in healthy volunteers using positron emission tomography (PET), European Neuropsychopharmacology (1997) pp. 25-38, vol. 7.
Voort, et al., Continuation phase intravenous ketamine in adults with treatment-resistant depression, Journal of Affective Disorders, Sep. 12, 2016, pp. 300-304, vol. 206.

Vos, et al., Years lived with disability (YLDs) for 1160 sequelae of 289 diseases and injuries 1990-2010: a systematic analysis for the Global Burden of Disease Study 2010, Lancet, Dec. 29, 2012, pp. 2163-2196, vol. 380.
Vranken et al, "Iontophoretic administration of S(+)-ketamine in patients with intractable central pain: a placebo-controlled trial". Pain, 2005, 118(1-2), pp. 224-231.
Vranken, et al., Neuropathological findings after continuous intrathecal administration of S(C)-ketamine for the management of neuropathic cancer pain, Pain, Jun. 13, 2005, pp. 231-235, vol. 117.
Wan, et al., Ketamine Safety and Tolerability in Clinical Trials for Treatment-Resistant Depression, J Clin Psychiatry, 2015, pp. 1-11, vol. 76 Issue 3.
Wang et al, "Effects of penetration enhancers on the permeability of ketamine hydrochloride through an isolated rabbit's nasal mucosa", Journal of Shenyang Pharmaceutical University, 2004, Issue 5, pp. 321-323 & 340.
Wang, et al., Independent Telephone-based Assessment of Depressive Symptoms in China, Csp, 2018, pp. 1-1, Page Number.
Wang, et al., NMDA/NR2B Selective Antagonists in the Treatment of Ischemic Brain Injury, Current Drug Targets—CNS & Neurological Disorders, 2005, pp. 143-151, vol. 4 Issue 2.
Washington et al., Determination of baseline human nasal pH and the effect of intranasally administered buffers, International Journal of Pharmaceutics 198:139-146, 2000.
Washington University School of Medicine, Cognitive Recovery After Electroconvulsive Therapy and General Anesthesia (RCC2), ClinicalTrials.gov, May 4, 2016, Ketamine, NCT02761330.
Washington University School of Medicine, Treatment Resistant Depression (Pilot), ClinicalTrials.gov, Aug. 10, 2010, ketamine, NCT01179009.
Washington University School of Medicine., Nitrous Oxide as Treatment for Major Depression—a Pilot Study, ClinicalTrials.gov, May 15, 2014, Nitrous Oxide, NCT02139540.
Wasserman, et al., Saving and Empowering Young Lives in Europe (SEYLE): a randomized controlled trial, BMC Public Health, 2010, pp. 1-14, vol. 10 Issue 192.
Weksler, et al., Nasal ketamine for paediatric premedication, Canadian Journal of Anaesthesia, 1993, pp. 119-121, vol. 40 Issue 2.
White et al., Comparative Pharmacology of Ketamine Isomers, Br. J. Anaesth., 57(2):197-203, 1985.
White_et_al, Pharmacology of Ketamine Isomers in surgical Patients, Anesthesiology, 1980, pp. 231-239, vol. 52, The American Society of Anesthesiologists.
WHO Critical Review Ketamine., Introduction, WHO critical review ketamine, 2006, pp. 1-30, 34th ECDD 2006/4.3.
WHO_ Depression Fact Sheet., Media centre Depression, WHO_ Depression fact sheet, 2012, pp. 1-3, Fact sheet No. 369.
WHO_ Essential Medicines and Health Products., Essential medicines, WHO_ Essential medicines and health products, 2015, pp. 1-3, Page Number.
WHO_EXPERT Peer Review Report, Expert Committee on Drug Dependence Thirty-sixth Meeting, WHO_Expert peer review report, 2014, pp. 1-4, Agenda item 6.2.
Wikipedia, Esketamine, Wikipedia, Sep. 1, 2015, pp. 1-4, Wikipedia.
Wilkinson, et al., Cognitive Behavior Therapy May Sustain Antidepressant Effects of Intravenous Ketamine in Treatment-Resistant Depression, Psychother Psychosom, May 11, 2017, pp. 162-167, vol. 86.
William Beaumont Hospitals., IN Ketamine vs IN Midazolam and Fentanyl for Laceration Repair, ClinicalTrials.gov, May 18, 2018, Ketamine, NCT03528512.
William V. Bobo, M.D., Effect of Lithium Versus Placebo in Adults With Treatment-Resistant Depression Who Are Receiving Ketamine, ClinicalTrials.gov, Sep. 25, 2017, Ketamine, NCT03290963.
Williams, "Development and reliability of a structured interview guide for the Montgomery asberg depression rating Scale (SIGMA)", Br. J. Psychiatry, 2008, 192(1), 52-58 on days 1 (pre-dose and 2 hour post-dose), 2, 8 (pre-dose), 9, and 15, using the structured interview guide (Sigma). See, Williams 2008.
Williams, et al., Attenuation of Antidepressant Effects of Ketamine by Opioid Receptor Antagonism, ajp.psychiatryonline.org, 2018, pp. 1-11, pagenumber.

(56) References Cited

OTHER PUBLICATIONS

Williams, et al., Opioid Receptor Anesthesia attenuates Antidepressant Effects of Ketamine, Biological Psychiatry, May 12, 2018, pp 1-1.
Wirz-Justice, et al., Sleep Deprivation in Depression: What Do We Know, Where Do We Go?, Biol Psychiatry, May 18, 1999, pp. 445-453, vol. 46.
Womble, et al., Effects of Ketamine on Major Depressive Disorder in a Patient With Posttraumatic Stress Disorder, AANA Journal, 2013, pp. 118-119, vol. 81 Issue 2.
Wonkwang University Hospital., Dexamethasone and Ketamine on Change of Postoperative Mood, ClinicalTrials.gov, Jun. 21, 2017, Ketamine, NCT03194594.
Yale University, Ketamine for Depression and Alcohol Dependence (KetamineDep), ClinicalTrials.gov, Mar. 12, 2012, Ketalar (ketamine), NCT01551329.
Yale University, Trial of Ketamine and Lithium Therapy in Bipolar Depression, ClinicalTrials.gov, Jan. 15, 2013, Ketamine, NCT01768767.
Yale University., Alpha-Amino-3-Hydroxy-5-Methyl-4-Isoxazole Propionic Acid Receptor Components of the Anti-Depressant Ketamine Response, ClinicalTrials.gov, Dec. 8, 2017, Ketamine, NCT03367533.
Yale University., Cognitive Behavioral Therapy in Prolonging the Antidepressant Effects of Intravenous Ketamine, ClinicalTrials.gov, Nov. 13, 2014, Ketamine, NCT02289248.
Yale University., Cognitive Therapy to Sustain the Antidepressant Effects of Intravenous Ketamine in Treatment-resistant Depression, ClinicalTrials.gov, Jan. 23, 2017, ketamine, NCT03027362.
Yale University., Examining the Effect of Ketamine on Glutamate/Glutamine Cycling, ClinicalTrials.gov, Jan. 15, 2014, Ketamine, NCT02037035.
Yale University., Imaging SV2A in Mood Disorders, ClinicalTrials.gov, Apr. 12, 2016, ketamine, NCT02734602.
Yale University., Ketamine for Low Mood States in the ER, ClinicalTrials.gov, Sep. 27, 2010, Ketamine, NCT01209845.
Yale University., Ketamine in Borderline Personality Disorder, ClinicalTrials.gov, Jan. 10, 2018, Ketamine, NCT03395314.
Yale University., Ketamine Infusion for Adolescent Depression and Anxiety, ClinicalTrials.gov, Oct. 20, 2015, Ketamine, NCT02579928.
Yale University., PET Imaging of mGLuRS With Drug Challenge, ClinicalTrials.gov, Sep. 24, 2012, ketamine, NCT01691092.
Yang et al., Serum interleukin-6 is a predictive biomarker for ketamine's antidepressant effect in treatment-resistant patients with major depression. Biological psychiatry 77, 2015b, pp. e19-e20.
Yang, et al., R-ketamine: a rapid-onset and sustained antidepressant without psychotomimetic side effects, Transl Psychiatry, Sep. 1, 2015, pp. 1-19, vol. 5 Issue 9.
Yilmaz, et al., Prolonged effect of an anesthetic dose of ketamine on behavioral despair, Pharmacology, Biochemistry and Behavior, 2002, pp. 341-344, vol. 71.
Young, et al., Young Mania Rating Scale (YMRS), Br J Psychiatry, 1978, pp. 429-435, vol. 133.
Zanos, et al., Effects of a ketamine metabolite on synaptic NMDAR function, Nature, Jun. 22, 2017, pp. E1-E2, vol. 546.
Zanos, et al., Intracellular Signaling Pathways Involved in (S)- and (R)-Ketamine Antidepressant Actions, Biological Psychiatry, Jan. 1, 2008, pp. 2-4, vol. 83.
Zarate, et al., A Double-Blind, Placebo-Controlled Study of Memantine in the Treatment of Major Depression, Am J Psychiatry, 2006, pp. 153-155, vol. 163 Issue 1.
Quintana, et al., Dose-dependent social-congnitive effects of intranasal oxytocin delivered with novel Breath Powered device in adults with autism spectrum disorder: a randomized placebo-controlled double-blind crossover trial, Translational Psychiatry, May 23, 2017, pp. 1-9, vol. 7.
Rad., Ketamine as an Alternative Treatment to ECT in Major Depressive Disorder, ClinicalTrials. gov, Jan. 20, 2016, Ketamine, NCT02659085.
Randall, et al., Assessment of Self-Harm Risk Using Implicit Thoughts, Psychological Assessment, May 6, 2013, pp. 1-8, Page Number.
Rasmussen, et al., Serial infusions of low-dose ketamine for major depression, Journal of Psychopharmacology, 2013, pp. 444-450, vol. 27 Issue 5.
Rebecca Price, Intravenous Ketamine Plus Neurocognitive Training for Depression, ClinicalTrials.gov, Aug. 2, 2017, Intravenous ketamine, NCT03237286.
Reeves, et al., Efficacy of Risperidone Augmentation to Antidepressants in the Management of Suicidality in Major Depressive Disorder: A Randomized, Double-Blind, Placebo-Controlled Pilot Study, J Clin Psychiatry, 2008, pp. 1228-1236, vol. 69 Issue 8.
Remigius U Agu., Challenges in nasal drug absorption: how far have we come?, Future Science, Jul. 12, 2016, pp. 1-2, vol. 7 Issue 7.
Rhode Island Hospital, Intranasal Ketamine for Procedural Sedation in Pediatric Laceration Repair, ClinicalTrials.gov, Mar. 23, 2007, Ketamine, NCT00451724.
Ribeiro, et al., The Use of Ketamine for the Treatment of Depression in the Context of Psychotic Symptoms, Biological Psychiatry, May 1, 2016, pp. e65-e66, vol. 79.
Rot, et al., Ketamine for Depression: Where Do We Go from Here?, Biol Psychiatry, May 9, 2012, pp. 1-31, Page Number.
Rothman, et al., Noncompetitive N-Methyl-D-Aspartate Antagonists Affect Multiple Lonie Currents, The Journal of Pharamacology and Experimental Therapeutics, Mar. 30, 1988, pp. 137-142, vol. 246 Issue 1.
Rush et al., "The 16-item quick inventory of depressive symptomatology (QIDS), Clinician Rating (QIDS-C) and Self-Report (QIDS-SR): A psychometric evaluation in patients with chronic major depression", Biol. Psychiatry, 2003, 54(5), 573-583.
Rush, et al, Research Issues in the Study of Difficult-to-Treat Depression, Biol Psychiatry, Jan. 13, 2003, pp. 743-753, vol. 53.
Rush, et al., Acute and Longer-Term Outcomes in Depresses Outpatients Requiring one or Several Treatment Steps; A STAR*D Report, Am. J. Psychiatry, 2006, pp. 1905-1917, vol. 163.
Rush, et al., Massachusetts General Hospital Antidepressant Treatment Response Questionnaire; Rush, "The Inventory of Depressive Symptomatology (IDS): Psychometric Properties", Psychol. Med., 1996, 26(3), 477-486.
Rybakowski et al., Single ketamine infusion in bipolar depression resistant to antidepressants: are neurotrophins involved? Human psychopharmacology 28, 2013, pp. 87-90.
Rybin, "Placebo non-response measure in sequential parallel comparison design studies", Stat. Med., 2015, 34(15), 2281-2293.
Sackeim, et al., Vagus Nerve Stimulation (VNS™) for Treatment-Resistant Depression: Efficacy, Side Effects, and Predictors of Outcome, Neuropsychopharmacology, Apr. 24, 2001, pp. 713-728, vol. 25 Issue 5.
Sackeim, Ph.D., "The Definition and Meaning of Treatment-Resistant Depression", J Clin Psychiatry, 2001, pp. 10-17, vol. 62 Issue 16.
Sadove, et al, Analgesic Effects of Ketamine Administered in Subdissociative Doses, Anaesthesia and Analgesia. Current Researches, 1971, pp. 452-457, vol. 50 Issue 3.
Salvadore et al., Anterior cingulate desynchronization and functional connectivity with the amygdala during a working memory task predict rapid antidepressant response to ketamine. Neuropsychopharmacology: official publication of the American College of Neuropsychopharmacology 35, 2010, pp. 1415-1422.
Salvadore G Ed—Sanacora Gerard et al: "Impact of the Va166Met Polymorphism of Brain-Derived Neurotrophic Factor on Esketamine and Ketamine Antidepressant Effects in Patients with Treatment-Resistant Depression", Biological Psychiatryvol. 77, No. 9 supplement, May 1, 2015 (May 1, 2015), p. 360S.
Sanacora, et al., Subtype-Specific Alterations of γ-Aminobutyric Acid and Glutamate in Patients With Major Depression, Arch Gen Psychiatry, 2004, pp. 705-713, vol. 61.
Sapolsky, et al., Commentary Is Impaired Neurogenesis Relevant to the Affective Symptoms of Depression?, Biol Psychiatry, 2004, pp. 137-139, vol. 56.
Sarchiapone, et al., Association of Polymorphism (Val66met) of Brain-Derived Neurotrophic Factor with Sucide Attempts in Depressed Patients, Neuropsychobiology, Jul. 7, 2008, pp. 139-145, vol. 57.

(56) References Cited

OTHER PUBLICATIONS

Saveanu, et al., The International Study to Predict Optimized Treatment in Depression (iSPOT-D): Outcomes from the acute phase of antidepressant treatment, Journal of Psychiatric Research, Dec. 23, 2014, pp. 1-12, vol. 61.
Scheidegger et al., Ketamine administration reduces amygdalo-hippocampal reactivity to emotional stimulation. Human brain mapping 37, 2016, pp. 1941-1952.
Schonenberg, et al., Ketamine aggravates symptoms of acute stress disorder in a naturalistic sample of accident victims, Journal of Psychopharmacology, 2008, pp. 493-497, vol. 22 Issue 5.
Schule, et al., Repeated S-Ketamine Infusions in Treatment-Resistant Depression, Topic: E02-e-Poster Oral Session 02: Depression and Suicide, 2014, pp. 1-1, Article EPA-1659.
Scott A. Irwin, MD, PHO., Study of Oral Ketamine Versus Placebo for Treating Depression in Patients Undergoing Treatment for Cancer, ClinicalTrials.gov, Jul. 19, 2016, Ketamine, NCT02836288.
Shalvata Mental Health Center, Intra-nasal vs. Intravenous Ketamine Administration, ClinicalTrials.gov, Jan. 1, 2016, Ketamine, NCT02644629.
Shaw et al., Ketamine amplifies induced gamma frequency oscillations in the human cerebral cortex. European neuropsychopharmacology : the journal of the European College of Neuropsychopharmacology 25, 2015, pp. 1136-1146.
Sheba Medical Center., D-cycloserine for Relapse Prevention Following Intravenous Ketamine in Treatmentresistant Depression, ClinicalTrials.gov, May 13, 2016, Ketamine, NCT02772211.
Sheba Medical Center., Ketamine Infusions for Major Depression Disorder (Ketamie), ClinicalTrials.gov, Aug. 19, 2014, Ketamine, NCT02219867.
Shi Jinyun, Study of Ketamine as an Antidepressant in Major Depressive Disorder, ClinicalTrials.gov, Apr. 9, 2012, Ketamine, NCT01573741.
Shiroma et al., Neurocognitive performance and serial intravenous subanesthetic ketamine in treatment-resistant depression. The international journal of neuropsychopharmacology / official scientific journal of the Collegium Internationale Neuropsychopharmacologicum 17, 2014, pp. 1805-1813.
Shiroma, et al., Augmentation of response and remission to serial intravenous subanesthetic ketamine in treatment resistant depression, Journal of AffectiveDisorders, Oct. 29, 2013, pp. 123-129, vol. 155.
Short, AL., Side-effects associated with ketamine use in depression: a systematic review, Lancet Psychiatry, 2018, pp. 65-78, vol. 5.
Simon, "What If Ketamine Actually Works Like an Opioid?", Wired, Aug. 29, 2018, 1-10.
Singh Jaskaran: Intranasal sketamine in, Treatment Resistant Depression—A Double-blind, Randomized, Efficacy and Dose Response Study, International Journal of Neuropsychopharmacology, Cambridge Univ. Press, Cambridge, vol. 19, No. Suppl. 1, May 31, 2016 (May 31, 2016), XP009511636, p. 24, ISSN: 1461-1457, DOI: 10.7490/F1000RESEARCH.1111967.I.
Singh, et al., A Double-Blind, Randomized, Placebo-Controlled, Dose-Frequency Study of Intravenous Ketamine in Patients With Treatment-Resistant Depression, AmJ Psychiatry, 2016, pp. 816-826, vol. 173.
Skolnick et al, Glutamate-based antidepressants: 20 years on, Trends in Pharmacological Sciences, 2006, pp. 563-569, vol. 30 Issue 11.
Skolnick, et al., Adaptation of N-Methyl-D-Aspartate (NMDA) Receptors following Antidepressant Treatment: Implications for the Pharmacotherapy of Depression, Pharamacopsychiat, 1996, pp. 23-26, vol. 29.
Skolnick, et al., Antidepressants for the new millennium, European Journal of Pharmacology, Apr. 30, 1999, pp. 31-40, vol. 375.
Skolnick, et al., Modulation of glutamate receptors: Strategies for the development of novel antidepressants, Amino Acids, Jun. 17, 2002, pp. 153-159, vol. 23.
Smith, et al., Properties of the Optical Isomers and Metabolites of Ketamine on the High Affinity Transport and Catabolism of Monoamines, Neuropharmacology, 1981, pp. 391-396, vol. 20.

Sofia, et al., Evaluation of Ketamine HCL for Anti-Depressant Activity, Arch. int. Pharmacodyn., 1975, pp. 68-74, vol. 214.
Soni, et al., Safety assessment of esters of p-hydroxybenzoic acid parabens, Food and Chemical Toxicology, Jan. 31, 2005, pp. 985-1015, vol. 43.
Soni, M.G. et al., Food Chem Toxicol., 2001, pp. 513-532, 39(6).
Holma, et al., Incidence and Predictors of Suicide Attempts in DSM-IV Major Depressive Disorder: A Five-Year Prospective Study, Am J Psychiatry, Jan. 19, 2010, pp. 801-808, vol. 167 Issue 7.
Hong, J. et al., Curr Opin Allergy Clin Immunol., 2009, pp. 447-453, 9(5).
Horr, et al., Ketamine: A Potential Option for Treatment-Refractory Depression in Elder Adults, Conference Poster, 2014, pp. 179-179, Poster C39.
Hospira, Now a Wholly Owned Subsidiary of Pfizer, Safety and Efficacy of Repeated Doses of PMI-150 (Intranasal Ketamine) in Acute Postoperative Pain Following Orthopedic Surgery, ClinicalTrials.gov, Jul. 3, 2008, Ketamine, NCT00709436.
Hospira, Nowa Wholly Owned Subsidiary of Pfizer, Safety and Efficacy of Pmi-150 (Intranasal Ketamine) for the Treatment of Breakthrough Pain in Cancer Patients, ClinicalTrials.gov, Jun. 27, 2007, Ketamine, NCT00492388.
Hospital De Clinicas De Porto Alegre., Intranasal Ketamine as a Sedative for Venipuncture, ClinicalTrials.gov, Oct. 11, 2016, Ketamine, NCT02929524.
http://www.pfizer.com/files/products/material safety data/PZ00892.pdf; 2008.
https://en.wikipedia.org/wiki/Esketamine; 2015.
Hu, et al., Single i.v. ketamine augmentation of newly initiated escitalopram for major depression: results from a randomized, placebo-controlled 4-week study, Psychological Medicine, Oct. 19, 2015, pp. 623-635, vol. 46.
Huang et al., Mechanism of Nasal Absorption of Drugs I: Physicochemical Parameters Influencing the Rate of In Situ Nasal Absorption of Drugs in Rats, Journal of Pharmaceutical Sciences, 74(61:608-611, 1985.
Huang, "Comparison of test statistics for the sequential parallel design", Statistics in Biopharmaceutical Research, 2010, 2(1), 42-50.
Hudetz, J. Cardiothor. Vase. Anesth., 2010, 24, 131-142.
Huge V et al: "Effects of low-dose intranasal (S)-ketamine in patients with neuropathic pain", European Journal of Pain, Saunders, London, GB, vol. 14, No. 4, Apr. 1, 2010 (Apr. 1, 2010), pp. 387-394, XP026985780, ISSN: 1090-3801 [retrieved on Mar. 9, 2009] paragraph [02.2].
Hunt, et al., Suicide amongst psychiatric in-patients who abscond from the ward: a national clinical survey, BMC Psychiatry, Feb. 3, 2010, pp. 1-6, vol. 10 Issue 14.
Husain, et al., Speed of Response and Remission in Major Depressive Disordwer With Acute Electroconvulsive Therapy (ECT); A Consortium for Research in ECT (CORE) Report, J Clin Psychiatry, 2004, pp. 485-491, vol. 65 Issue 4.
Hustveit, et al., Interaction of the Chiral Forms of Ketamine with Opioid Phencyclidine, and Muscarinic Receptors, Pharmacology & Toxicology, Apr. 25, 1995, pp. 355-359, vol. 77.
Hvidovre University Hospital., Optimal Multimodal Analgesia in Abdominal Hysterectomy, ClinicalTrials.gov, Sep. 21, 2005, S-ketamine, NCT00209872.
Hvidovre University Hospital., Optimal Multimodal Analgesia in Laparoscopic Cholecystectomy, ClinicalTrials. gov, Sep. 21, 2005, S-ketamine, NCT00209885.
Hyman, et al., Initiation and Adaptation : A Paradigm for Understanding Psychotropic Drug Action, Am J Psychiatry, 1996, pp. 151-162, vol. 153.
Ibrahim, et al., Rapid decrease in depressive symptoms with an N-methyl-d-aspartate antagonist in ECT-resistant major depression, Progress in Neuro-Psychopharmacology & Biological Psychiatry, Apr. 3, 2011, pp. 1155-1159, vol. 35.
Icahn School of Medicine at Mount Sinai, Ketamine and Nitroprusside for Depression, ClinicalTrials.gov, Apr. 6, 2017, Ketamine, NCT03102736.

(56) References Cited

OTHER PUBLICATIONS

Icahn School of Medicine at Mount Sinai, Ketamine Plus Lithium in Treatment-Resistant Depression, ClinicalTrials.gov, Jun. 19, 2013, Ketamine, NCT01880593.
Icahn School of Medicine at Mount Sinai, Treatment Study of Bipolar Depression, ClinicalTrials.gov, Jul. 29, 2009, ketamine, NCT00947791.
Icahn School of Medicine at Mount Sinai., MRI Studies of Emotion in Depression, ClinicalTrials.gov, Apr. 29, 2015, ketamine, NCT02429011.
Iglewicz, et al., Ketamine for the Treatment of Depression in Patients Receiving Hospice Care: A Retrospective Chart Review of Thirty-One Cases, Psychosomatics., 2015, pp. 329-337, vol. 56 Issue 4.
Ingrid Torjesen., Ketamine helps a third of patients with treatment resistant depression, finds small UK study, BMJ, Apr. 3, 2014, pp. g2576-g2576, vol. 348.
Inonu University., Effect of the Addition of Ketamine to Sevoflurane Anesthesia in Electroconvulsive Therapy, Clinic.alTrials.gov, Oct. 20, 2014, Ketamine, NCT02267980.
Inonu University., Effects of Sevoflurane and Ketamine on QT in Electroconvulsive Therapy, ClinicalTrials.gov, Jun. 6, 2013, Ketamine, NCT01870219.
Instituto Mexicano Del Seguro Social, Effect of Ketamine in Depressive Symptoms of Elderly Patients With Visual Impairment., ClinicalTrials.gov, Mar. 22, 2018, Ketamine, NCT03473431.
International Preliminary Report on Patentability received for PCT Patent Application No. PCT/US13/30476, dated Sep. 25, 2014, 11 pages.
International Preliminary Report on Patentability received for PCT Patent Application No. PCT/US14/27074, dated Sep. 24, 2015, 7 pages.
International Preliminary Report on Patentability received for PCT Patent Application No. PCT/US2016/033404, dated Nov. 30, 2017, 8 pages.
International Search Report and Written Opinion received for PCT Patent Application No. PCT/US13/30476, dated Apr. 24, 2013, 11 pages.
International Search Report and Written Opinion received for PCT Patent Application No. PCT/US14/27074, dated May 27, 2014, 9 pages.
International Search Report and Written Opinion received for PCT Patent Application No. PCT/US2016/033404, dated Aug. 16, 2016, 9 pages.
International Search Report re: PCT/EP2016/060922 dated Jul. 28, 2016.
International Search Report re: PCT/US2013/030476 dated Apr. 24, 2013.
International Search Report re: PCT/US2014/027059 dated Jul. 16, 2014.
International Search Report re: PCT/US2014/027074 dated May 27, 2014.
International Search Report re: PCT/US2015/049961 dated Jan. 12, 2016.
International Search Report re: PCT/US2015/44830 dated Nov. 23, 2015.
International Search Report re: PCT/US2016/33404 dated Aug. 16, 2016.
Ionescu, et al., Effect of Baseline Anxious Depression on Initial and Sustained Antidepressant Response to Ketamine, J Clin Psychiatry, 2014, pp. e932-e938, vol. 75 Issue 9.
Ionescu, et al., Rapid and Sustained Reductions in Current Suicidal Ideation Following Repeated Doces of Intravenous Ketamine:, J Clin Psychiatry, 2016, pp. e1-e7, page number.
Irwin, et al., Daily Oral Ketamine for the Treatment of Depression and Anxiety in Patients Receiving Hospice Care: A 28-Day Open-Label Proof-of-Concept Trial, Journal of Palliative Medicine, 2013, pp. 958-965, vol. 16 Issue 8.
Irwin, et al., Oral Ketamine for the Rapid Treatment of Depression and Anxiety in Patients Receiving Hospice Care, Journal of Palliative Medicine, Jan. 13, 2010, pp. 903-908, vol. 13 Issue 7.
Irwin, MD, PHO., Study of Oral Ketamine Versus Placebo for Treating Depression in Patients Undergoing Treatment for Cancer, ClinicalTrials.gov, Jul. 19, 2016, Ketamine, NCT02836288.
Isometsa, et al., Suicide in Major Depression, AmL Psychiatry, 1994, pp. 530-536, vol. 151 Issue 4.
Ivanova, "Optimality, sample size, and power calculations for the sequential parallel comparison design", Stat. Med., 2011, 30(23), 2793-2803.
Jafarinia, et al., Efficacy and safety of oral ketamine versus diclofenac to alleviate mild to moderate depression in chronic pain patients: A double-blind, randomized.controlled trial, Journal ofAffectiveDisorders, Jun. 1, 2016, pp. 1-8, vol. 204.
Juvenile Bipolar Research Foundation., Intranasal Ketamine in the Treatment of Pediatric Bipolar Disorder (IKBP), ClinicalTrials.gov, Jan. 5, 2012, Ketamine, NCT01504659.
Kallmunzer, et al., Treatment escalation in patients not responding to pharmacotherapy, psychotherapy, and electro-convulsive therapy: experiences from a novel regimen using intravenous S-ketamine as add-on therapy in treatment-resistant depression, J Neural Transmz, Dec. 31, 2015, pp. 549-552, vol. 123.
Kane, et al., Clozapine and Haloperidol in Moderately Refractory Schizophrenia, Arch Gen Psychiatry, Mar. 22, 2001, pp. 965-972, vol. 58.
Kapur, et al., Ketamine Has Equal Affinity for Nmda Receptors and the High-Affinity State of the Dopamine 02 Receptor, Biol Psychiatry, 2001, pp. 954-957, vol. 49.
Kapur, et al., Psychiatric inpatient care and suicide in England, 1997 to 2008: a longitudinal study, Psychological Medicine, Jun. 24, 2013, pp. 61-71, vol. 43 Issue 1.
Kaul, et al., *Homo sapiens* chromosome 3 clone RP11-466A13, Complete Sequence, GenBank, 2002, pp. 1-40, AC099753.
Keller, Issues in Treatment-Resistant Depression, J Clin Psychiatry, 2005, pp. 5-12, vol. 66 Supp.lementary 8.
Kellner, et al., Relief of Expressed Suicidal Intent by ECT: A Consortium for Research in ECT Study, Am J Psychiatry, 2005, pp. 972-982, vol. 162 Issue 5.
Kessler, et al., Lifetime Prevalence and Age-of-Onset Distributions of DSM-IV Disorders in the National Comorbidity Survey Replication, Arch Gen Psychiatry, 2005, pp. 593-602, vol. 62.
Ketamine Hydrochloride Injection, Ketamine Hydrochloride—ketamine hydrochloride injection JHP Pharmaceuticals, LLC, Ketamine Hydrochloride Injection, 2013, pp. 1-17, page number.
Khan, "Has the rising placebo response impacted antidepressant clinical trail outcome? Data from the US Food and Drug Administration 1987-2013", World Psychiatry, 2017, 16(2), 181-192.
KK Women's and Children's Hospital, S Ketamine Use in Total Abdominal Hysterectomy (SKET), ClinicalTrials.gov, Sep. 7, 2015, S Ketamine, NCT02543385.
KK Women's and Children's Hospital, Use of S+Ketamine During Target-Controlled Intravenous Anaesthesia After Abdominal Hysterectomy, ClinicalTrials.gov, Jul. 27, 2017, Esketamine, NCT03231683.
Kollmar, et al., Ketamine followed by memantine for the treatment of major depression, Correspondence, 2008, pp. 1-1, Page Number.
Kosel, Study of Depression-Ketamine-Brain Function, ClinicalTrials.gov, Jun. 3, 2010, Ketamine, NCT01135758.
Krystal, et al., Comparative and Interactive Human Psychopharmacologic Effects of Ketamine and Amphetamine, Arch Gen Psychiatry, Mar. 18, 2005, pp. 985-995, vol. 62.
Krystal, et al., Glutamate and GABA systems as targets for novel antidepressant and mood-stabilizing treatments, Molecular Psychiatry, 2002, pp. S71-S80, vol. 7.
Krystal, et al., Interactive effects of subanesthetic ketamine and haloperidol in healthy humans, Psychopharmacology, Feb. 23, 1999, pp. 193-204, vol. 145.
Krystal, et al., Interactive effects of subanesthetic ketamine and subhypnotic lorazepam in humans, Psychopharmacology, 1998, pp. 213-229, vol. 135.
Krystal, et al., Preliminary evidence of attenuation of the disruptive effects of the NMDA glutamate receptor antagonist, ketamine, on working memory by pretreatment with the group II metabotropic

(56) References Cited

OTHER PUBLICATIONS glutamate receptor agonist, LY354740, in healthy human subjects, Psychopharmacology, 2005, pp. 303-309, vol. 179.

Krystal, et al., Subanesthetic Effects of the Noncompetitive Nmda Antagonist, Ketamine, in Humans, Arch Gen Psychiatry, 1994, pp. 199-214, vol. 51.

Kudoh, et al., Small-Dose Ketamine Improves the Postoperative State of Depressed Patients, Anesth Analg, Mar. 12, 2002, pp. 114-118, vol. 95.

Lai, et al., Pilot dose-response trial of i.v. ketamine in treatment-resistant depression, The World Journal of Biological Psychiatry, Jun. 9, 2014, pp. 579-584, vol. 15.

Laje et al., "Brain-Derived Neurotrophic Factor Val66Met Polymorphism and Antidepressant Efficacy of Ketamine in Depressed Patients", Biol Psychiatry, vol. 72, No. 11, Dec. 1, 2012, pp. e27-e28.

Lally, et al., Neural correlates of change in major depressive disorder anhedonia following open-label ketamine, J Psychopharmacol, 2015, pp. 596-607, vol. 29 Issue 5.

Lamothe., Ketamine for Treatment-resistant Depression: A Multicentric Clinical Trial in Mexican Population, ClinicalTrials.gov, Jun. 5, 2013, Ketamine, NCT01868802.

Lapidus, et al., A Randomized Controlled Trial of Intranasal Ketamine in Major Depressive Disorder, Biol Psychiatry, Dec. 15, 2014, pp. 970-976, vol. 76 Issue 12.

Lapidus, et al., In Vivo Proton Magnetic Resonance Spectroscopy Study of the Relationships Between Lactate, Depression Severity, and Ketamine Treatment in Major Depressive Disorder, Neuropsychopharmacology, 2015, pp. 1-169, Poaste W113.

Lara, et al., Antidepressant, mood stabilizing and procognitive effects of very low dose sublingual ketamine in refractory unipolar and bipolar depression, International Journal of Neuropsychopharmacology, 2013, pp. 2111-2117, vol. 16.

Larkin, et al., A preliminary naturalistic study of low-dose ketamine for depression and suicide ideation in the emergency department, International Journal of Neuropsychopharmacology, May 5, 2011, pp. 1127-1131, vol. 14.

Lavito, "Ketamine is emerging as a popular treatment for depression. New research suggests the drug acts like an opioid", Biotech and Pharmaceuticals, Aug. 29, 2018, pp. 1-5.

Lawson Health Research Institute, Intranasal Ketamine for Procedural Sedation (INK), ClinicalTrials.gov, Jul. 11, 2016, Ketamine, NCT02828566.

Layer, et al., Anttidepressant-like Actions of the Polyamine Site NMDA Antagonist, Eliprodil (SL-82.0715), Pharmacology Biochemistry and Behavior, 1995, pp. 621-627, vol. 52 Issue 3.

Lee, et al., NMDA Receptors Offer More Than One Functionality, Anesth Analg, 2003, pp. 1533-1534, vol. 96.

Lenze, et al., Ninety-six hour ketamine infusion with co-administered clonidine for treatment-resistant depression: a pilot randomized controlled trial, World J Biol Psychiatry, 2016, pp. 230-238, vol. 17 Issue 3.

Levine, et al., Assessment of suicide risk by computer-delivered self-rating questionnaire: preliminary findings, Acta Psychiatr Scand, Feb. 25, 1981, pp. 216-220, vol. 80.

Li, et al., The Effects of Low-Dose Ketamine on the Prefrontal Cortex and Amygdala in Treatment-Resistant Depression: A Randomized Controlled Study, Human Brain Mapping, Jan. 29, 2016, pp. 1080-1090, vol. 37.

Liebrenz, et al., Intravenous ketamine therapy in a patient with a treatment-resistant major depression, Swiss Med Wkly, 2007, pp. 234-236, vol. 137.

Liebrenz, et al., Repeated intravenous ketamine therapy in a patient with treatment-resistant major depression, The World Journal of Biological Psychiatry, Dec. 8, 2009, pp. 640-643, vol. 10 Issue 4.

Lim, Y.Y. et al., (Australian Imaging, Biomarkers and Lifestyle (AIBL) Research Group), "BDNF Val66Met, AB Amyloid and cognitive decline in preclinical Alzheimer's disease", Neurobiol. Aging, Nov. 2013, vol. 34(11), pp. 2457-2464.

Lindefors, et al., Differential effects of single and repeated ketamine administration on dopamine, serotonin and GABA transmission in rat medial prefrontal cortex, Brain Research, Feb. 11, 1997, pp. 205-212, vol. 759.

Lions Gate Hospital, Intra-nasal Ketamine for Analgesia in the Emergency Department (INKA), ClinicalTrials.gov, Sep. 17, 2012, Ketamine, NCT01686009.

Liu, "Doubly-randomized delayed-start design for enrichment studies with responders or non-responders", J. Biopharm. Stat, 2012, 22(4), 737-757.

Liu, R.Y., Biol. Psychiatry, BDNF Val66Met allele impairs basal and ketamine-stimulated synaptogenesis in prefrontal cortex, 2012, vol. 71 (11), pp. 996-1005.

Lodge, et al., Ketamine and phencyclidine: the good, the bad and the unexpected, British Journal of Pharmacology, Jun. 3, 2015, pp. 4254-4276, vol. 172.

Logan et al., Immobilizing wild mountain lions (*felis concolor*) with ketamine hydrochloride and xylazine hydrochloridem, Journal of Wildlife Diseases, 22(1):97-103, 1986.

Loo, et al., Placebo-controlled pilot trial testing dose titration and intravenous, intramuscular and subcutaneous routes for ketamine in depression, Acta Psychiatr Scand, Feb. 22, 2016, pp. 48-56, vol. 134.

Lopez, et al., Use of repeated intravenous ketamine therapy in treatment-resistant bipolar depression with suicidal behaviour: a case report from Spain, Therapeutic Advances in Psychopharmacology, 2017, pp. 137-140, vol. 7 Issue 4.

Clements, et al., Bioavailability, Pharmacokinetics, and Analgesic Activity of Ketamine in Humans, Journal of Pharmaceutical Sciences, 1982, pp. 539-542, vol. 71 Issue 5.

Clinical trials.gov_NCT01998958, A Study to Evaluate the Safety and Efficacy of Intranasal Esketamine in Treatment-resistant Depression. ClinicalTrials.gov Identifier: NCT01998958. Jul. 14, 2014 [online]. [Retrieved on Sep. 23, 2015]. Retrieved from the Internet: <URL: https://clinicaltrials.gov/archive/NCT01998958/2014_07_14> PDF File: p. 1-40. p. 1, Brief Summary, Phase, and the last para; and p. 2, para 1 and 3.

ClinicalTrials.gov Identifier: NCT02497287 (2015).

Cohen, Anesthesiol., 1973, 39, 370-376.

Columbia University., Ketamine in the Treatment of Depression, ClinicalTrials.gov, Mar. 20, 2012, Ketamine, NCT01558063.

Compton et al., International Journal of Life Science and Medical Research, 2013, vol. 3, issue 5, 179-192.

Compton, et al., Cognitive-Behavioral Psychotherapy for Anxiety and Depressive Disorders in Children and Adolescents: An Evidence-Based Medicine Review, J. Am. Acad. Child Adolesc. Psychiatry, Nov. 17, 2003, pp. 930-959, vol. 43 Issue 8.

Controlled Trial in Treatment-Resistant Depression, Depress Anxiety., 2014, pp. 1-18, vol. 31 D.

Cornwell, et al., Synaptic Potentiation Is Critical for Rapid Antidepressant Response to Ketamine in Treatment-Resistant Major Depression, Biol Psychiatry, Mar. 29, 2012, pp. 555-561, vol. 72.

Correia-Melo, et al., Rapid infusion of esketamine for unipolar and bipolar depression: a retrospective chart review, Neuropsychiatric Disease and Treatment, Jun. 21, 2017, pp. 1627-1632, vol. 13.

Correll, et al., Two Case Studies of Patients with Major Depressive Disorder Given Low-Dose (Subanesthetic) Ketamine Infusions, Pain Medicine, 2006, pp. 92-95, vol. 7 Issue 1.

Corso, et al., Medical Costs and Productivity Losses Due to Interpersonal and Self-Directed Violence in the United States, Am J Prev Med, 2007, pp. 474-482, vol. 32 Issue 6.

Corssen, et al., Computerized Evaluation of Psychic Effects of Ketamine, Anesthesia & Analgesia, 1971, pp. 397-401, vol. 50 Issue 3.

Corwin Boake., Historical Note Edouard Claparede and the Auditory Verbal Learning Test, Journal of Clinical and Experimental Neuropsychology, Oct. 18, 2000, pp. 286-292, vol. 22 Issue 2.

Crosby, et al., Suicidal Thoughts and Behaviors Among Adults Aged graterthan & equal 18 Years—United States, 2008-2009, Centers for Disease Control and Prevention, Oct. 21, 2011, pp. 1-28, vol. 60 Issue 13.

(56) References Cited

OTHER PUBLICATIONS

Cusin, et al., Ketamine augmentation for outpatients with treatment-resistant depression: Preliminary evidence for two-step intravenous dose escalation, Australian & New Zealand Journal of Psychiatry, 2016, pp. 1-10.
Cusin, et al., Long-Term Maintenance With Intramuscular Ketamine for Treatment-Resistant Bipolar II Depression, Am J Psychiatry, 2012, pp. 868-867, vol. 169 Issue 8.
D'Sa, et al., Antidepressants and neuroplasticity, Bipolar Disorders, Feb. 1, 2002, pp. 183-194, vol. 4.
Daly Ella et al: "I ntranasa 1 Esketamine, 'in Treatment-resistant Depression, a Dose Response Study—Double Blind and Open Label Extension Data", Neuropsychopharmacology, Elsevier Science Publishing, New York, NY, US, vol. 40, No. Suppl. 1, Dec. 1, 2015 (Dec. 1, 2015), S340-S341, XP009509885, pp. ISSN: 0893-133X *abstract*.
Daly et al., "Intranasal, Esketamine in Treatment Resistant Depression—A Double-blind, Randomized, Efficacy and Dose Response Study", Biological Psychiatry, vol. 79, No. 9, Suppl. s, May 1, 2016, pp. 206S-207S, XP009511637, 71st Annual Scientific Convention and Meeting of the Society-Of-Biological-Psychiatry (SOBP); Atlanta, GA, USA; May 12-14, 2016 abstract.
Daly, "Efficacy and Safety of Intranasal Esketamine Adjunctive to Oral Antidepressant Therapy in Treatment-Resistant Depression", JAMA, vol. 75, No. 2, Feb. 1, 2018, pp. 139-148.
Daly, et al., ESKETINTRD3003 ASCP Pipeline Presentation, Janssen Research & Therapeutic Area, May 29, 2018, pp. 1-21.
Danish University of Pharmaceutical Sciences., Nasal Administration of Sufentanil+Ketamine for Procedure-related Pain in Children, ClinicalTrials.gov, Jan. 12, 2010, Ketamine, NCT01047241.
Database Medline [Online] US National Library of Medicine (NLM), Bethesda, MD, US; Sep. 2010 (Sep. 2010), Okamoto Nagahisa et al: "Rapid antidepressant effect of ketamine anesthesia during electroconvulsive therapy of treatment-resistant depression: comparing ketamine and propofol anesthesia.", Database accession No. NLM19935085 abstract & The Journal of ECT Sep 2010, vol. 26, No. 3, Sep. 2010 (Sep. 2010), pp. 223-227.
Davidson, et al., Anesthesia and neurotoxicity to the developing brain: the clinical relevance, Pediatric Anesthesia, 2011, pp. 716-721, vol. 21.
Dawn., Drug Abuse Warning Network, 2011: National Estimates of Drug-Related Emergency Department Visits, National ED Estimates, 2011, pp. 1-100.
DE102007009888 A1 English Translation, Sep. 2008; Translated Jan. 26, 2015.
Deakin, et al., PharmacoMRI and cognitive effects of the potential antidepressant AZD6765 compared with ketamine in untreated major depressive disorder, Affective disorders and antidepressants—Antidepressants (clinical), 2012, pp. S264-S264, Abstract.
Debattista, et al., Acute Antidepressant Effects of Intravenous Hydrocortisone and CRH in Depressed Patients: A Double-Blind, Placebo-Controlled Study, Am J Psychiatry, Mar. 2, 2000, pp. 1334-1337, vol. 157 Issue 8.
Deisenhammer, et al., How Much Time Is Left for Intervention Between Consideration and Accomplishment of a Suicide Attempt?, J Clin Psychiatry, Mar. 25, 2008, pp. 19-24, vol. 70 Issue 1.
Denk, et al., FiGURE 1. Western Blot Analysis of Peripheral Blood Cells in a Study of (S)-Ketamine infusion for the treatment of Depressive Symptomsa, letters to the Editor, 2011, pp. 1-2.
Dennis Charney, Ketamine as a Rapid Treatment for Post-traumatic Stress Disorder (PTSD) (KetPTSD), ClinicalTrials.gov, Sep. 9, 2008, Ketamine, NCT00749203.
DeOlmos, Neuroscience, 2009, 164(3), 1347-1359.
Desseilles, et al., Assessing the Adequacy of Past Antidepressant Trails: A Clinician's Guide to the Antidepressant Treatment Response Questionnaire, J Clin Psychiatry, 2011, pp. 1152-1154, vol. 72 Issue 8.
Dewilde, et al., The promise of ketamine for treatment-resistant depression: current evidence and future directions, Ann. N.Y. Acad. Sci, 2015, pp. 1-11, page number.

Diamond, et al., Ketamine infusions for treatment resistant depression: a series of 28 patients treated weekly or twice weekly in an ECT clinic, Journal of Psychopharmacology, 2014, pp. 536-544, vol. 28 Issue 6.
Diaz, et al., Ineffectiveness of Repeated Intravenous Ketamine Infusions in Treatment-Resistant Depression After a Post-Ketamine Relapse:Time for a Rethink?, Journal of Clinical Psychopharmacology, 2018, pp. 1-2, Page Number.
Diazgranados et al, Rapid Resolution of Suicidal ideation After a Single Infusion of an N-Methyl-D Aspartate Antagonist in Patient With Treatment-Resistant Major Depressive Disorder, J Clin Psychiatry, 2010, pp. 1605-1611, vol. 71, Issue 12.
Diazgranados et al., A randomized add-on trial of an N-methyl-D-aspartate antagonist in treatment-resistant bipolar depression. Archives of general psychiatry 67, 2010, pp. 793-802.
Diazgranados Nancy et al: "Rapid resolution of suicidal ideation after a single infusion of an N-methyl-D-aspartate antagonist in patients with treatment-resistant major depressive disorder. Depression, fatigue and sleep disorders were relieved, anxiety and panic were reduced, and pain levels were drastically reduced", The Journal of Clinical Psychiatry Dec. 2010, vol. 71, No. 12, Dec. 2010 (Dec. 2010), pp. 1605-1611, XP8161411, ISSN: 1555-2101 the whole document.
Djupesland, et al., Breath Powered Nasal Delivery: A New Route to Rapid Headache Relief, Headache, Jun. 4, 2013, pp. 72-84, vol. 53 Supplementary 2.
Djupesland, Nasal Drug Delivery Devices: Characteristics and Performance in a Clinical Perspective—A Review. Drug Deliv. and Transl. Res. (2013) 3:42-64.
Djupesland., Nasal drug delivery devices: characteristics and performance in a clinical perspective—a review, Drug Deliv. and Transl. Res, Oct. 18, 2012, pp. 1-21.
Domino, et al., Pharmacologic effects of CI-581, a new dissociative anesthetic, in man, Clinical Pharmacology and Therapeutics, Jan. 4, 1965, pp. 279-291, vol. 6 Issue 3.
Donn W Ketcham MD., Where there is no anaesthesiologist; the many usus of ketamine, Tropical Doctor, 1990, pp. 163-166, vol. 20.
Doros, "A repeated measures model for analysis of continuous outcomes in sequential parallel comparison design studies", Stat. Med., 2013, 32(16), 2767-2789.
Dougals, et al., Practice Guideline for the Assessment and Treatment of Patients With Suicidal Behaviors, American Psychiatric Association Practice Guidelines, Jul. 28, 2003, pp. 1-120, page number.
Draft Guidance., Guidance for Industry Suicidal Ideation and Behavior: Prospective Assessment of Occurrence in Clinical Trials, Clinical/Medical, 2012, pp. 1-16, Revision 1.
Drevets, et al., Amphetamine-Induced Dopamine Release in Human Ventral Striatum Correlates with Euphoria, Biol Psychiatry, 2001, pp. 81-96, vol. 49.
Duman, et al., Synaptic Dysfunction in Depression: Potential Therapeutic Targets, Science, Oct. 5, 2012, pp. 68-72, vol. 338.
United States Naval Medical Center, San Diego., A Study to Decrease Suicidal Thinking Using Ketamine, ClinicalTrials.gov, Apr. 16, 2015, Ketamine, NCT02418702.
United States Naval Medical Center, San Diego., Subanesthetic IV Bolus Ketamine in the Treatment of Acute Depression, ClinicalTrials.gov, Mar. 4, 2015, Ketamine, NCT02378415.
Universidade Federal De Goias., Intranasal Sedation With Dexmedetomidine and Ketamine in Pediatric Dentistry (NASO II), ClinicalTrials.gov, Sep. 25, 2017, Ketamine, NCT03290625.
University Health Network, Toronto., Study of Ketamine for Depression in Cancer Patients Receiving Palliative Care, ClinicalTrials.gov, Jan. 25, 2018, Ketamine, NCT03410446.
University Hospital, Basel, Switzerland., Comparison of Oral Morphine Versus Nasal Ketamine Spray With Chitosan in Cancer Pain Outpatients (Onkemi), ClinicalTrials.gov, Oct. 29, 2015, ketamine, NCT02591017.
University Hospital, Basel, Switzerland., Pharmacokinetics and Pharmacodynamics of Nasally App.lied Esketamine, ClinicalTrials.gov, Feb. 19, 2009, Esketamine, NCT00847418.

(56) References Cited

OTHER PUBLICATIONS

University Hospital, Basel, Switzerland., The Analgesic Effect of Combined Treatment With Intranasal S-ketamine and Intranasal Midazolam (NASKEMI), ClinicalTrials.gov, Jan. 12, 2011, S-ketamine, NCT01275547.

University Hospital, Clermont-Ferrand., Ketamine and Neuropathic Pain (KETAPAIN), ClinicalTrials.gov, Jun. 10, 2015, Ketamine, NCT02467517.

University Hospital, Grenoble, Estimate the Efficiency of the Association of an Injection of Ketamine and the Venlafaxine in the Severe Major Depressive Disorder for Six Weeks (KETADEP), ClinicalTrials.gov, Mar. 19, 2012, Ketamine, NCT01557712.

University Hospital, Lille., Evaluation of the Initial Prescription of Ketamine and Milnacipran for Depression in Palliative Care (KETAPAL), ClinicalTrials.gov, May 26, 2016, Ketamine, NCT02783430.

University Hospital, Montpellier., Intranasal Midazolam Versus Intranasal Ketamine to Sedate Newborns for Intubation in Delivery Room, ClinicalTrials.gov, Jan. 25, 2012, Ketamine, NCT01517828.

University of Aarhus, Sensory Examination and Pharmacological Modulation of Oral Hyperexcitability in Patients With Atypical Odontalgia and Matched Healthy Controls, ClinicalTrials.gov, Jun. 21, 2005, S-ketamine, NCT00115102.

University of Aberdeen, The Use of Ketamine as an Anaesthetic During Electroconvulsive Therapy (KANECT), ClinicalTrials.gov, Mar. 2, 2011, Ketamine, NCT01306760.

University of Alabama at Birmingham, Treatment of Suicidal Ideation With Intravenous Ketamine Infusion, ClinicalTrials.gov, Jun. 27, 2013, Ketamine, NCT01887990.

University of Alabama at Birmingham., miRNAs, Suicide, and Ketamine—Plasma Exosomal microRNAs as Novel Biomarkers for Suicidality and Treatment Outcome, ClinicalTrials.gov, Apr. 16, 2015, Ketamine, NCT02418195.

University of Alberta., Effects of Low-dose Ketamine as an Adjunct to Propofol-based Anesthesia for Electroconvulsive Therapy, ClinicalTrials.gov, Oct. 19, 2015, Ketamine, NCT02579642.

University of Arizona., Intranasal Ketamine for Pediatric Procedural Sedation: a Feasibility Study, ClinicalTrials.gov, Mar. 1, 2017, Ketamine, NCT03067974.

University of British Columbia., Prehospital Analgesia With Intra-Nasal Ketamine (PAIN-K), ClinicalTrials.gov, Apr. 27, 2016, Ketamine, NCT02753114.

University of Calgary., Pre-hospital Care With Intra-Nasal Ketamine for Transport (PRECINKT): A Pilot Study (PRECINKT), ClinicalTrials.gov, Jan. 10, 2014, Ketamine, NCT02033434.

University of California, Davis, Ed Treatment of Suicidal Patients With Ketamine Infusion, ClinicalTrials.gov, Apr. 18, 2018, Ketamine, NCT03502551.

University of California, Los Angeles., Biomarkers of Fast Acting Therapies in Major Depression, ClinicalTrials.gov, Jun. 17, 2014, Ketamine, NCT02165449.

University of Cincinnati., Emergency Ketamine Treatment of Suicidal Ideation, ClinicalTrials.gov, Jul. 8, 2014, Ketamine, NCT02183272.

University of Glasgow., Ketamine Hydrochloride and Best Pain Management in Treating Cancer Patients With Neuropathic Pain, ClinicalTrials.gov, Mar. 16, 2011, Ketamine, NCT01316744.

University of Iowa., Intranasal Ketamine Versus Intramuscular Ketamine for Procedural Sedation in Pediatric Patients, ClinicalTrials.gov, Jul. 27, 2010, Ketamine, NCT01170247.

University of Manitoba, Hyperventilation Combined With Etomidate or Ketamine Anesthesia in ECT Treatment of Major Depression, ClinicalTrials.gov, Oct. 5, 2016, Ketamine, NCT02924090.

University of Massachusetts, Worcester., Memantine Augmentation of Antidepressants, ClinicalTrials.gov, Jun. 27, 2006, memantine, NCT00344682.

University of Michigan, Anesthesia and Functional Connectivity: An Analysis of fMRI Changes, ClinicalTrials.gov, Jul. 22, 2014, Anesthetics, NCT02196259.

University of Michigan, Relationship Between Postpartum Mood Disorders and Delivery Experience, ClinicalTrials.gov, Dec. 29, 2016, Postpartum Period, NCT03004872.

University of Minnesota . . . , Ketamine in Adolescents With Treatment-Resistant Depression, ClinicalTrials.gov, Mar. 5, 2014, Ketamine, NCT02078817.

University of Mississippi Medical Center., Ketamine: Its Effects on Suicidal Ideations and Inpatient Hospital Length of Stay, ClinicalTrials.gov, Dec. 20, 2016, Ketamine, NCT02997722.

University of Monastir., Ketamine Intra Nasal Traumatology (Ket), ClinicalTrials.gov, Jul. 28, 2017, Ketamine, NCT03233035.

University of New Mexico., Spreading Depolarization and Ketamine Suppression (SAKS), ClinicalTrials.gov, Jul. 17, 2015, Ketamine, NCT02501941.

University of Ottawa., Action of Ketamine in Treatment-Resistant Depression, ClinicalTrials.gov, Sep. 18, 2013, Ketamine, NCT01945047.

University of Padova., Ketamine in Bariatric Surgery, ClinicalTrials.gov, Nov. 12, 2012, Ketamine, NCT01724983.

University of Pennsylvania., Alternative Sedation During Bronchoscopy (DEX), ClinicalTrials.gov, Jul. 8, 2010, ketamine, NCT01158820.

University of Saskatchewan, Comparing Ketamine and Propofol Anesthesia for Electroconvulsive Therapy, ClinicalTrials.gov, Sep. 4, 2013, Ketamine, NCT01935115.

University of Saskatchewan., ECT With Ketamine Anesthesia vs High Intensity Ketamine With ECT Rescue for Treatment-Resistant Depression, ClinicalTrials.gov, Sep. 5, 2017, Ketamine, NCT03272698.

University of Saskatchewan., Efficacy of Opioid-free Anesthesia in Reducing Postoperative Respiratory Depression in Children Undergoing Tonsillectomy, ClinicalTrials.gov, Dec. 9, 2016, Ketamine, NCT02987985.

University of Tennessee Health Science Center., IN Ketamine Vs IN Midazolam and Fentanyl for Abscess I&D, ClinicalTrials.gov, Dec. 18, 2015, Ketamine, NCT02635282.

University of Turku, The Neural Mechanisms of Anesthesia and Human Consciousness (Part 6), ClinicalTrials.gov, Dec. 8, 2015, S-ketamine, NCT02624401.

University of Utah., Endogenous Opioid Modulation by Ketamine, ClinicalTrials.gov, Feb. 14, 2017, Ketamine, NCT03051945.

U.S. Appl. No. 16/727,594, Entitled "Val66Met (SNP rs6265) Methods for the Treatment of Depression"; filed Dec. 26, 2019.

VA Connecticut Healthcare System., Open Label Ketamine Treatment for Major Depressive Disorder in Veterans (Ket-MOD), ClinicalTrials.gov, Feb. 15, 2017, Ketamine, NCT03053830.

VA Office of Research and Development, Efficacy of Repeated Ketamine Infusions for Treatment-resistant Depression, ClinicalTrials.gov, Feb. 10, 2015, Ketamine, NCT02360280.

VA Office of Research and Development, Ketamine for the Rapid Treatment of Major Depressive Disorder and Alcohol Use Disorder, ClinicalTrials.gov, Jun. 3, 2015, Ketamine, NCT02461927.

VA Office of Research and Development., Ketamine for Treatment Resistant Late-Life Depression, ClinicalTrials.gov, Sep. 22, 2015, Ketamine, NCT02556606.

VA Puget Sound Health Care System., Ketamine Anesthesia for Improvement of Depression in ECT (KAID), ClinicalTrials.gov, Apr. 27, 2016, Ketamine, NCT02752724.

Valois., Unit-Dose Nasal Sprays:, Valois., 2004, pp. 1-2.

Venancio, et al., Impaired Spatial Memory after Ketamine Administration in Chronic Low Doses, Current Neuropharmacology, 2011, pp. 251-255, vol. 9 Issue 1.

AACAP Official Action., Practice Parameter for the Assessment and Treatment of Children and Adolescents With Suicidal Behavior, J. Am. Acad. Child Adolesc. Psychiatry, 2001, pp. 24S-51S, vol. 40 Supplementary 7.

Aan Het Rot, Marije et al., Safety and Efficacy of Repeated-Dose Intravenous Ketamine for Treatment-Resistant Depression, Biol Psychiatry, Aug. 27, 2009, pp. 139-145, vol. 67.

Abdallah, et al., ECT Attenuates the Rapid Antidepressant Effect of Ketamine, Biol Psychiatry, 2012, pp. 294S, vol. 71.

Abdallah, et al., Hippocampal volume and the rapid antidepressant effect of ketamine, Journal of Psychopharmacology, 2015, pp. 591-595, vol. 29 Issue 5.

(56) References Cited

OTHER PUBLICATIONS

Abdallah, et al., Ketamine Treatment and Global Brain Connectivity in Major Depression, Neuropsychopharmacology, 2017, pp. 1210-1219, vol. 42.
Abdallah, et al., The Nucleus Accumbens and Ketamine Treatment in Major Depressive Disorder, Neuropsychopharmacology, Mar. 29, 2017, pp. 1739-1746, vol. 42.
Abdallah, et al., The Rapid Antidepressant Effect of Ketamine in the Electroconvulsive Therapy Setting, J ECT, 2012, pp. 157-161, vol. 28 Issue 3.
Advivaryu, et al., Short Communication Genotoxic efforts of Ketamine on CHO cells, Arch Toxicol, Apr. 3, 1986, pp. 124-125, vol. 59.
Ahlander, Neuropsychopharmacol, 1999, 21, 414-426.
Ahn, et al., Proliposomes as an intranasal dosage form for the sustained delivery of propranolol, Journal of Controlled Release, Oct. 13, 1994, pp. 203-210, vol. 34.
Aiphs, et al., Comparative Validation of the ISST-Plus, the S-STS, and the C-SSRS for Assessing Suicidal Thinking and Behavior When Mapped to C-CASA (2010), Janssen Scientific Affairs, LLC, 2012, pp. 1-1, Poster.
Aitken, et al., Section of Measurement in Medicine., Proc. Roy. Soc. Med., 1969, pp. 989-993, vol. 62.
Al Shirawi, et al., Oral Ketamine in Treatment-Resistant Depression a Clinical Effectiveness Case Series, J Clin Psychopharmacol, 2017, pp. 464-467, vol. 37 Issue 4.
Albott, et al., Neurocognitive Effects of Repeated Ketamine Infusions in Co-Occurring Posttraumatic Stress Disorder and Treatment-Resistant Depression, Biological Psychiatry, May 15, 2017, pp. S405-S405, vol. 81.
Alessandri, et al., Effects of Ketamine on Tunnel Maze and Water Maze Performance in the Rat, Behavioral and Neural Biology, 1989, pp. 194-212, vol. 52.
Aligeti, et al., Rapid Resolution of Suicidal Behavior and Depression With Single Low-Dose Ketamine Intravenous Push Even After 6 Months of Follow-Up, Journal of Clinical Psychopharmacology, 2014, pp. 533-535, vol. 34 Issue 4.
Alison Goate, DPHIL., Changing the Equation for Alzheimer's, Mount Sinai Science & Medicine, 2018, pp. 1-2, Page Number.
Alizadeh, et al., Antidepressant Effect of Combined Ketamine and Electroconvulsive Therapy on Patients With Major Depressive Disorder: A Randomized Trial, Iran J Psychiatry Behav Sci, Sep. 23, 2015, pp. e1573-e1578, vol. 9 Issue 3.
Allen, et al., Screening for Suicidal Ideation and Attempts among Emergency Department Medical Patients: Instrument and Results from the Psychiatric Emergency Research Collaboration, Suicide and Life-Threatening Behavior, 2013, pp. 1-12.
Allen, et al., Serum BDNF as a peripheral biomarker of treatment-resistant depression and the rapid antidepressant response: A comparison of ketamine and ECT, Journal of Affective Disorders, Jul. 29, 2015, pp. 306-311, vol. 186.
Alosh, et al., A consistency-adjusted alpha-adaptive strategy for sequential testing, Statistics in Medicine, Apr. 8, 2010, pp. 1559-1571, vol. 29.
Alphs L, et al., Validation of Suicidal Ideation and Behavior Assessment Tool (SIBAT): Intra- and Inter-rater Reliability, European Symposium on Suicide & Suicidal Behavior (ESSSB), 2018, pp. 1-1, Poster 222.
Alphs, et al., "Comparative Validation of the ISST-Plus, the S-STS, and the C-SSRS for Assessing Suicidal Thinking and Behavior When Mapped to C-CASA (2010)", Janssen Scientific Affairs, LLC, 2012, pp. 1-1, Poster.
American Association of Suicidology., Facts About Suicide and Depression, American Association of Suicidology, 2010, pp. 1-4.
American Pharmaceutical Review, Controlled Release Roundtable, Lonza, Jun. 30, 2017, pp. 1-10.
Anand, et al., Attenuation of the Neuropsychiatric Effects of Ketamine With Lamotrigine., Arch Gen Psychiatry., 2000, pp. 270-276, vol. 57.
Anderson, et al., Evidence-based guidelines for treating depressive disorders with antidepressants: A revision of the 2000 British Association for Psychopharmacology guidelines, Journal of Psychopharmacology, 2008, pp. 343-396, vol. 22 Issue 4.
Anderson, et al., Ketamine augmentation of electroconvulsive therapy to improve neuropsychological and clinical outcomes in depression (Ketamine-ECT): a multicentre, double-blind, randomised, parallel-group, superiority trial, Lancet Psychiatry, Mar. 27, 2017, pp. 365-377, vol. 4.
Andine, J. Pharmacol. Exp. Ther., 1999, 290(3), 1393-1408.
Andrade, et al., Intranasal Drug Delivery in Neuropsychiatry: Focus on Intranasal Ketamine for Refractory Depression, J Clin Psychiatry, 2015, pp. e628-e631, vol. 76 Issue 5.
Angelica Lavito., Ketamine is emerging as a popular treatment for depression. New research suggests the drug acts like an opioid, Biotech and Pharmaceuticals, Aug. 29, 2018, pp. 1-5, N/a.
Angold, et al., Comorbidity, J.Child Psychol. Psychiat, 1999, pp. 57-87, vol. 40 Issue 1.
Angold, et al., Puberty and depression: the roles of age, pubertal status and pubertal timing, Psychological Medicine, 1998, pp. 51-61, vol. 28.
Angst, et al., Mortality of patients with mood disorders: follow-up over 34-38 years, Journal of Affective Disorders, Apr. 3, 2001, pp. 167-181, vol. 68.
Anna Meuronen, Md., Intranasal Esketamine and Fentanyl for Pain in Minor Trauma, ClinicalTrials.gov, Feb. 5, 2018, Esketamine, NCT03421275.
Anonymous: "NCT02133001 on Jun. 23, 2014; Clinical Trials.gov Archive", pp. 1-6, XP055230128, retrieved on the Internet: URL:https://clinicaltrails.gov/archie/NCT02133001/2014-06-23, retrieved on Nov. 20, 2015.
Asarnow, et al., Depression and role impairment among adolescents in primary care clinics, Journal of Adolescent Health, Nov. 4, 2004, pp. 477-483, vol. 37.
Asarnow, et al., Depression in Youth: Psychosocial Interventions, Journal of Clinical Child Psychology, Mar. 14, 2000, pp. 33-47, vol. 30 Issue 1.
Asarnow, et al., Effectiveness of a Quality Improvement Intervention for Adolescent Depression in Primary Care Clinics, JAMA, Jan. 19, 2005, pp. 311-319, vol. 293 Issue 3.
Asarnow, et al., Treatment of Selective Serotonin Reuptake Inhibitor-Resistant Depression in Adolescents: Predictors and Moderators of Treatment Response, J Am Acad Child Adolesc Psychiatry, Sep. 29, 2009, pp. 330-339, vol. 48 Issue 3.
Astrazeneca., Study Where Pharmaco Magnetic Resonance Imaging (MRI) Effects of AZD6765 Will be Compared to Placebo in Depressive Male and Female Subjects, ClinicalTrials.gov, Jan. 12, 2010, Ketamine, NCT01046630.
Aurora, "Development of Nasal Delivery Systems: A Review", Drug Development and Delivery, vol. 2, No. 7, Oct. 2002.
Aurora., Development of Nasal Delivery systems: A Review, Drug Development & Delivery, 2017, pp. 1-4, vol. 2 Issue 7.
Ayuso-Mateos, et al., Depressive disorders in Europe: prevalence figures from the Odin study, British Journal of Psychiatry, Apr. 6, 2001, pp. 308-3016, vol. 179.
Azevedo, et al., Transdermal Ketamine as an Adjuvant for Postoperative Analgesia After Abdominal Gynecological Surgery Using Lidocaine Epidural Blockade, Anesth Analg, Aug. 11, 2000, pp. 1479-1482, vol. 91.
Baji, et al., Age and Sex Analyses of Somatic Complaints and Symptom Presentation of Childhood Depression in a Hungarian Clinical Sample, J Clin Psychiatry, 2009, pp. 1467-1472, vol. 70 Issue 10.
Baldessarini, et al., Decreased risk of suicides and attempts during long-term lithium treatment: a meta-analytic review, Bipolar Disorders, Mar. 13, 2006, pp. 625-639, vol. 8.
Ballard, et al., Improvement in suicidal ideation after ketamine infusion: Relationship to reductions in depression and anxiety, Journal of Psychiatric Research, Jul. 31, 2014, pp. 161-166, vol. 58.
Ballard, et al., Neural Correlates of Suicidal Ideation and Its Reduction in Depression, International Journal of Neuropsychopharmacology, 2015, pp. 1-6.
Barbe, et al., Suicidality and Its Relationship to Treatment Outcome in Depressed Adolescents, Suicide and Life-Threatening Behavior, Aug. 15, 2003, pp. 44-55, vol. 34 Issue 1.

(56) References Cited

OTHER PUBLICATIONS

Auer, R.N, Coulter, K.C., 1994. The nature and time course of neuronal vacuolation induced by the N-methyl-D-aspartate antagonist MK-801. Acta Neuropathol. 87, 1-7.

Auer, R.N., 1996. Effect of age and sex on N-methyl-D-aspartate antagonist-induced neuronal necrosis in rats. Stroke 27, 743-746.

Aulton M E: Pharmaceutics, The Science of Dosage Form Design, 254-258; 262-268; 1988, 485-490, 34 pages.

Aulton, Michael: Aulton's Pharmaceutics; Dosage Form Design and Manufacture, 3rd Edition; 2008, (368-369) 4 pages.

Begec et al: Rev Bras Anestesiol, the antimicrobial effects of ketamine combined with propofol: An in vitro study, 2013, 63(6): 461-465.

Bender, Neurotoxicology and Teratology, 2010b, 32, 542-550.

Bentley, William E.: Ketamine: an update for its use in complex regional pain syndrome and major depressive disorder; Clinical & Experimental Pharmacology (2015), 5(2), 1000169/1-1000169/3.

Berlim, et al., Definition, Assessment, and staging of Treatment-Resistant Refractory Major Depression: A Review of Current Concepts and Methods, Can J Psychiatry, 2007, pp. 46-54, vol. 52 Issue 1.

Bitter, Christoph: Transmucosal Nasal Drug Delivery: Pharmacokinetics and Pharmacodynamics of Nasally Applied Esketamine, Inauguraldissertation, zurErlangung der Würde eines Doktors der Philosophie vorgelegt der Philosophisch-Naturwissenschaftlichen Fakultat der Universität Basel Basel 2011, 1-208.

Bloch, Michael H: Effects of Ketamine in Treatment-Refractory Obsessive-Compulsive Disorder; Biological Psychiatry (2012), 72(11), 964-970.

Bueno, Experimental and Toxicologic Pathology, 2003, 54, 319-334.

Chang et al., "Biotransformation and Disposition of Ketamine, Biotransformation and Disposition of Ketamine", N.A., pp. 157-177.

Clinical Trials.gov Identifier: NCT02133001, May 7, 2014, URL:https://clinicaltrials.gov/ct2/show/NCT02133001.

Colbourne, F., Rakic, D., Auer, R.N., 1999. The effects of temperature and scopolamine on N-methyl-D-aspartate antagonist-induced neuronal necrosis in the rat. Neurosc. 90(1), 87-94.

Corya et al., Journal of Clinical Psychiatry, 2003, 64(11), 1349-1356.

De Olmos, S., Bueno, A., Bender, C., Lorenzo, A., de Olmos, J., 2008. Sex differences and influence of gonadal homones on MK801-induced neuronal degeneration in the granular retrosplenial cortex of the rat. Brain Struct. Funct. 213, 229-238.

European Medicines Agency Inspections (EMEA); Guideline on Excipients in the Dossier for Application for Marketing Authorisation of a Medicinal Product; London, Jun. 19, 2007, Doc. Ref. EMEA/CHMP/QWP/396951/2006; 12 pages.

European Pharmacopoeia—7th Edition; Published Jul. 15, 2010; 11 pages.

Farber, N.B., Wozniak, D.F., Price, M.T., Labruyere, J., Huss, J., St Peter, H., Olney, J.W., 1995. Age-specific neurotoxicity in the rat associated with Nmda receptor blockade: potential relevance to schizophrenia? Biol. Psychiatry 38, 788-796.

FDA Anesthetic and Life Support Drugs Advisory Committee (ALSDAC), Center for Drug Evaluation and Research, Silver Springs, MD, Mar. 10, 2011. "Ketamine and the Neonatal Brain: Rat Pups vs. Babies." on FDA website in archives Guest Presentation Mar. 10, 2011 pp. 1-76.

Feder, et al: Efficacy of intravenous ketamine for treatment of chronic posttraumatic stress disorder a randomized clinical trial; JAMA Psychiatry (2014), 71(6), 681-688.

Fix, A.S., Horn, J.W., Wightman, K.A., Johnson, C.A., Long, G.G., Storts, R.W., Farber, N., Wozniak, D.F., Olney, J.W., 1993 Neuronal vacuolation and necrosis induced by the noncompetitive N-methyl-D-aspartate (NMDA) antagonist MK(+)801 (dizocilpine maleate): a light and electron microscopic evaluation of the rat retrosplenial cortex. Exp. Neurol. 123, 204-215.

Fix, A.S., Long, G.G., Wozniak, D.F., Olney, J.W., 1994. Pathomorphologic effects of N-methyl-D-aspartate antagonists in the rat posterior cingulate/retrosplenial cerebral cortex: a review. Drug Development Res. 32, 147-152.

Fix, A.S., Ross, J.F., Stitzel, Sr., Switzer, R.C., 1996. Integrated evaluation of central nervous system lesions: stains for neurons, astrocytes, and microglia reveal the spatial and temporal features of MK-801-induced neuronal necrosis in the rat cerebral cortex. Toxicol. Pathol. 24(3), 291-304.

Fix, A.S., Stitzel, S.R., Ridder, G.M., Switzer, R.C., 2000. MK-801 neurotoxicity in cupric silver-stained sections: lesion reconstruction by 3-dimensional computer image analysis. Toxicol. Pathol. 28(1), 84-90.

Fix, A.S., Wozniak, D.F., Truex, J.L., McEwen, M., Miller, J.P., Olney, J.W., 1995. Quantitative analysis of factors influencing neuronal necrosis induced by MK-801 in the rat posterior cingulate/retrospenial cortex. Brain Res. 696, 194-204.

Gennaro, Alfonso: Remington: The Science and Practice of Pharmacy, 20th ed., 2000, pp. 1042-1047.

Gingerich HCP Live, https://www.mdmag.com/medical-news, Sep. 4, 2018.

Gonzalo Laje, Brain-Derived Neurotrophic Factor VAL66MET Polymorphism and Antidepressant Efficacy of Ketamine in Depressed Patients; Biol Psychiatry, Dec. 1, 2012,vol. 72, NR:11, pp. 1-4 (E27-E28), URL, https://www.ncbi.nlm.nih.gov/pmc/articles/PMC3786174/.

Guy, Clinical Global Impression of Severity (CGI-S) scale (Guy, "ECDEU Assessment Manual for Psychopharmacology—Revised (DHEW Publ No. Adm 76-338)" Rockville, MD: U.S. Department of Health, Education and Welfare, Public Health Service, Alcohol, Drug Abuse and Mental Health Administration, NIMH Psychopharmacology Research Branch, Division of Extramural Research Programs; 1976, pp. 218-222.

Hoffman, Pharmacology, Biochemistry and Behavior, 2003, 74, 933-941.

Horvath, Brain Res., 1997, 753(2), 181-195.

Howland R.H., Journal of Psychosocial Nursing and Mental Health Services, 2008, 46(10), 21-24.

Hur, Environmental Toxicology and Pharmacology, 1999, 7, 143-146.

Ito, Wataru: Observation of Distressed Conspecific as a Model of Emotional Trauma Generates Silent Synapses in the Prefrontal-Amygdala Pathway and Enhances Fear Learning, but Ketamine Abolishes those Effects; Neuropsychopharmacology (2015), 40(11), 2536-2545 Apr. 13, 2015.

Jevtovic-Todorovic, V., Benshoff, N., Olney, J.W., 2000. Ketamine potentiates cerebrocortical damage induced by the common anesthetic agent nitrous oxide in adults rats. Br. J. Pharmacol. 130, 1692-1698.

Jevtovic-Todorovic, V., Carter, L.B., 2005. The anesthetics nitrous oxide and ketamine are more neurotoxic to old than to young rat brain. Neurobiology of Aging. 26, 947-956.

Jevtovic-Todorovic, V., Kirby, C.O., Olney, J., 1997. Isoflurane and Propofol Block Neurotoxicity Caused by MK-801 in the Rat Posterior Cingulate/Retrosplenial Cortex. Journal of Cerebral Blood Flow and Metabolism 17,168-174.

Jevtovic-Todorovic, V., Wozniak, D.F., Benshoff, N.D., Olney, J.W., 2001. A comparative evaluation of the neurotoxic properties of ketamine and nitrous oxide. Brain Res. 895, 264-267.

Journal of Clinical and Experimental Medicine (Igaku No Ayumi), 2006, vol. 219, No. 13, p. 949-953.

Juven-Wetzler, Alzbeta: Immediate ketamine treatment does not prevent posttraumatic stress responses in an animal model for PTSD; European Neuropsychopharmacology (2014), 24(3), 469-479.

Ketalar 10mg/ml Injection; Summary of Product Characteristics (SmPC), Mar. 17, 2020, 8 pages.

Ketanest S, Pfizer, Fachinformation, Jan. 2019, 5 pages.

Khalili-Mahani, N: Effect of subanaesthetic ketamine on plasma and saliva cortisol secretion; British Journal of Anaesthesia (2015), 115(1), 68-75 Published: May 16, 2015.

(56) References Cited

OTHER PUBLICATIONS

Kron, Miriam: Brain activity mapping in Mecp2 mutant mice reveals functional deficits in forebrain circuits, including key nodes in the default mode network, that are reversed with ketamine treatment; Journal of Neuroscience (2012), 32(40), 13860-13872.
Liman, Suryamin: Preventive treatment with ketamine attenuates the ischaemia-reperfusion response in a chronic postischaemia pain model; Oxidative Medicine and Cellular Longevity (2015) 380403/1-380403/9 Jun. 16, 2015 Published online Jun. 16, 2015.
Liu, Xing-qing; Hu, Xu-dong; Zhang, Wen-li; Ling, Chen; Lin, Jin-bing; Du, Shun-yan, Influence of preinjection of small dose ketamine on Edinburgh postnatal depression scale of cesarean section women, Guangdong Yixue (2013), 34(12), 1917-1919 (Abstract).
Lu, Li-ling, Effect of maternal pre-injection of low dose amphetamine on postpartum depression score in cesarean section, Yixue Zongshu (2015), 21 (24), 4570-4572 (Abstract).
Ma, Jingyi: Deep brain stimulation of the medial septum or nucleus accumbens alleviates psychosis-relevant behavior in ketamine-treated rats; Behavioural Brain Research (2014), 266, 174-182.
Maruff P, Werth J, Giordani B, Caveney, AF, Feltner D, Snyder PJ. A statistical approach for classifying change in cognitive function in individuals following pharmacologic challenge: an example with alprazolam Psychopharmacology 2006; 186: 7-17.
Nakako, Tomokazu: Effects of lurasidone on ketamine-induced joint visual attention dysfunction as a possible disease model of autism spectrum disorders in common marmosets; Behavioural Brain Research (2014), 274, 349-354.
Niciu, Mark J: Two cases of delayed-onset suicidal ideation, dysphoria and anxiety after ketamine infusion in patients with obsessive-compulsive disorder and a history of major depressive disorder; Journal of Psychopharmacology (London, United Kingdom) (2013), 27 (7), 651-654.
Okayama Igakkai Zasshi (Journal of Okayama Medical Association), 2008, vol. 119, p. 315-317.
Olney, J.W., Labruyere, J., Price, M.T., 1989. Pathological changes induced in cerebrocortical neurons by phencyclidine and related drugs. Science 240, 1360-1362.
Olney, J.W., Labruyere. J., Wang, G., Wozniak, D.F., Price, M.T., Sesma, M.A., 1991. NMDA antagonist neurotoxicity: mechanism and prevention. Science 254, 1515-1518.
Remington: The Science and Practice of Pharmacy; 20th Edition; Chapter 78, p. 1398, 2000, (3pp).
Rodriquez, et al: Randomized Controlled Crossover Trial of Ketamine in Obsessive-Compulsive Disorder: Proof-of-Concept Rodriguez; Neuropsychopharmacology (2013), 38(12), 2475-2483.
Rowe et al: Handbook of Pharmaceutical Excipients, Sixth Edition, 2009, pp. 181-183; 247-250.
Rush, CNS Drugs, 2009, 23(8), 627-647.
Sanli, et al: The effect of addition of ketamine to lidocaine on postoperative pain in rhinoplasties; Turkish Journal of Medical Sciences (2016), 46(3), Aug. 9, 2015, pp. 789-794.
Schoenenberg, Michael: Effects of peritraumatic ketamine medication on early and sustained posttraumatic stress symptoms in moderately injured accident victims; Germany Psychopharmacology (Berlin, Germany) (2005), 182 (3), 420-425.
Slomski, Anita; Ketamine effective in treating PTSD; The Journal of the American Medical Association (2014), 312(4), 327.
Study NCT01998958; A Double-Blind, Doubly-Randomized, Placebo-Controlled Study of Intranasal Esketamine in an Adaptive Treatment Protocol to Assess Safety and Efficacy in Treatment-Resistant Depression (SYNAPSE); Submitted Date: Feb. 14, 2014 (v2).
Study NCT01998958; A Double-Blind, Doubly-Randomized, Placebo-Controlled Study of Intranasal Esketamine in an Adaptive Treatment Protocol to Assess Safety and Efficacy in Treatment-Resistant Depression (SYNAPSE); Submitted Date: Mar. 18, 2014 (v3).
Study NCT01998958; A Double-Blind, Doubly-Randomized, Placebo-Controlled Study of Intranasal Esketamine in an Adaptive Treatment Protocol to Assess Safety and Efficacy in Treatment-Resistant Depression (SYNAPSE); Submitted Date: Nov. 25, 2013 (v1).
Study NCT02133001; A Double-blind, Randomized, Placebo Controlled Study to Evaluate the Efficacy and Safety of Intranasal Esketamine for the Rapid Reduction of the Symptoms of Major Depressive Disorder, Including Suicidal Ideation, in Subjects Who Are Assessed to be at Imminent Risk for Suicide; Submitted Date: May 6, 2014 (v1).
Wilcock, et al: Therapeutic Reviews, Journal of Pain and Symptom Management, vol. 41, No. 3, Mar. 3, 2011, 640-649.
Willis, C.L., Ray, D.E., 2007. Antioxidants attenuate MK-801-induced cortical neurotoxicity in the rat. NeuroToxicology 28, 161-167.
Wilson, Pharmacology, Biochemistry and Behavior 81, 2005, 530-534.
Wozniak, Neurobiology of Disease, 1998, 5(5), 305-322.
Wozniak, Psychopharmacology, 1990, 101(1), 47-56.
Wu, et al., Transgenerational impairment of hippocampal Akt-mTOR signaling and behavioral deficits in the offspring of mice that experience postpartum depression-like illness. Progress in Neuro-Psychopharmacology & biological Psychiatry (2017), 73, 11-18.
Xia, et al., Chronic stress prior to pregnancy potentiated regulated by Akt-mTOR signaling in the hippocampus. Scientific Reports (2016), 6, 35042.
Xu, et al., Single bolus low-dose of ketamine does not prevent postpartum depression: a randomized, double-blind, placebo-controlled, prospective clinical trial. Archives of Gynecology and Obstetrics (2017), 295, 1167-1174.
Yang et al., "Serum Interleukin-6 is a predictive biomarker for ketamines antidepressant effect in treatment-resistant patients with major depression", Biological Psychiatry 77, 2015, pp. e19-e20.
Yazdi, Bijan; Comparison of additive oral Clonidine with Ketamine, on post-operative pain and hemodynamic in cataract extraction under topical anesthesia and sedation; Pharmaceutical and Biomedical Sciences (2015), 4(5), 37-42.
Zajackowski, Neurotox. Res., 2000, 1(4), 299-310.
Zhang, Li-Ming: Anxiolytic effects of ketamine in animal models of posttraumatic stress disorder; Psychopharmacology (Heidelberg, Germany) (2015), 232 (4), 663-672 Sep. 18, 2014.
Zhang, X., Boulton, A.A., Zuo, D.M., Yu, P.H., 1996. MK-801 induces apoptotic neuronal death in the rat retrosplenial cortex: prevention by cycloheximide and R(-)-2-hexyl-methylpropargylamine. J. Neurosc. Res. 46, 82-89.

* cited by examiner

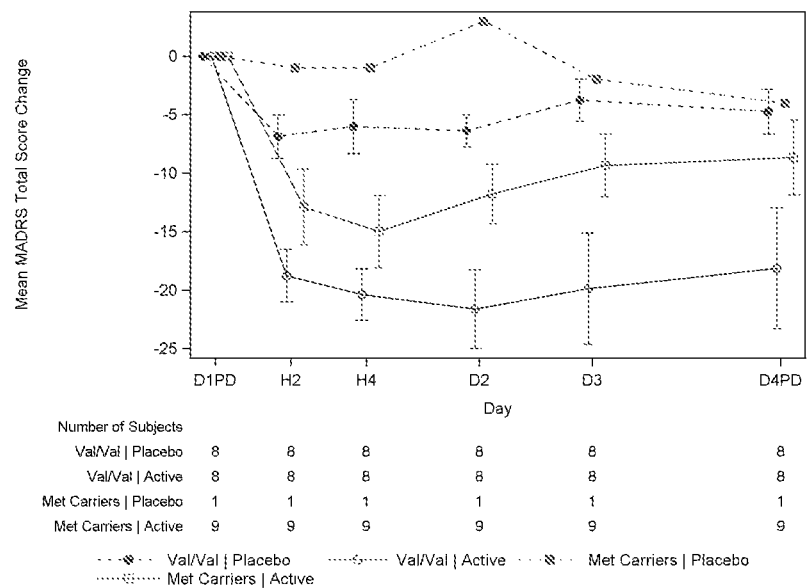
Figure 1: Mean changes in MADRS total score from baseline after the 1st infusion by Val/Val or Met carriers and by placebo or active

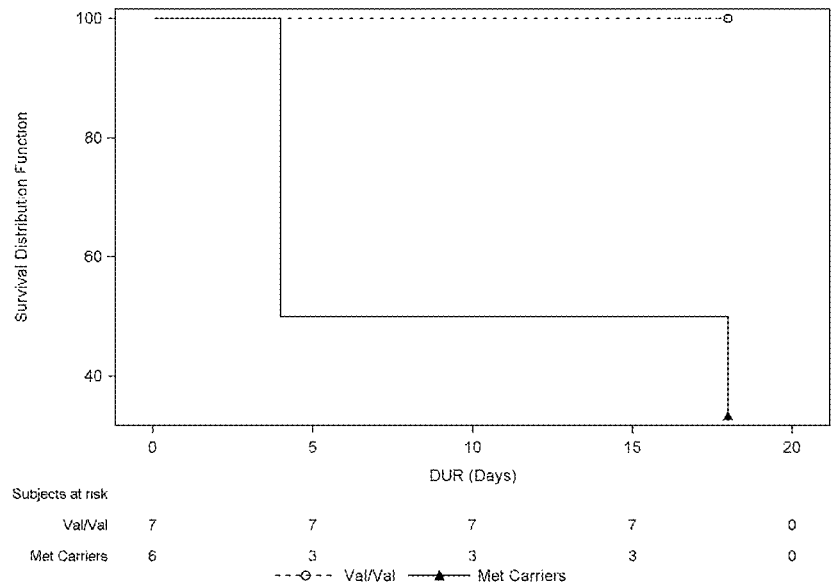
Figure 2: The survival curves for the duration of response in esketamine responders per day 1 randomization after Day 17 by Val/Val or Met carriers
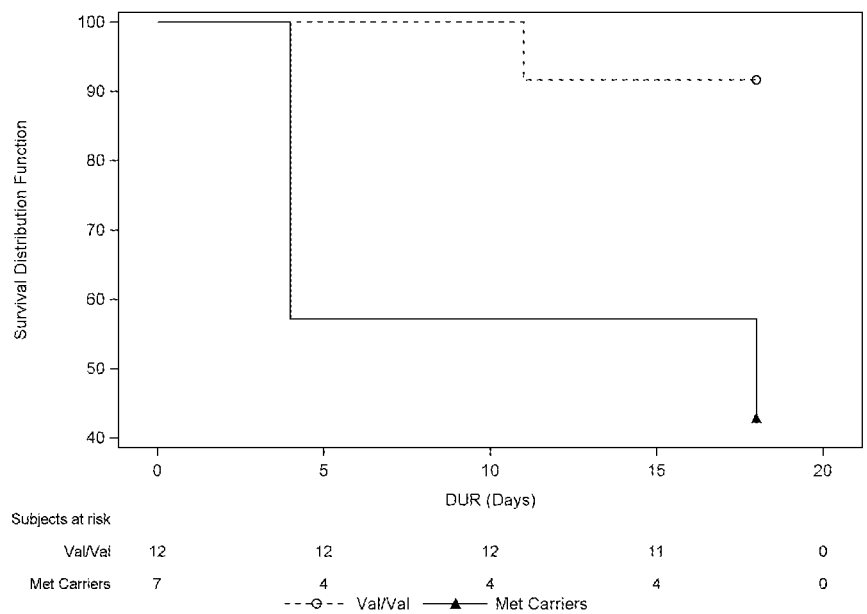
Figure 3: Survival curves for duration of response by Val/Val or Met carriers in all responders to esketamine after Day 17

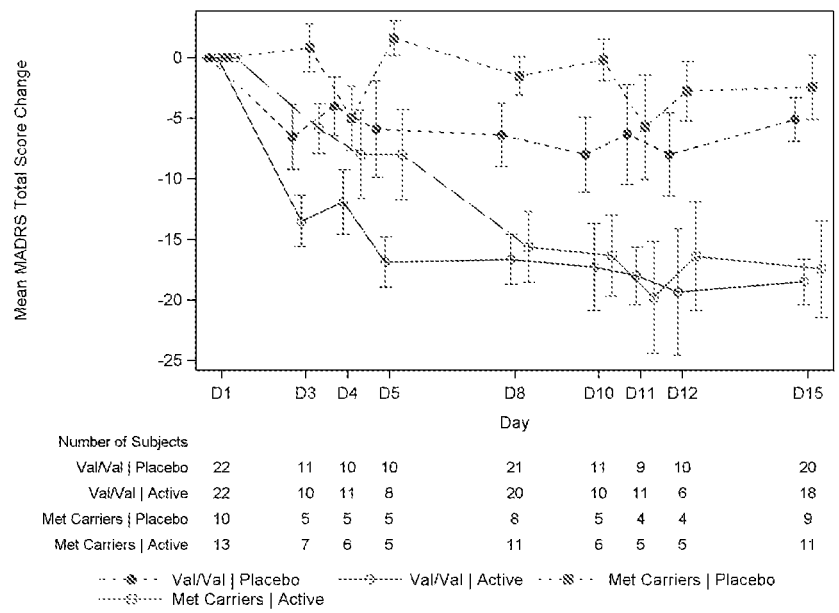
Figure 4: Mean changes in MADRS total scores from baseline over time up to Day 15 by Val/Val or Met carriers and by ketamine or placebo

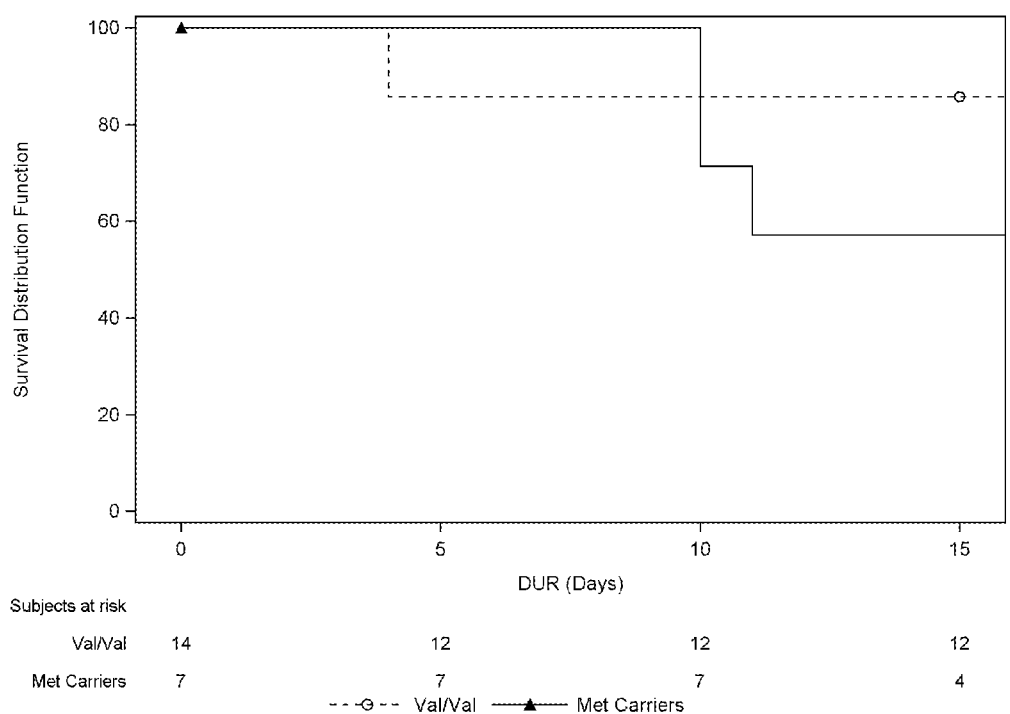
Figure 5: Survival curves for the duration of response Day 29 and up to Day 44 by Val/Val or Met carriers in ketamine responders

METHODS FOR THE TREATMENT OF DEPRESSION

CROSS REFERENCE TO RELATED APPLICATIONS

This application is a continuation of U.S. patent application Ser. No. 14/853,351, filed Sep. 14, 2015, which claims the benefit of priority under 35 U.S.C. § 119(e) to U.S. Provisional Patent Application 62/050,439, filed Sep. 15, 2014, the disclosures of which are herein incorporated by reference in their entireties.

SEQUENCE LISTING

The instant application contains a Sequence Listing which has been submitted electronically in ASCII format and is hereby incorporated by reference in its entirety. Said ASCII copy, created on Dec. 20, 2019, is named 103693.002128 SL.txt and is 2,566 bytes in size.

FIELD OF THE INVENTION

The present invention is directed to methods and dosing regimens for the treatment of depression (preferably treatment resistant depression), for the treatment of depression in a suicidal patient, and/or for the treatment and/or prevention of suicidality (e.g. suicidal ideations) comprising genotyping a patient to determine their Val66Met rs6265 polymorphism in BDNF and administering a ketamine, preferably esketamine, preferably intranasal esketamine, according to a dosing regimen matched to the patient's genotype.

BACKGROUND OF THE INVENTION

Major Depressive Disorder is defined as the presence of one of more major depressive episodes that are not better accounted for psychotic disorder or bipolar disorder. A major depressive episode is characterized by meeting five or more of the following criteria during the same 2 week period which represent a change in functioning and include at least depressed/sad mood or loss of interest and pleasure, indifference or apathy, or irritability and is usually associated with a change in a number of neurovegetative functions, including sleep patterns, appetite and body weight, motor agitation or retardation, fatigue, impairment in concentration and decision making, feelings of shame or guilt, and thoughts of death or dying (Harrison's Principles of Internal Medicine, 2000). Symptoms of a depressive episode include depressed mood; markedly diminished interest or pleasure in all, or almost all, activities most of the day; weight loss when not dieting or weight gain, or decrease or increase in appetite nearly every day; insomnia or hypersomnia nearly every day; psychomotor agitation or retardation nearly every day; fatigue or loss of energy nearly every day; feelings of worthlessness or excessive or inappropriate guilt nearly every day; diminished ability to think or concentrate, or indecisiveness, nearly every day; recurrent thoughts of death, recurrent suicidal ideation without a specific plan, or a suicide attempt or a specific plan for committing suicide. Further, the symptoms cause clinically significant distress or impairment in social, occupational, or other important areas of functioning. (*Diagnostic and Statistical Manual of Mental Disorders*, 4th Edition, American Psychiatric Association, 1994)

Current treatment options for unipolar depression include monotherapy or combination therapy with various classes of drugs including mono-amine oxidase inhibitors (MAOI), tricyclic antidepressants (TCA), serotonin specific reuptake inhibitors (SSRI), serotonin noradrenergic reuptake inhibitors (SNRI), noradrenaline reuptake inhibitor (NRI), "natural products" (such as Kava-Kava, St. John's Wort), dietary supplement (such as s-adenosylmethionine) and others. More specifically, drugs used in the treatment of depression include, but are not limited to imipramine, amitriptyline, desipramine, nortriptyline, doxepin, protriptyline, trimipramine, maprotiline, amoxapine, trazodone, bupropion, chlomipramine, fluoxetine, citalopram, sertraline, paroxetine, tianeptine, nefazodone, venlafaxine, desvenlafaxine, duloxetine, reboxetine, mirtazapine, phenelzine, tranylcypromine, and/or moclobemide. Several of these agents including, but not limited to, serotonin reuptake inhibitors are also used when depression and anxiety co-exist, such as in anxious depression.

In the clinic, 40-50% of depressed patients who are initially prescribed antidepressant therapy do not experience a timely remission of depression symptoms. This group typifies level 1 treatment-resistant depression, that is, a failure to demonstrate an "adequate" response to an "adequate" treatment trial (that is, sufficient intensity of treatment for sufficient duration). Moreover, about approximately 30% of depressed patients remain partially or totally treatment-resistant to at least two antidepressant treatments including combination treatments. Increasingly, treatment of treatment-resistant depression includes augmentation strategies including treatment with pharmacological agents such as, antipsychotics (such as quetiapine, aripiprazole, olanzapine, risperidone, and the like), lithium, carbamazepine, and triiodothyronine, and the like; adjunctive electroconvulsive therapy; adjunctive transcranial magnetic stimulation; etc.

Suicide, also known as completed suicide, is the "act of taking one's own life". Attempted suicide or non-fatal suicidal behavior is self-injury with the desire to end one's life that does not result in death. Suicidal ideation is the medical term for thoughts about or an unusual preoccupation with suicide, or thoughts of ending one's life or not wanting to live anymore but not necessarily taking any active efforts to do so.

The range of suicidal ideation varies greatly from fleeting to chronic and progress to detailed planning, role playing, and unsuccessful attempts, which may be deliberately constructed to fail or be discovered, or may be fully intended to result in death. Although not all who have suicidal ideation go on to make suicide attempts, a significant proportion do. Suicidal ideation is generally associated with depression (at about 60-70% of all cases).

Suicidal ideation which may include, for example, suicidal thoughts, may also include other related signs and symptoms. Some symptoms or co-morbid conditions may include unintentional weight loss, feeling helpless, feeling alone, excessive fatigue, low self-esteem, presence of consistent mania, excessively talkative, intent on previously dormant goals, feel like one's mind is racing. The onset of symptoms like these with an inability to get rid of or cope with their effects, a possible form of psychological inflexibility, is one possible trait associated with suicidal ideation. They may also cause psychological distress, which is another symptom associated with suicidal ideation. Symptoms like these related with psychological inflexibility, recurring patterns, or psychological distress may in some cases lead to the onset of suicidal ideation. Other possible symptoms and warning signs include: hopelessness, anhedonia, insomia, depression, severe anxiety, angst, impaired concentration, psychomotor agitation, panic attack and severe remorse.

Scales used in the evaluation of suicidal ideation include Beck Scale for Suicide Ideation (BSS), Columbia Suicide Severity Rating Scale (C-SSRS), Suicidal Ideation and Behavioral Assessment Tool (SIBAT) and The Kessler Psychological Distress Scale (K10, which test does not measure suicidal ideation directly, but there may be value in its administration as an early identifier of suicidal ideation. High scores of psychological distress are also, in some cases associated with suicidal ideation.

There are also several psychiatric disorders that appear to be comorbid with suicidal ideation or considerably increase the risk of suicidal ideation. The following disorders have been shown to be the strongest predictors of suicidal ideation/disorders in which risk is increased to the greatest extent: major depressive disorder (MDD), dysthymia, bipolar disorder. The main treatments for suicidality and/or suicidal ideation include: hospitalization, outpatient treatment, and medication. Hospitalization allows the patient to be in a secure, supervised environment to prevent their suicidal ideation from turning into suicide attempts. In most cases, individuals have the freedom to choose which treatment they see fit for themselves. However, there are several circumstances in which individuals can be hospitalized involuntarily, per state law including circumstances where an individual poses danger to self or others and where an individual is unable to care for one's self.

Outpatient treatment allows individuals to remain at their place of residence and receive treatment when needed or on a scheduled basis. Before allowing patients the freedom that comes with outpatient treatment, physicians evaluate several factors of the patient. These factors include the patient's level of social support, impulse control and quality of judgment. After the patient passes the evaluation, they are often asked to consent to a "no-harm contract". This is a contract formulated by the physician and the family of the patient. Within the contract, the patient agrees not to harm themselves, to continue their visits with the physician, and to contact the physician in times of need. These patients are then checked on routinely to assure they are maintaining their contract and staying out of troublesome activities.

There are also a number of different pharmacological treatment options for those experiencing suicidal ideation. However, prescribing medication to treat suicidal ideation can be difficult. One reason for this is because many medications lift patients' energy levels before lifting their mood. This puts them at greater risk of following through with attempting suicide. Additionally, if a patient has a co-morbid psychiatric disorder, it may be difficult to find a medication that addresses both the psychiatric disorder and suicidal ideation. Therefore, the medication prescribed to one suicidal ideation patient may be completely different than the medication prescribed to another patient. Although research is largely in favor of the use of antidepressants for the treatment of suicidal ideation associated with depression, in some cases antidepressants are claimed to be associated with increased suicidal ideation. Upon the start of using antidepressants, many clinicians will note that sometimes the sudden onset of suicidal ideation may accompany treatment. This has caused the Food and Drug Administration (FDA) to issue a warning stating that sometimes the use of antidepressants may actually increase the thoughts of suicidal ideation.

Ketamine (a racemic mixture of the corresponding S- and R-enantiomers) is an NMDA receptor antagonist, with a wide range of effects in humans, depending on the dose, including for example, analgesia, anesthesia, hallucinations, dissociative effects, elevated blood pressure and bronchodilation. Ketamine is primarily used for the induction and maintenance of general anesthesia. Other uses include sedation in intensive care, analgesia (particularly in emergency medicine and treatment of bronchospasms. Ketamine has also been shown to be efficacious in the treatment of depression (particularly in those who have not responded to other anti-depressant treatment). In patients with major depressive disorders, ketamine has additionally been shown to produce a rapid antidepressant effect, acting within two hours.

The S-ketamine enantiomer (or S-(+)-ketamine or esketamine) has higher potency or affinity for the NMDA receptor and thus potentially allowing for lower dosages; and is available for medical use under the brand name KETANEST S in some countries.

Brain-derived neurotropic factor (BDNF) is a secreted protein that, in humans, is encoded by the BDNF gene. BDNF is a member of the "neurotrophin" family of growth factors, which are related to the canonical "nerve growth factor", NGF. BDNF acts on certain neurons of the central nervous system (CNS) and the peripheral nervous system (PNS), helping to support the survival of existing neurons, and encourage the growth and differentiation of new neurons and synapses. In the brain, it is active in the hippocampus, cerebral cortex, and basal forebrain—areas vital to learning, memory, and higher thinking. BDNF is also is important for long-term memory. The BDNF protein is coded by the gene that is also called BDNF. In humans this gene is located on chromosome 11. Val66Met (rs6265) is a single nucleotide polymorphism in the gene where adenine and guanine alleles vary, resulting in a variation between valine (Val) and methione (Met) at codon 66.

A decrease in brain-derived neurotrophic factor (BDNF) expression in medial prefrontal cortex (mPFC) and other regions has given rise to the BDNF hypothesis of major depression. The human polymorphism in the BDNF gene, which leads to a valine-to-methionine substitution in the proBDNF protein at codon 66 (Val66Met), is carried by approximately 30% of the general Caucasian population (and approximately by 60-80% of the Asian population) and has been associated with mild cognitive deficits and possibly decreased hippocampal volume. In addition, individuals who carry the Met polymorphism have been reported to have an increased risk of stress-related major depression. The Val66Met polymorphism impairs activity dependent secretion of BDNF at synaptic sites and reduces intracellular trafficking of BDNF messenger RNA (mRNA) to dendrites.

The Val66Met polymorphism of BDNF has been registered in the dbSNP as rs6265 [*Homo sapiens*], occurring on the 11:27658369 chromosome and defined by the following sequence, SEQ. ID. No. 1:

ATCATTGGCTGACACTTTCGAACAC[A/G]TGA-TAGAAGAGCTGTTGGATGAGGA where [A/G] defines the position of the mutation.

Standard antidepressants, electroconvulsive therapy, and brain stimulation techniques such as transcranial magnetic stimulation all increase peripheral BDNF levels; also exercise has BDNF secretion-enhancing effects.

In a letter to the editor published in the peer-reviewed journal Biological Psychiatry, LAJE, G., Biol. Psychiatry, 2012 report on an analysis of the effect of rs6265 (Val66Met SNP) on the response to ketamine in patients experiencing a major depressive episode. The results "suggest that major depressive disorder (MDD) patients with the Val/Val BDNF allele at rs6265 are more likely to exhibit antidepressant response to ketamine than Met carriers." This effect was initially hinted at by LIU, R-Y., Biol. Psychiatry, 2012, pp 996-1005, Vol. 71, who also suggested that Met/Met knocked in mice displayed blunted antidepressant-like response to ketamine compared to Val/Val mice, as well as reduced synaptogenesis (LIU, R-Y., et al.). Altogether, this evidence further suggests that determining the BDNF rs6265 genotype might be associated with likelihood of response to ketamine and that it may be possible to separate subjects with a higher likelihood of response to ketamine based on this genotype.

There remains a need to provide an effective treatment for depression, more particularly treatment resistant depression and/or for the treatment of suicidality, suicidal ideations, and for the prevention of suicide, particularly in the first hours and days after the onset of highly suicidal ideation, thoughts.

SUMMARY OF THE INVENTION

The present invention is directed to a method for the treatment of depression (preferably treatment resistant depression), for the treatment of depression in a suicidal patient, and/or for the treatment and/or prevention of suicidality (e.g. suicidal ideations) comprising
- Step A: genetically testing (or genotyping) a patient suffering from depression to determine their Val66Met rs6265 polymorphism in the BDNF gene (i.e. to determine if the patient is a Val/Val homozygote, a Val/Met heterozygote or a Met/Met homozygote); and
- Step B: administering an esketamine dosing regimen; wherein the esketamine is preferably administered intranasally; and wherein the dosing regimen comprises
  - (i) an induction dosing phase;
    - wherein the induction phase comprises a treatment period of between 2 and 8 weeks (preferably between 2 and 6 weeks, preferably between 2 and 4 weeks, for example, for 2 weeks, for 3 weeks, for 4 weeks, for 6 weeks or for 8 weeks);
    - wherein the esketamine is administered at a dosing frequency of one to five times per week (preferably, one to three times per week, preferably once or twice per week, preferably twice per week);
    - wherein, if the patient is a Val/Val homozygote, then the esketamine is administered at a dosage in an amount in the range of from about 28 mg to about 56 mg;
    - wherein, if the patient is a Val/Met heterozygote or a Met/Met homozygote, then the esketamine is administered at a dosage in an amount in the range of from about 56 mg to about 84 mg;
    - and wherein, during the induction phase, the dosage amount and/or the dosing frequency for the patient who is a Val/Val homozygote and the dosage amount and/or dosing frequency for the patient who is a Val/Met heterozygote or Met/Met homozygote (i.e. the patient is a Met carrier) are different; (preferably, the dosage amount is different);
  - and (b) a maintenance phase;
    - wherein the maintenance phase comprises a treatment period of at least 6 weeks (preferably at least 8 weeks, preferably at least 10 weeks, more preferably at least 12 weeks, more preferably at least 14 weeks);
    - wherein, if the patient is a Val/Val homozygote, then the esketamine is administered at a dosage in an amount in the range of from about 28 mg to about 56 mg; and
    - wherein the esketamine is administered at a dosing frequency in the range of once every two weeks to once every four weeks;
    - wherein, if the patient is a Val/Met heterozygote or a Met/Met homozygote, then the esketamine is administered at a dosage in an amount in the range of from about 56 mg to about 84 mg; and wherein the esketamine is administered at a dosing frequency in the range of once per week to once every two weeks;
    - and wherein, during the maintenance phase, the dosage amount and/or the dosing frequency for the patient who is a Val/Val homozygote and the dosage amount and/or dosing frequency for the patient who is a Val/Met heterozygote or Met/Met homozygote (i.e. the patient is a Met carrier) are different; (preferably, the dosage amount is different);
    - and wherein the maintenance phase preferably continues until further treatment is not required (as determined by a clinician or physician).

The present invention is further directed to a method for the treatment of depression (preferably treatment resistant depression), for the treatment of depression in a suicidal patient, and/or for the treatment and/or prevention of suicidality (e.g. suicidal ideations) comprising
- Step A: genetically testing (or genotyping) a patient suffering from depression to determine their Val66Met rs6265 polymorphism in the BDNF gene (i.e. to determine if the patient is a Val/Val homozygote, a Val/Met heterozygote or a Met/Met homozygote); and
- Step B: administering esketamine, preferably intranasally, according to an induction phase regimen;
  - wherein the induction phase comprises a treatment period of between 2 and 8 weeks (preferably between 2 and 6 weeks, preferably between 2 and 4 weeks, for example, for 2 weeks, for 3 weeks, for 4 weeks, for 6 weeks or for 8 weeks);
  - wherein the esketamine is administered at a dosing frequency of one to five times per week (preferably, one to three times per week, preferably once or twice per week, preferably twice per week);
  - wherein, if the patient is a Val/Val homozygote, then the esketamine is administered at a dosage in an amount in the range of from about 28 mg to about 56 mg;
  - wherein, if the patient is a Val/Met heterozygote or a Met/Met homozygote, then the esketamine is administered at a dosage in an amount in the range of from about 56 mg to about 84 mg;
  - and wherein, during the induction phase, the dosage amount and/or the dosing frequency for the patient who is a Val/Val homozygote and the dosage amount and/or dosing frequency for the patient who is a Val/Met heterozygote or Met/Met homozygote (i.e. the patient is a Met carrier) are different; (preferably, the dosage amount is different).

The present invention is further directed to a method for the treatment of depression (preferably treatment resistant depression), for the treatment of depression in a suicidal patient, and/or for the treatment and/or prevention of suicidality (e.g. suicidal ideations) comprising
- Step A: genetically testing (or genotyping) a patient suffering from depression to determine their Val66Met rs6265 polymorphism in the BDNF gene (i.e. to determine if the patient is a Val/Val homozygote, a Val/Met heterozygote or a Met/Met homozygote); and
- Step B: administering esketamine, preferably intranasally, according to a maintenance phase regimen;

wherein the maintenance phase comprises a treatment period of at least 6 weeks (preferably at least 8 weeks, preferably at least 10 weeks, more preferably at least 12 weeks, more preferably at least 14 weeks);

wherein, if the patient is a Val/Val homozygote, then the esketamine is administered at a dosage in an amount in the range of from about 28 mg to about 56 mg; and wherein the esketamine is administered at a dosing frequency in the range of once every two weeks to once every four weeks;

wherein, if the patient is a Val/Met heterozygote or a Met/Met homozygote, then the esketamine is administered at a dosage in an amount in the range of from about 56 mg to about 84 mg; and wherein the esketamine is administered at a dosing frequency in the range of once per week to once every two weeks;

wherein, during the maintenance phase, the dosage amount and/or the dosing frequency for the patient who is a Val/Val homozygote and the dosage amount and/or dosing frequency for the patient who is a Val/Met heterozygote or Met/Met homozygote (i.e. the patient is a Met carrier) are different; (preferably, the dosage amount is different);

and wherein the maintenance phase preferably continues until further treatment is not required (as determined by a clinician or physician).

The present invention is further directed to a dosing regimen for the treatment of depression (preferably, treatment resistant depression), for the treatment of depression in a suicidal patient, and/or for the treatment and/or prevention of suicidality (e.g. suicidal ideations) comprising:

A) administering an esketamine dosing regimen; wherein the esketamine is preferably administered intranasally; and wherein the dosing regimen comprises
  (i) an induction dosing phase;
    wherein the induction phase comprises a treatment period of between 2 and 8 weeks (preferably between 2 and 6 weeks, preferably between 2 and 4 weeks, for example, for 2 weeks, for 3 weeks, for 4 weeks, for 6 weeks or for 8 weeks);
    wherein the esketamine is administered at a dosage in an amount in the range of from about 28 mg to about 56 mg;
    and wherein the esketamine is administered at a dosing frequency of one to five times per week (preferably, one to three times per week, preferably once or twice per week, preferably twice per week);
  and (b) a maintenance phase;
    wherein the maintenance phase comprises a treatment period of at least 6 weeks (preferably at least 8 weeks, preferably at least 10 weeks, more preferably at least 12 weeks, more preferably at least 14 weeks);
    wherein the esketamine is administered at a dosage in an amount in the range of from about 28 mg to about 56 mg;
    wherein the esketamine is administered at a dosing frequency in the range of once every two weeks to once every four weeks;
    and wherein the maintenance phase preferably continues until further treatment is not required (as determined by a clinician or physician).

The present invention is further directed to a dosing regimen for the treatment of depression (preferably, treatment resistant depression), for the treatment of depression in a suicidal patient, and/or for the treatment and/or prevention of suicidality (e.g. suicidal ideations) comprising:

A) administering esketamine, preferably intranasally, according to an induction phase regimen;
  wherein the induction phase comprises a treatment period of between 2 and 8 weeks (preferably between 2 and 6 weeks, preferably between 2 and 4 weeks, for example, for 2 weeks, for 3 weeks, for 4 weeks, for 6 weeks or for 8 weeks);
  wherein the esketamine is administered at a dosage in an amount in the range of from about 28 mg to about 56 mg;
  and wherein the esketamine is administered at a dosing frequency of one to five times per week (preferably, one to three times per week, preferably once or twice per week, preferably twice per week).

The present invention is further directed to a dosing regimen for the treatment of depression (preferably, treatment resistant depression), for the treatment of depression in a suicidal patient, and/or for the treatment and/or prevention of suicidality (e.g. suicidal ideations) comprising:

A) administering esketamine, preferably intranasally, according to a maintenance phase regimen;
  wherein the maintenance phase comprises a treatment period of at least 6 weeks (preferably at least 8 weeks, preferably at least 10 weeks, more preferably at least 12 weeks, more preferably at least 14 weeks);
  wherein the esketamine is administered at a dosage in an amount in the range of from about 28 mg to about 56 mg;
  wherein the esketamine is administered at a dosing frequency in the range of once every two weeks to once every four weeks;
  and wherein the maintenance phase preferably continues until further treatment is not required (as determined by a clinician or physician).

The present invention is further directed to a dosing regimen for the treatment of depression (preferably, treatment resistant depression), for the treatment of depression in a suicidal patient, and/or for the treatment and/or prevention of suicidality (e.g. suicidal ideations) comprising:

A) administering an esketamine dosing regimen; wherein the esketamine is preferably administered intranasally; and wherein the dosing regimen comprises
  (i) an induction dosing phase;
    wherein the induction phase comprises a treatment period of between 2 and 8 weeks (preferably between 2 and 6 weeks, preferably between 2 and 4 weeks, for example, for 2 weeks, for 3 weeks, for 4 weeks, for 6 weeks or for 8 weeks);
    wherein the esketamine is administered at a dosage in an amount in the range of from about 56 mg to about 84 mg;
    wherein the esketamine is administered at a dosing frequency of one to five times per week (preferably, one to three times per week, preferably once or twice per week, preferably twice per week);
  and (b) a maintenance phase;
    wherein the maintenance phase comprises a treatment period of at least 6 weeks (preferably at least 8 weeks, preferably at least 10 weeks, more preferably at least 12 weeks, more preferably at least 14 weeks);
    wherein the esketamine is administered at a dosage in an amount in the range of from about 56 mg to about 84 mg;
    wherein the esketamine is administered at a dosing frequency in the range of once per week to once every two weeks;

and wherein the maintenance phase preferably continues until further treatment is not required (as determined by a clinician or physician).

The present invention is further directed to a dosing regimen for the treatment of depression (preferably, treatment resistant depression), for the treatment of depression in a suicidal patient, and/or for the treatment and/or prevention of suicidality (e.g. suicidal ideations) comprising:

A) administering esketamine, preferably intranasally, according to an induction phase regimen;
 wherein the induction phase comprises a treatment period of between 2 and 8 weeks (preferably between 2 and 6 weeks, preferably between 2 and 4 weeks, for example, for 2 weeks, for 3 weeks, for 4 weeks, for 6 weeks or for 8 weeks);
 wherein the esketamine is administered at a dosage in an amount in the range of from about 56 mg to about 84 mg;
 and wherein the esketamine is administered at a dosing frequency of one to five times per week (preferably, one to three times per week, preferably once or twice per week, preferably twice per week).

The present invention is further directed to a dosing regimen for the treatment of depression (preferably, treatment resistant depression), for the treatment of depression in a suicidal patient, and/or for the treatment and/or prevention of suicidality (e.g. suicidal ideations) comprising:

A) administering esketamine, preferably intranasally, according to a maintenance phase regimen;
 wherein the maintenance phase comprises a treatment period of at least 6 weeks (preferably at least 8 weeks, preferably at least 10 weeks, more preferably at least 12 weeks, more preferably at least 14 weeks);
 wherein the esketamine is administered at a dosage in an amount in the range of from about 56 mg to about 84 mg;
 wherein the esketamine is administered at a dosing frequency in the range of once per week to once every two weeks;
 and wherein the maintenance phase preferably continues until further treatment is not required (as determined by a clinician or physician).

In an embodiment of the present invention, the esketamine is administered at a dosage in the range of from about 28 mg to about 84 mg (for example at about 28 mg, at about 56 mg or at about 84 mg); and at the lowest frequency at which the antidepressant response is maintained.

In another embodiment of the present invention, in maintenance dosing or during the maintenance phase of the dosing regimen, the esketamine is administered at a dosage in the range of from about 28 mg to about 84 mg (for example at about 28 mg, at about 56 mg or at about 84 mg); and at the lowest frequency at which the antidepressant response is maintained.

BRIEF DESCRIPTION OF THE FIGURES

FIG. 1 illustrates the mean changes in MADRS total score from baseline after the 1$^{st}$ infusion by Val/Val or Met carriers and by placebo or active.

FIG. 2 illustrates the survival curves for the duration of response in esketamine responders per day 1 randomization after Day 17 by Val/Val or Met carriers.

FIG. 3 illustrates survival curves for duration of response by Val/Val or Met carriers in all responders to esketamine after Day 17.

FIG. 4 illustrates mean changes in MADRS total scores from baseline over time up to Day 15 by Val/Val or Met carriers and by ketamine or placebo.

FIG. 5 illustrates survival curves for the duration of response Day 29 and up to Day 44 by Val/Val or Met carriers in ketamine responders.

DETAILED DESCRIPTION OF THE INVENTION

The present invention is directed to methods and dosing regimens for the treatment of depression (preferably treatment resistant depression), for the treatment of depression in a suicidal patient, and/or for the treatment and/or prevention of suicidality (e.g. suicidal ideations) comprising genotyping a patient in need thereof and administering ketamine, preferably esketamine, preferably intranasal esketamine, according to a dosing regimen which is selected (preferably optimized) for said patient, based on the subject's Val66Met rs6265 BDNF genotype, and as described in more detail herein.

One skilled in the art will recognize that the maintenance phase of the dosing regimens of the present invention will continue until further treatment is not required, for example as determined by a clinician, physician, psychiatrist, psychologist, or other suitable medical professional, and as indicated by for example, prolonged remission of the depression (including for example, the remission of one or more symptoms associated with the depression), social and/or occupational functional improvement(s) to normal or premorbid levels, or other known measures of depression.

One skilled in the art will further recognize that in the methods and dosing regimens of the present invention, the maintenance of the antidepressant response in a patient may be determine by for example, a clinician, physician, psychiatrist, psychologist, or other suitable medical professional. Additionally, maintenance of the antidepressant response may be established by for example, an absence of relapse of the depression (or one or more symptoms of the depression), an absence of the need for additional or alternate treatment(s) for the depression, an absence of the worsening of the depression, an absence of the need for hospitalization for a suicidal attempt or to prevent suicide, or, when evaluated by MADRS score, by maintenance of a MADRS score less than about 22 and/or the absence of a MADRS score above 22 for any continuous two week period.

As used herein, the term "depression" shall be defined to include major depressive disorder, unipolar depression, treatment resistant depression, depression with anxious distress, bipolar depression and dysthymia (also referred to as dysthymic disorder). Preferably, the depression is major depressive disorder, unipolar depression, treatment resistant depression, depression with anxious distress, or bipolar depression. More preferably, the depression is major depressive disorder, unipolar depression, treatment resistant depression and bipolar depression. More preferably, the depression is treatment-resistant depression.

In an embodiment, the present invention is directed to methods and dosing regimens for the treatment of depression in suicidal patients. One skilled in the art will recognize that the term "depression in suicidal patients" shall include any type of depression as herein defined, when diagnosed in a patient that also exhibits at least one symptom of suicidality, for example suicidal ideations and/or behaviors (e.g. intent, planning, etc.). Thus, "depression in suicidal patients" includes, but is not limited to, major depressive disorder in suicidal patients, unipolar depression in suicidal patients, treatment resistant depression in suicidal patients, depression with anxious distress in suicidal patients, bipolar depression in suicidal patients and dysthymia in suicidal patients. Preferably, the "depression in suicidal patients" is selected from the group consisting of major depressive disorder in suicidal patients, unipolar depression in suicidal patients and treatment resistant depression in suicidal patients. More preferably, the "depression in suicidal patients" is treatment resistant depression in suicidal patients.

As used herein, the term "treatment-refractory or treatment-resistant depression" and the abbreviation "TRD" shall be defined as a major depressive disorder that does not respond to a least two antidepressant regimens or treatments.

As used herein, unless otherwise noted, the term "antidepressant" shall mean any pharmaceutical agent which can be used to treat depression. Suitable examples include, but are not limited to mono-amine oxidase inhibitors such as phenelzine, tranylcypromine, moclobemide, and the like; tricyclics such as imipramine, amitriptyline, desipramine, nortriptyline, doxepin, protriptyline, trimipramine, chlomipramine, amoxapine, and the like; tetracyclics such as maprotiline, and the like; non-cyclics such as nomifensine, and the like; triazolopyridines such as trazodone, and the like; serotonin reuptake inhibitors such as fluoxetine, sertraline, paroxetine, citalopram, escitalopram, fluvoxamine, and the like; serotonin receptor antagonists such as nefazadone, and the like; serotonin noradrenergic reuptake inhibitors such as venlafaxine, milnacipran, desvenlafaxine, duloxetine and the like; noradrenergic and specific serotonergic agents such as mirtazapine, and the like; noradrenaline reuptake inhibitors such as reboxetine, edivoxetine and the like; atypical antidepressants such as bupropion, and the like; natural products such as Kava-Kava, St. John's Wort, and the like; dietary supplements such as s-adenosylmethionine., and the like; and neuropeptides such as thyrotropin-releasing hormone and the like; compounds targeting neuropeptide receptors such as neurokinin receptor antagonists and the like; and hormones such as triiodothyronine, and the like. Preferably, the antidepressant is selected from the group consisting of fluoxetine, imipramine, bupropion, venlafaxine and sertaline.

Therapeutically effective dosage levels and dosage regimens for antidepressants (for example, mono-amine oxidase inhibitors, tricyclics, serotonin reuptake inhibitors, serotonin noradrenergic reuptake inhibitors, noradrenergic and specific serotonergic agents, noradrenaline reuptake inhibitor, natural products, dietary supplements, neuropeptides, compounds targeting neuropeptide receptors, hormones and other pharmaceutical agents disclosed herein), may be readily determined by one of ordinary skill in the art. For example, therapeutic dosage amounts and regimens for pharmaceutical agents approved for sale are publicly available, for example as listed on packaging labels, in standard dosage guidelines, in standard dosage references such as the Physician's Desk Reference (Medical Economics Company or online at http://www.pdrel.com) or other sources.

As used herein the term "antipsychotic" includes, but is not limited to:

(a) typical or $1^{st}$ generation antipsychotics, such as phenothiazines (e.g., chlorpromazine, thioridazine, fluphenazine, perphenazine, trifluoperazine, levomepromazin), thioxanthenes (e.g., thiothixene, flupentixol), butyrophenones (e.g., haloperidol), dibenzoxazepines (e.g., loxapine), dihydroindolones (e.g., molindone), substituted benzamides (e.g., sulpride, amisulpride), and the like; and (b) atypical or $2^{nd}$ generation antipsychotics, such as paliperidone, clozapine, risperidone, olanzapine, quetiapine, zotepine, ziprasidone, iloperidone, perospirone, blonanserin, sertindole, ORG-5222 (Organon), and the like; and others such as sonepiprazole, aripiprazole, brexpiprazole, nemonapride, SR-31742 (Sanofi), CX-516 (Cortex), SC-111 (Scotia), NE-100 (Taisho), and the like.

In an embodiment, the "atypical antipsychotic" is selected from the group consisting of aripiprazole, brexpiprazole, quetiapine, olanzapine, risperidone and paliperidone. In another embodiment, the atypical antipsychotic is selected from the group consisting of aripiprazole, quetiapine, olanzapine and risperidone; preferably, the atypical antipsychotic is selected from the group consisting of aripiprazole, quetiapine and olanzapine.

One skilled in the art will recognize that wherein the present invention is directed to methods or dosing regimens for the treatment and/or prevention of suicidality, said methods and dosing regimens include, but are not limited to, the prevention of suicidal ideations, suicidal behaviors, suicidal attempts and/or suicide.

As used herein, unless otherwise noted, the term "esketamine" shall mean the (S)-enantiomer of ketamine, as its corresponding hydrochloride salt, a compound of formula (I)

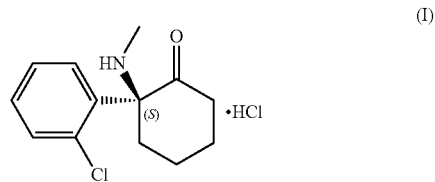

also known as (S)-2-(2-chlorophenyl)-2-(methylamino)cyclohexanone hydrochloride.

As used herein, unless otherwise noted, the term "Met carrier" shall mean a patient or subject who is either a Val/Met heterozygote or a Met/Met homozygote, as determined by testing said patient or subject for Val66Met rs6265 polymorphism in BDNF.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

As used herein, unless otherwise noted, the terms "subject" and "patient" refer to an animal, preferably a mammal, most preferably a human, who has been the object of treatment, observation or experiment. Preferably, the subject or patient has experienced and/or exhibited at least one symptom of the disease or disorder to be treated and/or prevented. One skilled in the art will further recognize that the methods of treatment or prevention and the dosing regimens of the present invention are directed to subjects or patients in need of such treatment, prevention or dosing regimen, more particularly to subjects or patients diagnosed with or exhibiting at least one symptom of depression (preferably, meeting the criteria for major depressive disorder or episode) regardless of type or underlying cause.

In an embodiment of the present invention, the subject or patient in need thereof is a subject or patient that has been diagnosed with or exhibits at least one symptom of depression (preferably, meeting the criteria for major depressive disorder or episode) and who has further been diagnosed with or exhibits at least one symptom of suicidality (e.g. suicidal ideations and/or behaviors).

The term "therapeutically effective amount" as used herein, (for example, in describing monotherapy with intranasal esketamine) means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Wherein the present invention is directed to therapy with a combination of agents, "therapeutically effective amount" shall mean that amount of the combination of agents taken together so that the combined effect elicits the desired biological or medicinal response. For example, the therapeutically effective amount of combination therapy comprising esketamine and a serotonin reuptake inhibitor would be the amount of esketamine and the amount of the serotonin reuptake inhibitor that when taken together or sequentially have a combined effect that is therapeutically effective, more preferably where the combined effect is synergistic. Further, it will be recognized by one skilled in the art that in the case of combination therapy with a therapeutically effect amount, the amount of each component of the combination individually may or may not be therapeutically effective.

Wherein the present invention is directed to the administration of a combination, the compounds may be co-administered simultaneously, sequentially, separately or in a single pharmaceutical composition. Where the compounds are administered separately, the number of dosages of each compound given per day, may not necessarily be the same, e.g. where one compound may have a greater duration of activity, and will therefore, be administered less frequently. Further, the compounds may be administered via the same or different routes of administration, and at the same or different times during the course of the therapy, concurrently in divided or single combination forms. The instant invention is therefore understood as embracing all regimens of simultaneous or alternating treatment and the term "administering" is to be interpreted accordingly.

As used herein, the terms "co-therapy", "combination therapy", "adjunctive treatment", "adjunctive therapy" and "combined treatment" shall mean treatment of a patient in need thereof by administering esketamine in combination with one or more antidepressant(s), and further, optionally in combination with one or more atypical antipsychotics wherein the esketamine and the antidepressant(s) are administered by any suitable means, simultaneously, sequentially, separately or in a single pharmaceutical formulation. Where the esketamine and the antidepressant(s) are administered in separate dosage forms, the number of dosages administered per day for each compound may be the same or different. The esketamine and the antidepressant(s) may be administered via the same or different routes of administration. Examples of suitable methods of administration include, but are not limited to, oral, intravenous (iv), intranasal (in) intramuscular (im), subcutaneous (sc), sublingual, transdermal, and rectal. Compounds may also be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices. The esketamine and the antidepressant(s) may be administered according to simultaneous or alternating regimens, at the same or different times during the course of the therapy, concurrently in divided or single forms.

Optimal dosages to be administered may be readily determined by those skilled in the art, and will vary with the particular compound or compounds used, the mode of administration, the strength of the preparation and the advancement of the disease condition. In addition, factors associated with the particular patient being treated, including patient's sex, age, weight, diet, time of administration and concomitant diseases, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

As used herein, the term "composition" is intended to encompass a product comprising the specified ingredients in the specified amounts, as well as any product which results, directly or indirectly, from combinations of the specified ingredients in the specified amounts.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric add, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Val66Met rs6265

The Val66Met SNP rs6265 may be defined by SEQ ID. No. 2 (wherein R represents the position of the polymorphism):

```
CTGCAGAAAG GCCTGGAATT ACAATCAGAT GGGCCACATG

GCATCCCGGT GAAAGAAAGC CC

TAACCAGTTT TCTGTCTTGT TTCTGCTTTC TCCCTACAGT

TCCACCAGGT GAGAAGAGTG ATGACCATCC TTTTCCTTAC

TATGGTTATT TCATACTTTG GTTGCATGAA GGCTGCCCCC

ATGAAAGAAG CAAACATCCG AGGACAAGGT GGCTTGGCCT

ACCCAGGTGT GCGGACCCAT GGGACTCTGG AGAGCGTGAA

TGGGCCCAAG GCAGGTTCAA GAGGCTTGAC ATCATTGGCT

GACACTTTCG AACAC

R

TGATAGAAGA GCTGTTGGAT GAGGACCAGA AAGTTCGGCC

CAATGAAGAA AACAATAAGG ACGCAGACTT GTACACGTCC

AGGGTGATGC TCAGTAGTCA AGTGCCTTTG GAGCCTCCTC

TTCTCTTTCT GCTGGAGGAA TACAAAAATT ACCTAGATGC

TGCAAACATG TCCATGAGGG TCCGGCGCCA CTCTGACCCT

GCCCGCCGAG GGGAGCTGAG CGTGTGTGAC AGTATTAGTG

AGTGGGTAAC GGCGG

CAGACAAAAA GACTGCAGTG GACATGTCGG GCGGGACGGT

CACAGTCCTT GAAAAGGTCC CTGTATCAAA AGGCCAACTG

AAGCAATACT TCTACGAGAC CAAGTGCAAT CCCATGGGTT

ACACAAAAGA AGGCTGCAGG GGCATAGACA AAAGGCATTG

GAACTCCCAG TGCCGAACTA CCCAGTCGTA CGTGCGGGCC

CTTACCATGG ATAGCAAAAA GAGAATTGGC TGGCGATTCA

TAAGGATAGA CACTTCTTGT GTATGTACAT TGACCATTAA

AAGGGGAAGA TAGTGGATTT ATGTTGTATA GATTAGATTA

TATTGAGACA AAAATTATCT ATTTGTATAT ATACATAACA

GGGTAAATTA TTCAGTTAAG AAAAAAATAA TTTTATGAAC

TGCATGTATA AATGAAGTTT ATACAGTACA GTGGTTCTAC

AATCTATTTA TTGGACATGT CCATGACCAG AAGGGAAACA

GTCATTTGCG CACAACTTAA AAAGTCTGCA TTACATTCCT

TGATAATGTT GTGGTTTGTT GCCGTTGCCA AGAACTGAAA

ACATAAAAAG TTAAAAAAAA TAATAAATTG CATGCTGCTT

TAATTGTGAA TTGATAATAA ACTGTCCTCT TTCAGAAAAC

AGAAAAAAAC ACACACACAC ACAACAAAAA TTTGAACCAA

AACATTCCGT TTACATTTTA GACAGTAAGT ATCTTCGTTC

TTGTTAGTAC TATATCTGTT TTACTGCTTT TAACTTCTGA
```

-continued

```
TAGCGTTGGA ATTAAAACAA TGTCAAGGTG CTGTTGTCAT

TGCACCCCCA AGGGGAACTA ACCGCCTCCC ACACACTATA

TTCCTGCCAC CCCCGCCCCA CCCTACACCG GCCCCGCACC GCCCC
>gnl|dbSNP|rs6265|allelePos = 318|totalLen = 1458|
taxid = 9606|snpclass = 1|alleles = 'A/G'|mol =
Genomic|build = 138
```

Val66Met rs6265 Genotype Testing

Genotype testing for Val66Met rs6265 polymorphism in BDNF may be completed according to known methods, for example, as described in PECIÑA M., et al., "Valence-specific effects of BDNF Val66Met polymorphism on dopaminergic stress and reward processing in humans", *J Neurosci.*, 2014 Apr. 23, pp 5874-81, Vol 34(17); and LIM, Y. Y, et al., (Australian Imaging, Biomarkers and Lifestyle (AIBL) Research Group), "BDNF Val66Met, Aβ amyloid, and cognitive decline in preclinical Alzheimer's disease", *Neurobiol Aging*, 2013 November, pp 2457-2464, Vol. 34(11).

Additionally, genotype testing for Val66Met rs6265 polymorphism in BDNF may be accomplished using the TagMan® SNP Genotyping Assay Kit (Catalog #4351379; rs6265, BDNF-AS, Location Chr. 11:27679916, Transition Substitution, Mis-sense, Mutation, Intragenic) available from Life Technologies™ (a brand of Thermo Fisher Scientific) (see for example http://www.lifetechnologies.com/order/genome-database/browse/genotyping/keyword/RS6265) or other commercial and experimental testing kits which can be used to perform Val66Met rs6265 genetic testing.

Val66Met rs6265 Polymorphism in BDNF and Patient Response to Ketamine and Esketamine Treatment The effect of Val66Met rs6265 Polymorphism in BDNF Gene on Clinical response to esketamine and ketamine was investigated through a retrospective analysis of the following clinical trials, respectively: ESKETIVTRD2001 and KETIVTRD2002. Complete trial design, efficacy endpoints and pharmacogenetic testing details are available at the U.S. National Institututes of Health Clinical Trials Registry (www.clinicaltrials.gov), and are summarized in Example 1, which follows herein.

The analysis found that the Met allele of the Val66Met rs6265 polymorphism in the BDNF gene was associated with a smaller clinical response to acute, single dose ketamine or esketamine administration. In both studies, decrease in depression severity evaluated with the MADRS scale and response rates (i.e. percentage of subjects who show a response or remission based on standard clinical criteria) to the first 1-2 doses of ketamine, or esketamine were smaller in the Met carrier genotypes. The presence of at least one Met allele in the Met carrier subjects is theorized to signify a lower capacity for BDNF release, which may result into reduced synaptic plasticity; this eventually manifests clinically as lower capacity for mood improvement. Further, in the KETIVTRD2002 study, in Met carriers, the drug improvement "catches up" to the response achieved in Val homozygotes patients after repeated dosing. In the ESKETIVTRD2001 study the clinical improvement in Val homozygotes is greater than the one seen in the Met carriers after the first 1-2 administrations (day 7). In the KETIVTRD2002 study the clinical improvement seen in the Met carriers no longer differs from that of the Val homozygotes after Day 7, and at the study endpoint (Day 29), which is after repeated doses of ketamine, the depression score changes, response and remission rates are similar between the two genotype-based subgroups. Finally, there was also an effect of genotype on the durability of the clinical response following last drug dose. In ESKETIVTRD2001 the proportion of esketamine subjects who remained well in the Met carrier group was cut in half (from 6 to 3) at Day 21. In contrast all 7 of the Val/Val subjects remain well by Day 35. In KETIVTRD2002 the proportion of subjects who remain well in the Met carrier group was cut also in half (also from 7 to 4) at Day 39; while in contrast most of the Val/Val subjects (12 of 14) remain well by Day 44.

The following Examples are set forth to aid in the understanding of the invention, and are not intended and should not be construed to limit in any way the invention set forth in the claims which follow thereafter.

Example 1

Effect of Val66Met rs6265 Polymorphism in BDNF; Retrospective Analysis of Esketamine (ESKETIVTRD2001) and Ketamine (KETIVTRD2002) Clinical Trials ESKETIVTRD2001 Clinical Trial Design and Objectives:

This was a double-blind, double-randomization, placebo-controlled, multiple dose titration study in 30 adult subjects with TRD. The study consisted of 3 phases: a screening phase of up to 2 weeks, a 7-day double-blind (DB) treatment phase (Day 1 to Day 7), and a 4-week post-treatment (with optional open label [OL] esketamine 0.40 mg/kg during follow-up [FU]: administered on Days 7, 10, 14 and 17.). The interval between the first and last dose of study medication was 3 days. Approximately 30 adult subjects with TRD were randomized to treatment (esketamine 0.40 mg/kg, esketamine 0.20 mg/kg, or placebo i.v. infusion) in a 1:1:1 ratio on Day 1.

If esketamine 0.40 mg/kg dose was not well tolerated on Day 1 and/or Day 4 the dose may be reduced to 0.3 mg/kg. Subjects who were responders after the dose on Day 1 received the same treatment again on Day 4. A responder was a subject who had a reduction in MADRS total score of >50% versus baseline on Day 2, 3, or 4 (prior to dosing).

For subjects who were not responders after the dose on Day 1, the following rule was applied for treatment on Day 4:

Placebo on Day 1: re-randomization to esketamine 0.40 mg/kg or esketamine 0.20 mg/kg i.v. infusion on Day 4;

Esketamine 0.20 mg/kg on Day 1: treatment with esketamine 0.40 mg/kg i.v. infusion on Day 4;

Esketamine 0.40 mg/kg on Day 1: treatment with esketamine 0.40 mg/kg i.v. infusion again on Day 4.

One week (7 days) after the end of the double-blind treatment phase (Day 14), subjects returned to the unit for a follow-up visit. Telephone visits were conducted 3 (i.e., Day 10), 10 (i.e., Day 17), 14 (i.e., Day 21), 21 (i.e., Day 28), and 28 (i.e., Day 35) days after the end of the double-blind treatment phase. For subjects who chose it, and when agreed with the investigator, optional open label treatment of esketamine 0.40 mg/kg (or lower when required) on Days 7, 10, 14 and 17 was made available by the sponsor. The total study duration for each subject was a maximum of 7 weeks. The end of study was defined as the date of the last study assessment of the last subject in the trial.

The primary objectives of this trial were to investigate the safety and tolerability of esketamine i.v. infusion in patients with TRD; and to assess the efficacy of esketamine at 24 hours after dosing on Day 1, administered as a 0.40 mg/kg and 0.20 mg/kg intravenous (i.v.) infusion, compared with placebo in improving symptoms of depression in patients with TRD, using the Montgomery-Asberg Depression Rating Scale (MADRS).

Clinical Endpoints:
  Changes from baseline in MADRS total score after the 1$^{st}$ infusion (up to Day 4 pre-dose)
  % responders (reduction in MADRS total score of >50% from baseline) on Days 2, 7, 17 and 35
  Duration of esketamine response after the end of the OL phase (from Day 17 up to Day 35))
  % remitters (MADRS total score 10) on Days 2, 7, 17 and 35
  Note: For the ESKETIVTRD2001 clinical trial, after the end of the OL phase (from Day 17 to Day 35), all responders were considered "well" (i.e. responding to the esketamine treatment). Said responders were not followed post-trial for a sufficient period of time to observe a meaningful number of relapses and therefore to determine time to relapse (empirically defined as a MADRS total score 22). As such, this parameter was not included in the analysis.
  Additionally, although MADRS Suicidal Thoughts measurements were taken during the course of the ESKETIVTRD2001 clinical trial, subjects/patients exhibiting suicidal ideation (e.g. suicidal thoughts) at enrollment, were specifically excluded. Analysis of the effect of Val66Met polymorphism on suicidality as measured by the MADRS Suicidal Thoughts Scale was therefore deemed not applicable and not generalizable to subjects with suicidal ideation (e.g. clinically relevant).

KETIVTRD2002 Clinical Trial Design and Objectives:
  This was a double-blind, randomized, placebo-controlled, parallel arm study to assess the safety and efficacy of ketamine dosed 2 or 3 times weekly in adult subjects with treatment resistant depression. The study consisted of up to 4 phases: a screening phase of up to 4 weeks, a 4-week double-blind treatment phase (Day 1 to Day 29), an optional 2-week open label treatment phase, and a post treatment (follow up) phase of up to 3 weeks.
  On Day 1 of the double-blind treatment phase, subjects were randomized to receive either i.v. infusions of placebo 2 times weekly or i.v. infusions of placebo 3 times weekly or i.v. infusions of ketamine 0.50 mg/kg, 2 times weekly or i.v. infusions of ketamine 0.50 mg/kg, 3 times weekly over 4 weeks.
  Subjects who discontinued the double-blind treatment phase of the study due to lack of efficacy (based upon the clinical judgment of the investigator) after completion of the Day 15 visit, but prior to the Day 29 visit, may have received open-label ketamine treatment with the same dose frequency for an additional 2 weeks. After completing the Early Termination visit, the subject had study assessments as per the Time and Events Schedule for the optional open-label treatment phase followed by one follow up visit performed 1 week after the last dose of study medication. The total study duration for each subject was approximately 13 weeks.
  The primary objectives for the trial were to assess the safety and tolerability of multiple doses over 4 weeks of ketamine administered as a 0.50 mg/kg intravenous (i.v.) infusion in subjects with TRD; and to evaluate the efficacy of ketamine administered as a 0.50 mg/kg intravenous (i.v.) infusion, 2 or 3 times weekly for 4 weeks, for the treatment of TRD compared to placebo using the Montgomery-Asberg Depression Rating Scale (MADRS) between Day 1 (pre-dose) and the (pre-dose) assessments through Day 15.

Clinical Endpoints:
  Changes in MADRS total score from baseline during the DB phase (up to Day 29)
  % responders (reduction in MADRS total score of ≥50% from baseline) during the DB phase (Days 3 or 4, 8, 15, 18, 29 and End Point[DB])
  Duration of ketamine response after the DB phase (from Day 29 up to Day 47
  % remitters (MADRS total score 10) on Days 3 or 4, 8, 15, and 29
  Note: For the KETIVTRD2002 clinical trial, after the end of the double-blind phase (from Day 29 to Day 47), all responders were considered "well" (i.e. responding to the ketamine treatment). Said responders were not followed post-trial for a sufficient period of time to observe a meaningful number of relapses and therefore to determine time to relapse (empirically defined as a MADRS total score 22). As such, this parameter was not included in the analysis.
  Additionally, although MADRS Suicidal Thoughts measurements were taken during the course of the KETIVTRD2002 clinical trial, subjects/patients exhibiting suicidal ideation (e.g. suicidal thoughts) at enrollment, were specifically excluded. Analysis of the effect of Val66Met polymorphism on suicidality as measured by the MADRS Suicidal Thoughts Scale was therefore deemed not applicable and not generalizable to subjects with suicidal ideation (e.g. clinically relevant).

Pooled Clinical Endpoints (Combining Results from ESKETIVTRD2001 and KETIVTRD2002)
  Changes in MADRS total score from baseline after the 1$^{st}$ infusion (Day 2 in ESKETIVTRD2001 and Day 3 or Day 4 in KETIVTRD2002)
  % responders after the 1$^{st}$ infusion (reduction in MADRS total scores>50% on Day 2 in ESKETIVTRD2001, and reduction in MADRS total scores≥50% on Day 3 or Day 4 in KETIVTRD2002)
  % responders after multiple doses (Day 7 in ESKETIVTRD2001 and Day 8 in KETIVTRD2002)
  % remitters after the 1$^{st}$ infusion (Day 2 in ESKETIVTRD2001 and Day 3 or Day 4 in KETIVTRD2002)

Pharmacogenetic (DNA) Evaluation of Patients in ESKETIVTRD2001 and KETIVTRD2002 Clinical Trials:
  For the ESKETIVTRD2001 study, subjects were given the option to participate in Part 1 only, Part 2 only, both parts, or neither part of the pharmacogenomic component of this study (where local regulations permit). For KETIVTRD2002 study, a 10 mL blood sample was collected from all enrolled subjects. Subject participation in Part 1 of the pharmacogenomic research was required for participation in the study. Subject participation in Part 2 was optional.
  Part 1 comprised collection of pharmacogenomic samples allowed for genetic research to help understand ketamine or major depressive disorder (MDD). DNA samples were only used for genetic research related to ketamine or MOD. Genetic research consisted of the analysis of one or more candidate genes or of the analysis of genetic markers throughout the genome (as appropriate) in relation to ketamine or MOD clinical endpoints. A list of candidate genes that were potentially relevant to ketamine or MDD was provided in the study protocol. Subjects were offered the separate option to consent to storage of their optional samples for future research as scientific discoveries are made.
  Part 2 of the pharmacogenomic research allowed for the storage of DNA samples for future genetic research related to ketamine or the indication(s) for which it is developed. Stored DNA samples and relevant clinical data were deidentified before research was to be done in the future. This involved removing personal identifiers and replacing the study subject identifier with a new number to limit the possibility of linking genetic data to a subject's identity.

The genetic endpoint was determination of a patient's Brain-Derived Neurotrophic Factor (BDNF) gene/polymorphism SNP (rs6265). Allele and genotype frequencies (counts) were calculated for all subjects from pooled ESKETIVTRD2001 and KETIVTRD2002 studies. Observed minor allele A (or T) frequency and genotyping frequency were compared to the reported frequency (in European population, frequency of minor allele A (or T) is ~20%; frequencies for A/A (or T/T), A/G (or T/C) and Val/Val G/G (or C/C) are ~3%, ~34%, and ~64%, respectively).

Efficacy Endpoint Analysis:

Summary statistics for changes in MADRS total score by Val/Val or Met carriers and by treatment regimen were determined for each study separately (up to Day 4 pre-dose in ESKETIVTRD2001, and up to Day 29 in KETIVTRD2002) and as well as for two studies pooled (after the 1$^{st}$ infusion: Day 2 in ESKETIVTRD2001 and Day 3 or Day 4 in KETIVTRD2002). Mean plots in changes in MADRS total score over time by Val/Val or Met carriers and by treatment regimen were determined for each study separately (up to Day 4 pre-dose in ESKETIVTRD2001 and up to Day 15 and Day 29 in KETIVTRD2002). Individual MADRS total score and as well as changes in MADRS total score were determined for each study separately (after the open label phase, Day 17 in ESKETIVTRD2001 and after the double blind phase Day 29 in KETIVTRD2002).

Proportions of responders or remitters at various time points by ValNal or Met carriers and by treatment regimen (per Day 1 randomization for EDKETIVTRD2001) were calculated for each study separately (Days 2, 7, 17 and 35 in EDKETIVTRD2001 and Days 3 or 4, 8, 15, and 29 in KETIVTRD2002). Likewise, proportions of responders or remitters by Val/Val or Met carriers in all subjects (pooled placebo and esketamine) in EDKETIVTRD2001 were calculated. In addition, response rates at Day 18 (FU) and End Point (DB) in KETIVTRD2002 were calculated.

The association between changes in MADRS total score from baseline (Day 2 inTESKETIVRD2001 and Day 3 or Day 4 in KETIVTRD2002) and the SNP (rs6265) were evaluated in placebo (pooled from ESKETIVTRD2001 and KETIVTRD2002) and active (pooled esketamine from ESKETIVTRD2001 and ketamine KETIVTRD2002) groups using an ANCOVA model under a dominant model with the baseline MARDS total score and genotype.

The association between the % responders or the % remitters (Day 2 in ESKETIVTRD2001, and Day 3 or Day 4 in KETIVTRD2002) and the SNP (rs6265) were evaluated in placebo (pooled from ESKETIVTRD2001 and KETIVTRD2002) and active (pooled esketamine from ESKETIVTRD2001 and ketamine KETIVTRD2002) groups using a logistic regression model under a dominant model with the baseline MADRS total score and genotype.

The duration of response (after the open label phase Day 17 in ESKETIVTRD2001, and after the double blind phase Day 29 in KETIVTRD2002) was evaluated using Kaplan-Meier method with the strata of carrier (Val/Val or Met carriers). The survival curves of the duration of response by Val/Val or Met carriers were plotted for each study separately.

Time to relapse in all responders (after the open label phase Day 17 in EDKETIVTRD2001 and after the double blind phase Day 29 in KETIVTRD2002) was evaluated using Kaplan-Meier method with the strata of carrier (Val/Val or Met carriers). The survival curves of time to relapse by Val/Val or Met carriers were plotted for each study separately.

Analysis Results

The analysis set contained 93 subjects, including 41 in placebo, 17 in ESKETIVTRD2001 and 35 in KETIVTRD2002. Hardy-Weinberg Equillibrium (HWE) analysis found that genotype frequency observed in the two clinical trials was in line with the reported frequency in European populations. Analysis was completed for patients in the ESKETIVTRD2001 and KETIVTRD2002 clinical trials individually, and pooled, with results as detailed below.

Results from Pooled ESKETIVTRD2001 and KETIVTRD2002 Clinical Trials Analysis

A) MADRS Scores: Mean changes in MADRS total score from baseline after the 1$^{st}$ infusion (Day 2 in TRD2001 and Day 3 or Day 4 in TRD2002) by Val/Val or Met carriers were as listed in Table P-1, below. Larger reductions were observed in Val/Val subjects as compared to Met carriers for both placebo and active (esketamine or ketamine).

TABLE P-1

MADRS Total Scores, Actual Values and Changes from Baseline After the First Infusion (Day 2 in TRD2001 and Day 3 or Day 4 TRD2002) by Val/Val or Met Carriers and by Active or Placebo

|  | No. | Mean (SD) | Change from Baseline No. | Mean (SD) |
|---|---|---|---|---|
|  | Val/Val | | | |
| Placebo | 29 | 30.48 (8.100) | 29 | −5.62 (7.218) |
| Active | 29 | 18.93 (8.980) | 29 | −15.14 (9.054) |
|  | Met Carriers | | | |
| Placebo | 11 | 33.27 (5.850) | 11 | −1.64 (5.697) |
| Active | 22 | 24.27 (8.072) | 22 | −8.86 (7.511) |

Placebo: pooled from placebos from esketamine and ketamine

Active: pooled from low, high dose from esketamine and 2X/WK, 3X/WK from ketamine B) % Responders: The % responders after the 1$^{st}$ infusion (Day 2 in TRD2001 and Day 3 or Day 4 in TRD2002) by Val/Val or Met carriers and by placebo or active, and by esketamine or ketamine were as listed in Table P-2 below. Response rates were higher in Val/Val subjects than in Met carriers.

TABLE P-2

MADRS Total Scores - Proportion of Responders After the First Infusion (Day 2 in TRD2001 and Day 3 or Day 4 in TRD2002) by Val/Val or Met Carriers and by Esketamine, Ketamine, Pooled Active or Placebo in All Subjects
Pooled Subjects

|  | Responders N (%) | Non-responders N (%) | Total |
|---|---|---|---|
| Val/Val | | | |
| Placebo | 2 (6.9%) | 27 (93.1%) | 29 |
| Active | 12 (41.4%) | 17 (58.6%) | 29 |
| Met Carriers | | | |
| Placebo | 0 (0%) | 11 (100.0%) | 11 |
| Active | 2 (9.1%) | 20 (90.9%) | 22 |

Placebo: pooled from placebos from Esketamine and Ketamine
Active: pooled from low, high dose from Esketamine and 2X/WK, 3X/WK from Ketamine

|  | Responders N (%) | Non-responders N (%) | Total |
|---|---|---|---|
| Val/Val | | | |
| Placebo | 2 (6.9%) | 27 (93.1%) | 29 |
| Esketamine | 6 (75.0%) | 2 (25.0%) | 8 |
| Ketamine | 6 (28.6%) | 15 (71.4%) | 21 |
| Met Carriers | | | |
| Placebo | 0 (0%) | 11 (100.0%) | 11 |
| Esketamine | 1 (11.1%) | 8 (88.9%) | 9 |
| Ketamine | 1 (7.7%) | 12 (92.3%) | 13 |

Placebo: pooled from placebos from Esketamine and Ketamine
Esketamine: pooled from low, high dose
Ketamine: pooled from 2X/WK, 3X/WK from JNJ-644059

C) % Remitters: The % remitters after the $1^{st}$ infusion (Day 2 in TRD2001 and Day 3 or Day 4 in TRD2002) by Val/Val or Met carriers and by placebo or active were as listed in Table P-3, below. Remit rate was higher in Val/Val subjects than in Met carriers.

TABLE P-3

MADRS Total Scores - Proportion of Remitters After the First Infusion (Day 2 in TRD2001 and Day 3 or Day 4 in TRD2002) by Val/Val or Met Carriers, and by Active or Placebo in All Subjects

|  | Remitters No. (%) | Non-remitters No. (%) | Total |
|---|---|---|---|
| Val/Val | | | |
| Placebo | 1 (3.4%) | 28 (96.6%) | 29 |
| Active | 6 (20.7%) | 23 (79.3%) | 29 |
| Met Carriers | | | |
| Placebo | 0 (0%) | 11 (100.0%) | 11 |
| Active | 1 (4.5%) | 21 (95.5%) | 22 |

Placebo: pooled from placebos from Esketamine and Ketamine
Active: pooled from low, high dose from Esketamine and 2X/WK, 3X/WK from Ketamine Association Analysis (Summary Results):

Association analysis between efficacy endpoints and SNP rs6265 were performed in placebo subjects (pooled from ESKETIVTRD2001 and KETIVTRD2002) and as well as in active subjects (pooled esketamine subjects from ESKETIVTRD2001 or ketamine subjects from KETIVTRD2002). Changes in MADRS total score from baseline after a single dose were based on Day 2 (for ESKETIVTRD2001) and Day 3 or Day 4 (for KETIVTRD2002).

Association between changes in MADRS total score from baseline and the SNP rs6265 after a single dose was evaluated in placebo subjects and active subjects using an ANCOVA model under a dominant model with baseline MADRS total score, and grouped genotype (Val/Val or Met carrier). A statistically significant result was found in active subjects (p=0.02). However, there was no evidence of association between change in MADRS total score and the SNP rs6265 in placebo subjects (p=0.14).

Association between the % responders and the SNP rs6265 after a single dose was evaluated in placebo subjects and active subjects using a logistic regression model under a dominant model with baseline MADRS total score and grouped genotype (Val/Val or Met carrier). A statistically significant result was found in active subjects (p=0.03). However, there was no evidence of association between % of responders and the SNP rs6265 in placebo subjects (p=0.68).

Association between the % remitters and the SNP rs6265 after a single dose was evaluated in placebo subjects and as well as in active subjects using a logistic regression model under a dominant model with baseline MADRS total score and grouped genotype (Val/Val or Met carrier). There was no evidence of association between the % remitters and the SNP rs6265 in placebo subjects or active subjects.

ESKETIVTRD2001 Analysis Results

A) MADRS Scores: Larger reductions in MADRS total score were observed in Val/Val subjects as compared to Met carriers for both placebo and esketamine. Mean changes in MADRS total score from baseline after the $1^{st}$ infusion (up to Day 4) by Val/Val or Met carriers and by placebo or active (pooled esketamine 0.2 mg/kg and 0.4 mg/kg, per Day 1 randomization) are as plotted in FIG. 1 and listed in Table E-1.

TABLE E-1

MADRS Score Mean Change from Baseline up to Day 4 pre-dose

|  | N | Mean (SD) | Range | Base Mean | N | Mean (SD) | Range |
|---|---|---|---|---|---|---|---|
| Val/Val Subjects | | | | | | | |
| Placebo | | | | | | | |
| D1PD | 8 | 34.63 (4.340) | (30.0; 42.0) | 34.63 | | | |
| D1H2 | 8 | 27.75 (4.132) | (21.0; 32.0) | 34.63 | 8 | −6.88 (5.194) | (−15.0; 0.0) |

TABLE E-1-continued

MADRS Score Mean Change from Baseline up to Day 4 pre-dose

| | N | Mean (SD) | Range | Base Mean | N | Mean (SD) | Range |
|---|---|---|---|---|---|---|---|
| D1H4 | 8 | 28.63 (5.805) | (18.0; 37.0) | 34.63 | 8 | −6.00 (6.568) | (−16.0; 2.0) |
| D2 | 8 | 28.25 (4.097) | (22.0; 36.0) | 34.63 | 8 | −6.38 (3.889) | (−12.0; 1.0) |
| D3 | 8 | 30.88 (4.853) | (24.0; 36.0) | 34.63 | 8 | −3.75 (5.148) | (−11.0; 4.0) |
| D4PD | 8 | 29.88 (6.105) | (18.0; 38.0) | 34.63 | 8 | −4.75 (5.445) | (−13.0; 0.0) |
| Active | | | | | | | |
| D1PD | 8 | 31.75 (5.007) | (23.0; 41.0) | 31.75 | | | |
| D1H2 | 8 | 13.00 (5.904) | (2.0; 18.0) | 31.75 | 8 | −18.75 (6.386) | (−29.0; −9.0) |
| D1H4 | 8 | 11.38 (4.926) | (2.0; 17.0) | 31.75 | 8 | −20.38 (6.186) | (−29.0; −12.0) |
| D2 | 8 | 10.13 (6.105) | (0.0; 19.0) | 31.75 | 8 | −21.63 (9.501) | (−33.0; −6.0) |
| D3 | 8 | 11.88 (10.494) | (0.0; 29.0) | 31.75 | 8 | −19.88 (13.474) | (−38.0; −3.0) |
| D4PD | 8 | 13.63 (11.698) | (1.0; 30.0) | 31.75 | 8 | −18.13 (14.515) | (−37.0; 0.0) |

Met Carriers

Placebo

| | N | Mean (SD) | Range | Base Mean | N | Mean (SD) | Range |
|---|---|---|---|---|---|---|---|
| D1PD | 1 | 30 (−) | (30.0; 30.0) | 30.00 | | | |
| D1H2 | 1 | 29 (−) | (29.0; 29.0) | 30.00 | 1 | −1 (−) | (−1.0; −1.0) |
| D1H4 | 1 | 29 (−) | (29.0; 29.0) | 30.00 | 1 | −1 (−) | (−1.0; −1.0) |
| D2 | 1 | 33 (−) | (33.0; 33.0) | 30.00 | 1 | 3 (−) | (3.0; 3.0) |
| D3 | 1 | 28 (−) | (28.0; 28.0) | 30.00 | 1 | −2 (−) | (−2.0; −2.0) |
| D4PD | 1 | 26 (−) | (26.0; 26.0) | 30.00 | 1 | −4 (−) | (−4.0; −4.0) |
| Active | | | | | | | |
| D1PD | 9 | 33.67 (3.937) | (28.0; 42.0) | 33.67 | | | |
| D1H2 | 9 | 20.78 (9.985) | (4.0; 34.0) | 33.67 | 9 | −12.89 (9.765) | (−26.0; 0.0) |
| D1H4 | 9 | 18.67 (10.198) | (6.0; 34.0) | 33.67 | 9 | −15.00 (9.287) | (−28.0; −2.0) |
| D2 | 9 | 21.89 (8.580) | (4.0; 33.0) | 33.67 | 9 | −11.78 (7.645) | (−30.0; −3.0) |
| D3 | 9 | 24.33 (9.028) | (9.0; 33.0) | 33.67 | 9 | −9.33 (8.000) | (−23.0; 0.0) |
| D4PD | 9 | 25.00 (10.452) | (5.0; 36.0) | 33.67 | 9 | −8.67 (9.566) | (−29.0; 0.0) |

B) % Responders: The % responders by Val/Val or Met carriers and by placebo or esketamine (per Day 1 randomization, however, all patients got active esketamine from day 4 on) on Days 2, 7, 17 and 35 were as listed in Table E-2, below. In esketamine subjects, response rates were higher in Val/Val subjects than in Met carriers

TABLE E-2

MADRS Total Scores, Proportion of Responders on Days 2, 7, 17 and 35 by Val/Val or Met Carriers and by Esketamine or Placebo (per Day 1 Randomization)

| | Responders No. (%) | Non-responders No. (%) | Total |
|---|---|---|---|
| Val/Val | | | |
| Placebo | | | |
| DAY 02 | 0 | 8 (100.0%) | 8 |
| DAY 07* | 5 (71.4%) | 2 (28.6%) | 7 |
| DAY 17* | 5 (71.4%) | 2 (28.6%) | 7 |
| DAY 35* | 4 (57.1%) | 3 (42.9%) | 7 |
| Esketamine | | | |
| DAY 02 | 6 (75.0%) | 2 (25.0%) | 8 |
| DAY 07 | 6 (75.0%) | 2 (25.0%) | 8 |
| DAY 17 | 7 (87.5%) | 1 (12.5%) | 8 |
| DAY 35 | 7 (87.5%) | 1 (12.5%) | 8 |
| Met Carriers | | | |
| Placebo | | | |
| DAY 02 | 0 | 1 (100.0%) | 1 |
| DAY 07* | 1 (100.0%) | 0 | 1 |
| DAY 17* | 1 (100.0%) | 0 | 1 |
| DAY 35* | 1 (100.0%) | 0 | 1 |
| Esketamine | | | |
| DAY 02 | 1 (11.1%) | 8 (88.9%) | 9 |
| DAY 07 | 3 (33.3%) | 6 (66.7%) | 9 |

TABLE E-2-continued

MADRS Total Scores, Proportion of Responders on Days 2, 7, 17 and 35 by Val/Val or Met Carriers and by Esketamine or Placebo (per Day 1 Randomization)

| | Responders No. (%) | Non-responders No. (%) | Total |
|---|---|---|---|
| DAY 17 | 6 (66.7%) | 3 (33.3%) | 9 |
| DAY 35 | 4 (44.4%) | 5 (55.6%) | 9 |

*All patients listed as "placebo" received active esketamine from day 4 onward. Therefore the response rates reported here from day 7 onwards as placebo (per day 1 randomization) reflect response to esketamine.

C) Duration of Response: The survival curves for the duration of response in esketamine responders per day 1 randomization after the open label active treatment phase (Day 17) by Val/Val or Met carriers in esketamine responders (Day 17) were as shown in FIG. 2 and Table E-3, below. In esketamine subjects (per Day 1 randomization), there were 13 responders on Day 17 (7 with Val/Val and 6 with Met carriers). Among those responders, all 7 (100%) Val/Val subjects maintained response status up to Day 35, i.e. 18 days after last dose. For the Met carriers, 2 out of 6 (33.3%) maintained response status up to Day 35.

TABLE E-3

Survival Function Estimates on the Duration of Response After Open Label Phase by Val/Val or Met Carriers in Esketamine Responders (Day 17) Per Day 1 Randomization

| Day | Survival | Failure | Survival Std. Err. | No. Failed | No. Left |
|---|---|---|---|---|---|
| Val/Val Subjects | | | | | |
| 0š | 1.0000 | 0 | 0 | 0 | 7 |
| 18* | | | | 0 | 6 |

TABLE E-3-continued

Survival Function Estimates on the Duration of Response After Open Label Phase by Val/Val or Met Carriers in Esketamine Responders (Day 17) Per Day 1 Randomization

| Day | Survival | Failure | Survival Std. Err. | No. Failed | No. Left |
|---|---|---|---|---|---|
| 18* | | | | 0 | 5 |
| 18* | | | | 0 | 4 |
| 18* | | | | 0 | 3 |
| 18* | | | | 0 | 2 |
| 18* | | | | 0 | 1 |
| 18* | | | | 0 | 0 |
| Met Carriers | | | | | |
| 0Š | 1.0000 | 0 | 0 | 0 | 6 |
| 4Š | | | | 1 | 5 |
| 4Š | | | | 2 | 4 |
| 4Š | 0.5000 | 0.5000 | 0.2041 | 3 | 3 |
| 18Š | 0.3333 | 0.6667 | 0.1925 | 4 | 2 |
| 18* | | | | 4 | 1 |
| 18* | | | | 4 | 0 |

*censored observations

The survival curves for the aforementioned duration of response by Val/Val or Met carriers in all responders to ketamine (Day 17) were as shown in FIG. 3 (FIG. 3B) and Table E-4, below. Among all subjects, there were 19 responders on Day 17 (12 with Val/Val and 7 with Met carriers). Among those responders, 11 out of 12 (91.7%) Val/Val maintained response status up to Day 35. For the Met carriers, 3 out of 7 (42.9%) maintained response status up to Day 35.

TABLE E-4

Survival Function Estimates on the Duration of Response on Day 17 by Val/Val or Met Carriers in All Responders

| Day | Survival | Failure | Survival Std. Err. | No. Failed | No. Left |
|---|---|---|---|---|---|
| Val/Val Subjects | | | | | |
| 0Š | 1.0000 | 0 | 0 | 0 | 12 |
| 11Š | 0.9167 | 0.0833 | 0.0798 | 1 | 11 |
| 18* | | | | 1 | 10 |
| 18* | | | | 1 | 9 |
| 18* | | | | 1 | 8 |
| 18* | | | | 1 | 7 |
| 18* | | | | 1 | 6 |
| 18* | | | | 1 | 5 |
| 18* | | | | 1 | 4 |
| 18* | | | | 1 | 3 |
| 18* | | | | 1 | 2 |
| 18* | | | | 1 | 1 |
| 18* | | | | 1 | 0 |
| Met Carriers | | | | | |
| 0Š | 1.0000 | 0 | 0 | 0 | 7 |
| 4Š | | | | 1 | 6 |
| 4Š | | | | 2 | 5 |
| 4Š | 0.5714 | 0.4286 | 0.1870 | 3 | 4 |
| 18Š | 0.4286 | 0.5714 | 0.1870 | 4 | 3 |
| 18* | | | | 4 | 2 |
| 18* | | | | 4 | 1 |
| 18* | | | | 4 | 0 |

*censored observations

D) % Remitters: The % remitters by Val/Val or Met carriers and by placebo or esketamine (per Day 1 randomization) on Days 2, 7, 17 and 35 were as listed in table E-5 below. In esketamine subjects, remit rates were higher in Val/Val subjects than in Met carriers at all timepoints. Remission was maintained longer in Val/Val than in Met carriers (Day 35).

TABLE E-5

MADRS Total cores, Proportion of Remitters on Days 2, 7, 17 and 35 by Val/Val or Met Carriers and by Esketamine or Placebo

| | Remitters No. (%) | Non-remitters No. (%) | Total |
|---|---|---|---|
| Val/Val | | | |
| Placebo | | | |
| DAY 02 | 0 | 8 (100.0%) | 8 |
| DAY 07* | 4 (57.1%) | 3 (42.9%) | 7 |
| DAY 17* | 3 (42.9%) | 4 (57.1%) | 7 |
| DAY 35* | 4 (57.1%) | 3 (42.9%) | 7 |
| Esketamine | | | |
| DAY 02 | 5 (62.5%) | 3 (37.5%) | 8 |
| DAY 07 | 6 (75.0%) | 2 (25.0%) | 8 |
| DAY 17 | 7 (87.5%) | 1 (12.5%) | 8 |
| DAY 35 | 7 (87.5%) | 1 (12.5%) | 8 |
| Met Carriers | | | |
| Placebo | | | |
| DAY 02 | 0 | 1 (100.0%) | 1 |
| DAY 07* | 0 | 1 (100.0%) | 1 |
| DAY 17* | 1 (100.0%) | 0 | 1 |
| DAY 35* | 1 (100.0%) | 0 | 1 |
| Esketamine | | | |
| DAY 02 | 1 (11.1%) | 8 (88.9%) | 9 |
| DAY 07 | 2 (22.2%) | 7 (77.8%) | 9 |
| DAY 17 | 2 (22.2%) | 7 (77.8%) | 9 |
| DAY 35 | 2 (22.2%) | 7 (77.8%) | 9 |

*All patients listed as "placebo" received active esketamine from day 4 onward. Therefore the remission rates reported here from day 7 onwards as placebo (per day 1 randomization) reflect response to esketamine KETIVTRD2002 Analysis Results A) MADRS Scores: Larger reductions in MADRS total score over most time points were observed in Val/Val carriers as compared to those Met carriers for both placebo and ketamine (pooled 2x/wk and 3x/wk). Summary statistics for MADRS total score over time by Val/Val or Met carriers and by ketamine 2x/wk, ketamine 3x/wk or placebo were as listed in Table K-1, below.

Similarly, mean changes in MADRS total scores from baseline over time (during the double-blinded phase) up to the primary endpoint at Day 15 by ValNal or Met carriers and by ketamine or placebo were shown in FIG. 4. (Note: The study continued beyond Day 15, however results from Day 15 onward are not presented since at Day 15, non-responders were permitted to received open label Ketamine, as per the clinical trial design.) Summary statistics for mean changes in MADRS total scores from baseline by Val/Val or Met carriers and by ketamine (pooled 2x/wk and 3x/wk) or placebo were as listed in Table K-1, below.

TABLE K-1

MADRS Total Scores - Actual Values and Changes from Baseline 10 on Days 3 or 4, 8, 15 and 29 by Val/Val or Met Carriers and by Ketamine or Placebo

|  | N | Mean (SD) | Range | Base Mean | N | Mean (SD) | Std. Err. | Range |
|---|---|---|---|---|---|---|---|---|
| | | | | | | Change from Baseline | | |
| Val/Val Placebo | | | | | | | | |
| DAY 03 or DAY 04 | 21 | 31.33 (9.123) | (9.0; 43.0) | 36.67 | 21 | −5.33 (8.206) | 1.791 | (−31.0; 2.0) |
| DAY 08 (DB) | 21 | 30.29 (13.150) | (3.0; 48.0) | 36.67 | 21 | −6.38 (11.859) | 2.588 | (−37.0; 6.0) |
| DAY 15 (DB) | 20 | 31.25 (9.673) | (10.0; 48.0) | 36.35 | 20 | −5.10 (8.058) | 1.802 | (−26.0; 4.0) |
| DAY 29 (DB) | 2 | 11.50 (9.192) | (5.0; 18.0) | 35.00 | 2 | −23.50 (10.607) | 7.500 | (−31.0; −16.0) |
| Val/Val Ketamine | | | | | | | | |
| DAY 03 or DAY 04 | 21 | 22.29 (7.551) | (6.0; 34.0) | 34.95 | 21 | −12.67 (7.742) | 1.689 | (−27.0; 0.0) |
| DAY 08 (DB) | 20 | 18.50 (8.030) | (6.0; 34.0) | 35.15 | 20 | −16.65 (9.309) | 2.082 | (−38.0; −4.0) |
| DAY 15 (DB) | 18 | 16.11 (8.159) | (5.0; 34.0) | 34.61 | 18 | −18.50 (7.906) | 1.863 | (−34.0; −4.0) |
| DAY 29 (DB) | 17 | 9.59 (7.969) | (0.0; 26.0) | 36.18 | 17 | −26.59 (8.938) | 2.168 | (−43.0; −11.0) |
| Met Carriers Placebo | | | | | | | | |
| DAY 03 or DAY 04 | 10 | 33.30 (6.165) | (24.0; 40.0) | 35.40 | 10 | −2.10 (5.782) | 1.828 | (−15.0; 8.0) |
| DAY 08 (DB) | 8 | 33.63 (4.406) | (29.0; 41.0) | 35.13 | 8 | −1.50 (4.472) | 1.581 | (−10.0; 5.0) |
| DAY 15 (DB) | 9 | 33.11 (6.882) | (17.0; 40.0) | 35.56 | 9 | −2.44 (7.955) | 2.652 | (−22.0; 5.0) |
| DAY 29 (DB) | 1 | 31 (—) | (31.0; 31.0) | 32.00 | 1 | −1 (—) |  | (−1.0; −1.0) |
| Met Carriers Ketamine | | | | | | | | |
| DAY 03 or DAY 04 | 13 | 25.92 (7.599) | (14.0; 38.0) | 32.77 | 13 | −6.85 (6.998) | 1.941 | (−22.0; 4.0) |
| DAY 08 (DB) | 11 | 17.00 (9.930) | (4.0; 33.0) | 32.64 | 11 | −15.64 (9.750) | 2.940 | (−33.0; −4.0) |
| DAY 15 (DB) | 11 | 15.18 (13.060) | (1.0; 44.0) | 32.64 | 11 | −17.45 (13.163) | 3.969 | (−36.0; 10.0) |
| DAY 29 (DB) | 9 | 10.78 (8.955) | (2.0; 32.0) | 32.78 | 9 | −22.00 (8.544) | 2.848 | (−33.0; −5.0) |

B) % Responders: Among ketamine subjects, response rates were higher on Day 3 or Day 4 and Day 15 in Val/Val subjects than in Met carriers, whereas response rates were similar on Days 8 and 29 in Val/Val subjects than in Met carriers. The % responders during the double blind phase by Val/Val or Met carriers and by ketamine (pooled 2×/wk and 3×/wk) or placebo were as listed in Table K-2 below.

TABLE K-2

MADRS Total Scores - Proportion of Responders on Days 3 or 4, 8, 15 and 29 by Val/Val or Met Carriers and by Treatment Group

|  | Responders N (%) | Non-responders N (%) | Total |
|---|---|---|---|
| Val/Val | | | |
| Placebo | | | |
| DAY 03 or DAY 04 | 2 (9.5%) | 19 (90.5%) | 21 |
| DAY 08(DB) | 4 (19.0%) | 17 (81.0%) | 21 |
| DAY 15(DB) | 2 (10.0%) | 18 (90.0%) | 20 |
| DAY 29(DB) | 1 (50.0%) | 1 (50.0%) | 2 |
| Ketamine Pooled | | | |
| DAY 03 or DAY 04 | 6 (28.6%) | 15 (71.4%) | 21 |
| DAY 08(DB) | 8 (40.0%) | 12 (60.0%) | 20 |
| DAY 15(DB) | 12 (66.7%) | 6 (33.3%) | 18 |
| DAY 29(DB) | 14 (82.4%) | 3 (17.6%) | 17 |
| Met Carriers | | | |
| Placebo | | | |
| DAY 03 or DAY 04 | 0 | 10 (100.0%) | 10 |
| DAY 08(DB) | 0 | 8 (100.0%) | 8 |
| DAY 15(DB) | 1 (11.1%) | 8 (88.9%) | 9 |
| DAY 29(DB) | 0 | 1 (100.0%) | 1 |
| Ketamine Pooled | | | |
| DAY 03 or DAY 04 | 1 (7.7%) | 12 (92.3%) | 13 |
| DAY 08(DB) | 5 (45.5%) | 6 (54.5%) | 11 |
| DAY 15(DB) | 6 (54.5%) | 5 (45.5%) | 11 |
| DAY 29(DB) | 8 (88.9%) | 1 (11.1%) | 9 |

C) Duration of Response: The survival curves for the duration of response after the double-blind phase Day 29 and up to Day 44 (i.e., up to 15 days after the last dose) by Val/Val or Met carriers in ketamine responders on Day 29 were as shown in FIG. 5 (where on the x-axis, 0 represents the starting point at Day 29 and 15 represents Day 44) and as listed in Table K-3, below. There were 22 ketamine responders on Day 29 (14 with Val/Val and 8 with Met carriers). Among those responders, 9 out of 14 (64.3%) in Val/Val maintain response status, versus 5 out of 8 (62.5%) in Met carriers maintain response status during the follow-up phase.

TABLE K-3

Survival Function Estimates on the Duration of Response During Follow-up Phase by Val/Val or Met Carriers in Ketamine Responders (Day 29)

| Day | Survival | Failure | Survival Std. Err. | No. Failed | No. Left |
|---|---|---|---|---|---|
| Val/Val Subjects ||||||
| 0Š | 1.0000 | 0 | 0 | 0 | 14 |
| 4Š | | | | 1 | 13 |
| 4Š | 0.8571 | 0.1429 | 0.0935 | 2 | 12 |
| 15* | | | | 2 | 11 |
| 16Š | 0.7792 | 0.2208 | 0.1129 | 3 | 10 |
| 17* | | | | 3 | 9 |
| 17* | | | | 3 | 8 |
| 17* | | | | 3 | 7 |
| 18Š | 0.6679 | 0.3321 | 0.1414 | 4 | 6 |
| 18* | | | | 4 | 5 |
| 18* | | | | 4 | 4 |
| 18* | | | | 4 | 3 |
| 18* | | | | 4 | 2 |
| 22* | | | | 4 | 1 |
| 38Š | 0 | 1.0000 | | 5 | 0 |
| Met Carriers ||||||
| 0Š | 1.0000 | 0 | 0 | 0 | 8 |
| 0* | | | | 0 | 7 |
| 10Š | | | | 1 | 6 |
| 10Š | 0.7143 | 0.2857 | 0.1707 | 2 | 5 |
| 11Š | 0.5714 | 0.4286 | 0.1870 | 3 | 4 |
| 17* | | | | 3 | 3 |
| 17* | | | | 3 | 2 |
| 18* | | | | 3 | 1 |
| 30* | | | | 3 | 0 |

*sensored observations

D) % Remitters: Among ketamine subjects, remit rates were higher in Met carriers than in Val/Val subjects, except on Day 3 or Day 4. Among placebo subjects, there were no remitters in Met carriers. The results for % remitters by Val/Val or Met carriers and by ketamine (pooled 2×/week and 3×/week) or placebo were as presented in Table K-4.

TABLE K-4

MADRS Total Scores - Proportion of Remitters on Days 3 or 4, 8, 15 and 29 by Val/Val or Met Carriers and by Treatment Group

| | Remitters No. (%) | Non-remitters No. (%) | Total |
|---|---|---|---|
| Val/Val ||||
| Placebo ||||
| DAY 03 or DAY 04 | 1 (4.8%) | 20 (95.2%) | 21 |
| DAY 08(DB) | 3 (14.3%) | 18 (85.7%) | 21 |
| DAY 15(DB) | 1 (5.0%) | 19 (95.0%) | 20 |
| DAY 29(DB) | 1 (50.0%) | 1 (50.0%) | 2 |
| Ketamine Pooled ||||
| DAY 03 or DAY 04 | 1 (4.8%) | 20 (95.2%) | 21 |
| DAY 08(DB) | 4 (20.0%) | 16 (80.0%) | 20 |
| DAY 15(DB) | 4 (22.2%) | 14 (77.8%) | 18 |
| DAY 29(DB) | 11 (64.7%) | 6 (35.3%) | 17 |
| Met Carriers ||||
| Placebo ||||
| DAY 03 or DAY 04 | 0 | 10 (100.0%) | 10 |
| DAY 08(DB) | 0 | 8 (100.0%) | 8 |
| DAY 15(DB) | 0 | 9 (100.0%) | 9 |
| DAY 29(DB) | 0 | 1 (100.0%) | 1 |
| Ketamine Pooled ||||
| DAY 03 or DAY 04 | 0 | 13 (100.0%) | 13 |
| DAY 08(DB) | 3 (27.3%) | 8 (72.7%) | 11 |
| DAY 15(DB) | 5 (45.5%) | 6 (54.5%) | 11 |
| DAY 29(DB) | 6 (66.7%) | 3 (33.3%) | 9 |

Formulation Example 1—Prophetic Example

An aqueous formulation of S-ketamine hydrochloride is prepared by mixing S-ketamine hydrochloride (at a concentration of 161.4 mg/mL) in water and then adding 1N NaOH$_{(aq)}$ to pH 5.0.

Formulation Example 2—Prophetic Example

Aqueous formulation of S-ketamine hydrochloride is prepared by mixing S-ketamine hydrochloride (at a concentration of 161.4 mg/mL) in water and then adding 10 mg/mL tauroursodeoxycholic acid (TUDCA). To the resulting mixture is added 1N NaOH$_{(aq)}$ to pH 4.5.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

| BRIEF DESCRIPTION OF SEQUENCE LISTINGS |||
|---|---|---|
| SEQ ID NO. | Sequence Val66Met polymorphysm on BDNF, dbSNP rs6265 [Homo sapien] ||
| 1 | ATCATTGGCTGACACTTTCGAACAC [A/G] TGATAGAAGAGCTGTTGGATGAGGA ||
| | (where [A/G] defines the position of the mutation) ||
| 2 | CTGCAGAAAG GCCTGGAATT ACAATCAGAT GGGCCACATG GCATCCCGGT GAAAGAAAGC CC TAACCAGTTT TCTGTCTTGT TTCTGCTTTC TCCCTACAGT TCCACCAGGT GAGAAGAGTG ATGACCATCC TTTTCCTTAC TATGGTTATT TCATACTTTG GTTGCATGAA GGCTGCCCCC ATGAAAGAAG CAAACATCCG AGGACAAGGT GGCTTGGCCT ACCCAGGTGT GCGGACCCAT GGGACTCTGG AGAGCGTGAA TGGGCCCAAG GCAGGTTCAA GAGGCTTGAC ATCATTGGCT GACACTTTCG AACAC R ||

| BRIEF DESCRIPTION OF SEQUENCE LISTINGS | |
|---|---|
| SEQ ID NO. | Sequence<br>Val66Met polymorphysm on BDNF, dbSNP rs6265 [*Homo sapien*] |
| | TGATAGAAGA GCTGTTGGAT GAGGACCAGA AAGTTCGGCC CAATGAAGAA AACAATAAGG<br>ACGCAGACTT GTACACGTCC AGGGTGATGC TCAGTAGTCA AGTGCCTTTG GAGCCTCCTC<br>TTCTCTTTCT GCTGGAGGAA TACAAAAATT ACCTAGATGC TGCAAACATG TCCATGAGGG<br>TCCGGCGCCA CTCTGACCCT GCCCGCCGAG GGGAGCTGAG CGTGTGTGAC AGTATTAGTG<br>AGTGGGTAAC GGCGG<br>CAGACAAAAA GACTGCAGTG GACATGTCGG GCGGGACGGT CACAGTCCTT GAAAAGGTCC<br>CTGTATCAAA AGGCCAACTG AAGCAATACT TCTACGAGAC CAAGTGCAAT CCCATGGGTT<br>ACACAAAAGA AGGCTGCAGG GGCATAGACA AAAGGCATTG GAACTCCCAG TGCCGAACTA<br>CCCAGTCGTA CGTGCGGGCC CTTACCATGG ATAGCAAAAA GAGAATTGGC TGGCGATTCA<br>TAAGGATAGA CACTTCTTGT GTATGTACAT TGACCATTAA AAGGGGAAGA TAGTGGATTT<br>ATGTTGTATA GATTAGATTA TATTGAGACA AAAATTATCT ATTTGTATAT ATACATAACA<br>GGGTAAATTA TTCAGTTAAG AAAAAAATAA TTTTATGAAC TGCATGTATA AATGAAGTTT<br>ATACAGTACA GTGGTTCTAC AATCTATTTA TTGGACATGT CCATGACCAG AAGGGAAACA<br>GTCATTTGCG CACAACTTAA AAAGTCTGCA TTACATTCCT TGATAATGTT GTGGTTTGTT<br>GCCGTTGCCA AGAACTGAAA ACATAAAAAG TTAAAAAAAA TAATAAATTG CATGCTGCTT<br>TAATTGTGAA TTGATAATAA ACTGTCCTCT TTCAGAAAAC AGAAAAAAAC ACACACACAC<br>ACAACAAAAA TTTGAACCAA AACATTCCGT TTACATTTTA GACAGTAAGT ATCTTCGTTC<br>TTGTTAGTAC TATATCTGTT TTACTGCTTT TAACTTCTGA TAGCGTTGGA ATTAAAACAA<br>TGTCAAGGTG CTGTTGTCAT TGCACCCCCA AGGGGAACTA ACCGCCTCCC ACACACTATA<br>TTCCTGCCAC CCCCGCCCCA CCCTACACCG GCCCCGCACC GCCCC<br>(wherein R represents the position of the polymorphism) |

What is claimed is:

1. A method of treating major depressive disorder in a human patient in need thereof, comprising:
intranasally administering (S)-2-(2-chlorophenyl)-2-(methylamino)cyclohexanone in an induction dosage to the patient in an amount in the range of from about 56 mg to about 84 mg in an induction phase, wherein the induction phase comprises a treatment period of about four weeks, and the induction dosage is administered at a frequency of twice per week during the induction phase.

2. The method of claim 1, wherein the induction dosage is about 56 mg or about 84 mg.

3. The method of claim 2, wherein the patient exhibits suicidal ideation or behavior.

4. The method of claim 2, wherein the major depressive disorder is treatment resistant depression.

5. The method of claim 2, further comprising adjunctive treatment with a therapeutically effective amount of one or more antidepressants during the induction phase.

6. The method of claim 5, wherein the patient exhibits suicidal ideation or behavior.

7. The method of claim 6, wherein the (S)-2-(2-chlorophenyl)-2-(methylamino)cyclohexanone is administered as its corresponding hydrochloride salt during the induction phase.

8. The method of claim 7, wherein the one or more antidepressants is an oral antidepressant.

9. The method of claim 5, wherein the major depressive disorder is treatment resistant depression.

10. The method of claim 9, wherein the (S)-2-(2-chlorophenyl)-2-(methylamino)cyclohexanone is administered as its corresponding hydrochloride salt during the induction phase.

11. The method of claim 2, wherein the induction dosage is about 84 mg.

12. The method of claim 11, wherein the depression major depressive disorder is treatment resistant depression.

13. The method of claim 11, wherein the patient exhibits suicidal ideation or behavior.

14. The method of claim 11, further comprising adjunctive treatment with a therapeutically effective amount of one or more antidepressants during the induction phase.

15. The method of claim 14, wherein the patient exhibits suicidal ideation or behavior.

16. The method of claim 15, wherein the (S)-2-(2-chlorophenyl)-2-(methylamino)cyclohexanone is administered as its corresponding hydrochloride salt during the induction phase.

17. The method of claim 14, wherein the major depressive disorder is treatment resistant depression.

18. The method of claim 17, wherein the (S)-2-(2-chlorophenyl)-2-(methylamino)cyclohexanone is administered as its corresponding hydrochloride salt during the induction phase.

19. The method of claim 1, wherein the (S)-2-(2-chlorophenyl)-2-(methylamino)cyclohexanone is administered as its corresponding hydrochloride salt during the induction phase.

20. A method of treating depression in a human patient in need thereof, the method having an induction phase and a subsequent maintenance phase, comprising:
intranasally administering (S)-2-(2-chlorophenyl)-2-(methylamino)cyclohexanone in an induction dosage to the patient in an amount in the range of from about 28 mg to about 84 mg in the induction phase, wherein the induction phase comprises a treatment period of about four weeks, and the induction dosage is administered at a frequency of twice per week during the induction phase; and
intranasally administering (S)-2-(2-chlorophenyl)-2-(methylamino)cyclohexanone in a maintenance dosage in an amount in the range of from about 56 mg to about 84 mg in the maintenance phase, wherein the maintenance dosage is administered at a frequency of once per week or once every two weeks.

21. The method of claim 20, wherein the induction dosage is about 56 mg or about 84 mg, and the maintenance dosage is about 56 mg or about 84 mg.

22. The method of claim 21, wherein the depression is major depressive disorder.

23. The method of claim 21, wherein the depression is treatment resistant depression.

24. The method of claim 21, further comprising adjunctive treatment with a therapeutically effective amount of one or more antidepressants during the induction phase and the maintenance phase.

25. The method of claim 24, wherein the depression is major depressive disorder.

26. The method of claim 25, wherein the (S)-2-(2-chlorophenyl)-2-(methylamino)cyclohexanone is administered as its corresponding hydrochloride salt during the induction phase and maintenance phase.

27. The method of claim 24, wherein the depression is treatment resistant depression.

28. The method of claim 27, wherein the (S)-2-(2-chlorophenyl)-2-(methylamino)cyclohexanone is administered as its corresponding hydrochloride salt during the induction phase and maintenance phase.

29. The method of claim 28, wherein the one or more antidepressants is an oral antidepressant.

30. The method of claim 20, wherein the (S)-2-(2-chlorophenyl)-2-(methylamino)cyclohexanone is administered as its corresponding hydrochloride salt during the induction phase and maintenance phase.

* * * * *

SEQUENCE LISTING

<160> NUMBER OF SEQ ID NOS: 2

<210> SEQ ID NO 1
<211> LENGTH: 51
<212> TYPE: DNA
<213> ORGANISM: Homo sapiens

<400> SEQUENCE: 1
atcattggct gacactttcg aacacrtgat agaagagctg ttggatgagg a         51

<210> SEQ ID NO 2
<211> LENGTH: 1458
<212> TYPE: DNA
<213> ORGANISM: Homo sapiens

<400> SEQUENCE: 2
ctgcagaaag gcctggaatt acaatcagat gggccacatg gcatcccggt gaaagaaagc      60
cctaaccagt tttctgtctt gtttctgctt tctccctaca gttccaccag gtgagaagag     120
tgatgaccat ccttttcctt actatggtta tttcatactt tggttgcatg aaggctgccc     180
ccatgaaaga agcaaacatc cgaggacaag gtggcttggc ctacccaggt gtgcggaccc     240
atgggactct ggagagcgtg aatgggccca aggcaggttc aagaggcttg acatcattgg     300
ctgacacttt cgaacacrtg atagaagagc tgttggatga ggaccagaaa gttcggccca     360
atgaagaaaa caataaggac gcagacttgt acacgtccag ggtgatgctc agtagtcaag     420
tgcctttgga gcctcctctc tctttctgc tggaggaata caaaaattac ctagatgctg     480
caaacatgtc catgagggtc cggcgccact ctgaccctgc ccgccgaggg gagctgagcg     540
tgtgtgacag tattagtgag tgggtaacgg cggcagacaa aaagactgca gtggacatgt     600
cgggcgggac ggtcacagtc cttgaaaagg tccctgtatc aaaaggccaa ctgaagcaat     660
acttctacga gaccaagtgc aatcccatgg gttacacaaa agaaggctgc aggggcatag     720
acaaaaggca ttggaactcc cagtgccgaa ctacccagtc gtacgtgcgg gcccttacca     780
tggatagcaa aaagagaatt ggctggcgat tcataaggat agacacttct gtgtatgta     840

```
cattgaccat taaaaggggga agatagtgga tttatgttgt atagattaga ttatattgag      900
acaaaaatta tctatttgta tatatacata acagggtaaa ttattcagtt aagaaaaaaa      960
taattttatg aactgcatgt ataaatgaag tttatacagt acagtggttc tacaatctat     1020
ttattggaca tgtccatgac cagaagggaa acagtcattt gcgcacaact taaaaagtct     1080
gcattacatt ccttgataat gttgtggttt gttgccgttg ccaagaactg aaaacataaa     1140
aagttaaaaa aaataataaa ttgcatgctg ctttaattgt gaattgataa taaactgtcc     1200
tctttcagaa aacagaaaaa aacacacaca cacacaacaa aaatttgaac caaaacattc     1260
cgtttacatt ttagacagta agtatcttcg ttcttgttag tactatatct gttttactgc     1320
ttttaacttc tgatagcgtt ggaattaaaa caatgtcaag gtgctgttgt cattgcaccc     1380
ccaaggggaa ctaaccgcct cccacacact atattcctgc cacccccgcc ccaccctaca     1440
ccggccccgc accgcccc                                                   1458
```